(12) United States Patent
Zelder et al.

(10) Patent No.: US 8,399,214 B2
(45) Date of Patent: Mar. 19, 2013

(54) USE OF DIMETHYL DISULFIDE FOR METHIONINE PRODUCTION IN MICROORAGANISMS

(75) Inventors: Oskar Zelder, Speyer (DE); Stefan Haefner, Speyer (DE); Andrea Herold, Ketsch (DE); Corinna Klopprogge, Mannheim (DE); Hartwig Schroder, Nussloch (DE); R. Rogers Yocum, Lexington, MA (US); Mark K. Williams, Revere, MA (US)

(73) Assignee: Evonik Degussa GmbH, Essen (DE)

( * ) Notice: Subject to any disclaimer, the term of this patent is extended or adjusted under 35 U.S.C. 154(b) by 881 days.

(21) Appl. No.: 11/988,971

(22) PCT Filed: Jul. 18, 2006

(86) PCT No.: PCT/US2006/027855
§ 371 (c)(1),
(2), (4) Date: Feb. 10, 2009

(87) PCT Pub. No.: WO2007/011939
PCT Pub. Date: Jan. 25, 2007

(65) Prior Publication Data
US 2009/0281353 A1 Nov. 12, 2009

Related U.S. Application Data

(60) Provisional application No. 60/700,698, filed on Jul. 18, 2005, provisional application No. 60/713,907, filed on Sep. 1, 2005.

(51) Int. Cl.
*C12P 1/00* (2006.01)
(52) U.S. Cl. .......................................................... 435/41
(58) Field of Classification Search .................. None
See application file for complete search history.

(56) References Cited

U.S. PATENT DOCUMENTS 3,962,429 A * 6/1976 Furuno et al. .................. 514/41

FOREIGN PATENT DOCUMENTS
WO WO 93/17112 * 9/1993

OTHER PUBLICATIONS

Kromer, J.O., at el., "In Vivo Quantification of Intracellular Amino Acids and Intermediates of the Methionine Pathway in *Corynebacterium glutamicum*", Analytical Biochemistry, 2005, vol. 340, pp. 171-173.
Kromer, J.O., et al., "Metabolic Pathway Analysis for Rational Design of L-Methionine Production by *Escherichia coli* and *Corynebacterium glutamicum*", Metabolic Engineering, 2006, vol. 8, pp. 353-369.
Lee, H.-S., et al., "Methionine Biosynthesis and its Regulation in *Corynebacterium glutamicum*: Parallel Pathways of Transsulfuration and Direct Sulfhydrylation", Appl. Microbiol Biotechnol, 2003, vol. 62, pp. 459-467.
International Search Report for PCT/US2006/027855, mailed Apr. 12, 2007.
International Preliminary Report on Patentability for PCT/US2006/027855, issued Jan. 22, 2008.

* cited by examiner

*Primary Examiner* — Albert Navarro
(74) *Attorney, Agent, or Firm* — Novak Druce Connolly Bove + Quigg LLP

(57) ABSTRACT

The present invention features improved processes and organisms for the production of methionine. The invention demonstrates that a ΔmetF organism or a ΔmetE AmetH organism, for example, mutants of *C. glutamicum* or *E. coli*, can use a methyl capped sulfide source, e.g., dimethyl disulfide (DMDS), as a source of both sulfur and a methyl group, bypassing the need for MetH/MetE and MetF activity and the need to reduce sulfate, for the synthesis of methionine. Also described in this patent are data implicating MetY (also called MetZ) as an enzyme that incorporates a methyl capped sulfide source, e.g., DMDS, into methionine. A ΔmetF ΔmetB strain of *C. glutamicum* can use a methyl capped sulfide source, e.g., DMDS, as a source of both sulfide and a methyl group. Furthermore, methionine production by engineered prototrophic organisms that overproduce O-acetyl-homoserine was improved by the addition of a methyl capped sulfide source, e.g., DMDS.

33 Claims, 8 Drawing Sheets

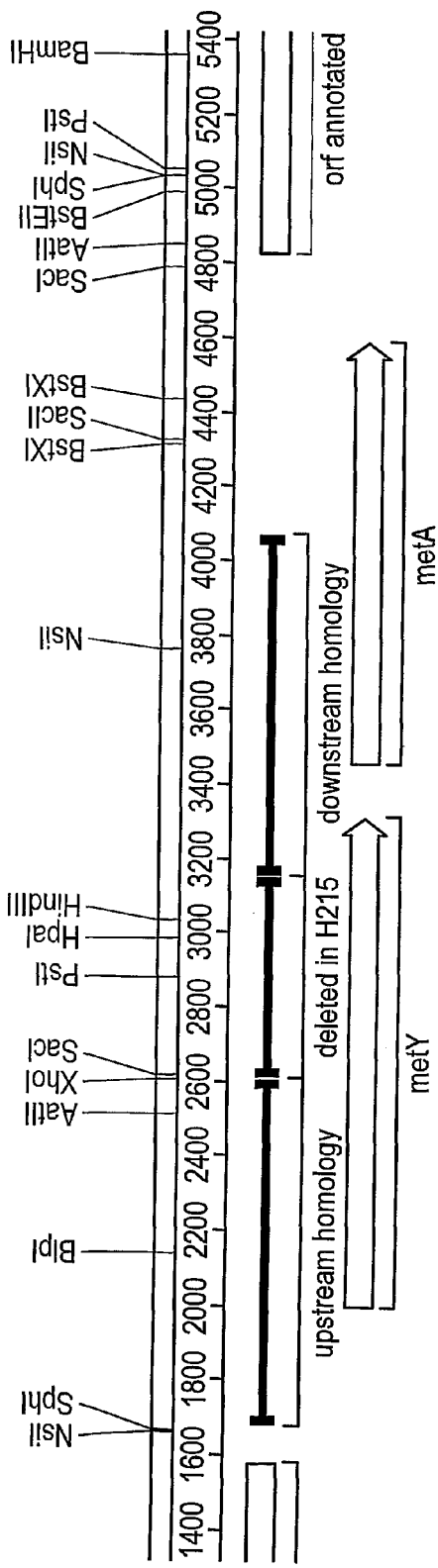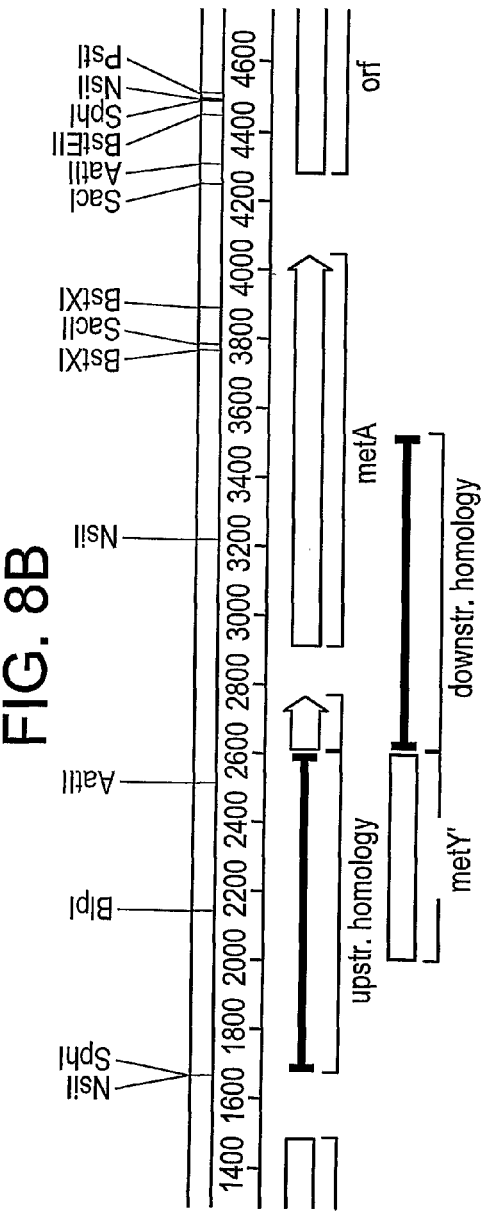
FIG. 8A
FIG. 8B

# USE OF DIMETHYL DISULFIDE FOR METHIONINE PRODUCTION IN MICROORAGANISMS

RELATED APPLICATIONS

This application claims priority to U.S. Provisional Patent Application No. 60/700,698, filed on Jul. 18, 2005, entitled "Use of Dimethyl Disulfide for Methionine Production in Microrganisms" and U.S. Provisional Patent Application No. 60/713,907, filed Sep. 1, 2005 entitled "Use of Dimethyl Disulfide for Methionine Production in Microrganisms".

This application is related to U.S. Provisional Patent Application No. 60/700,557, filed on Jul. 18, 2005, entitled "Use of a *Bacillus* MetI Gene to Improve Methionine Production in Microorganisms" and U.S. Provisional Patent Application No. 60/60/713,905, filed Sep. 1, 2005, entitled "Use of a *Bacillus* MetI Gene to Improve Methionine Production in Microorganisms"

This application is also related to and U.S. Provisional Patent Application No. 60/714,042, filed on Sep. 1, 2005, entitled "Methionine Producing Recombinant Microorganism" and U.S. Provisional Patent Application No. 60/700,699, filed on Jul. 18, 2005, entitled "Methionine Producing Recombinant Microorganism".

The entire contents of each of these patent applications are hereby expressly incorporated herein by reference including without limitation the specification, claims, and abstract, as well as any figures, tables, or drawings thereof.

BACKGROUND OF THE INVENTION

Methionine is currently produced as a DL-methionine racemic mixture by a well-established chemical process that involves toxic, dangerous, flammable, unstable, and noxious materials or intermediates. The starting materials for the chemical production of methionine are acrolein, methylmercaptan, and hydrogen cyanide. The chemical synthesis of methionine involves the reaction of methylmercaptan and acrolein producing the intermediate 3-methylmercaptopropionaldehyde (MMP). Further processing involves reacting MMP with hydrogen cyanide to form 5-(2-methylthioethyl) hydantoin, which is then hydrolysed using caustics such as NaOH together with $Na_2CO_3$, $NH_3$, and $CO_2$. Subsequently, sodium DL-methionine is neutralized with sulfuric acid and $Na_2CO_3$ to yield DL-methionine, $Na_2SO_4$, and $CO_2$. This process yields a large excess of unused compounds in comparison to the amount of methionine produced that poses an economic and ecological challenge.

Fermentative processes for methionine production are typically based on cultivating microorganisms with nutrients including carbohydrate sources, e.g., sugars, such as glucose, fructose, or sucrose, nitrogen sources, e.g., ammonia, and sulfur sources e.g., sulfate or thiosulfate, together with other necessary media components. This process yields L-methionine and biomass as a byproduct with no toxic dangerous, flammable, unstable, and/or noxious starting materials.

However, in order for an organism (e.g., a microorganism) to produce methionine from sulfate as a sulfur source, the sulfur atom must be first reduced to sulfide. This process is energy intensive, so that feeding the microorganism a sulfur source that is more reduced than sulfate would improve the process. One such reduced sulfur source is thiosulfate, in which one of the two sulfur atoms is already reduced. Another source of reduced sulfur is methane thiol, which contains a fully reduced sulfur atom.

The use of methane thiol for the production of methionine offers two advantages. First, as mentioned above, the sulfur atom is already reduced. Second, a methyl group is supplied, which could potentially bypass the need for two of the enzymes that are normally required for methionine biosynthesis, methyltetrahydrofolate reductase (MetF) and methionine synthase (MetE and/or MetH). There are literature reports that disclose that some microorganisms, for example *Saccharomyces cerevisiae*, can enzymatically incorporate methane thiol directly into methionine by reacting it with O-acetyl homoserine (Yamagata, S. 1971. *J. Biochem.* (Tokyo) 70:1035). Methods for the use of methane thiol in the production of methionine are also disclosed in WO 93/17112 and WO 2004/076659.

However, the use of methane thiol for the production of methionine also has disadvantages. It is a toxic, explosive gas that readily oxidizes in air, and it is noxious. The chemical process for producing methionine also uses methane thiol as one of the substrates, so engineers have learned to handle the compound on an industrial scale. Nonetheless, improved processes for the production of methionine that do not use methane thiol would be of great benefit.

SUMMARY OF THE INVENTION

The present invention relates to improved processes (e.g. microbial syntheses) for the production of methionine. The present inventors have discovered a sulfur and/or methyl group source other than methane thiol that can be used for the production of methionine. In particular, the present inventors have discovered that dimethyl disulfide (DMDS), also referred to as methyl disulfide or $CH_3$—S—S—$CH_3$, can be added to culture media and used by a microorganism as a source of both sulfide and a methyl group, bypassing the need for MetH/MetE and MetP activity and the need to reduce sulfate, for the synthesis of methionine.

In addition, the present invention demonstrates that a microorganism having a deregulated methionine biosynthetic pathway, e.g., a deregulated O-acetyl-homoserine sulfhydrylase, and/or a deregulated homoserine acetyltransferase and/ or a deregulated homoserine dehydrogenase, can use a methyl capped sulfide compound, e.g., a sulfur and/or methyl group source, e.g., dimethyl disulfide (DMDS), for the synthesis of methionine. Furthermore, the inventors have discovered that methionine production by engineered prototrophic strains that accumulate O-acetyl-homoserine is improved by the addition of DMDS.

Accordingly, in one aspect the present invention features a method for the production of methionine, comprising culturing a microorganism in the presence of a methyl capped sulfide compound, e.g., a sulfur and/or methyl group source, e.g., dimethyl disulfide (DMDS), such that methionine is produced. In one embodiment, the methyl capped sulfide compound, e.g., a sulfur and/or methyl group source, e.g., DMDS, is present at 0.02% or higher in the culture. In another embodiment, the methyl capped sulfide compound, e.g., a sulfur and/or methyl group source, e.g., DMDS, is present at 0.06% or higher in the culture. In other embodiments, the methyl capped sulfide compound, e.g., the sulfur and/or methyl group source, is selected from the group consisting of dimethyl trisulfide (DMTS) or $CH_3$—S—S—S—$CH_3$, dimethyltetrasulfide (DMTS) or $CH_3$—S—S—S—S—$CH_3$, or a higher molecular weight polymer of sulfide, the ends of which are capped by methyl groups.

Another aspect of the invention features a method of producing methionine, comprising culturing a methionine producing microorganism in the presence of a slow release methyl capped sulfide delivery system, e.g., a sulfur and/or methyl group delivery system, e.g., a dimethyl disulfide (DMDS) delivery system, such that methionine is produced. In one embodiment, the slow release methyl capped sulfide delivery system, e.g., a slow release sulfur and/or methyl group delivery system, e.g., a slow release delivery system of DMDS, is Amberlite™ XAD4. In one embodiment, the slow release delivery system releases DMDS at a level totaling 0.1% or higher in the culture medium. In yet another embodiment, the slow release delivery system releases DMDS at a level totaling 0.3% or higher in the culture medium. In one embodiment, the slow release DMDS delivery system comprises a liquid that is immiscible with water, but which dissolves DMDS. In one embodiment, the slow release methyl capped sulfide delivery system, e.g., a sulfur and/or methyl group delivery system, e.g., a slow release delivery system of DMDS, comprises a liquid selected from the group consisting of animal oils, mineral oils, chemical oils, vegetable oils, synthetic oils, organic solvent, chloro-carbons, fluoro-carbons, chloro-fluorocarbons, or combinations thereof. In another embodiment, the slow release methyl capped sulfide delivery system, e.g., the sulfur and/or methyl group delivery system, e.g., a slow release delivery system of DMDS, comprises a liquid that is immiscible with water, but which dissolves the methyl capped sulfide compound, e.g., the sulfur and/or methyl group source, e.g., DMDS. In yet another embodiment, the slow release methyl capped sulfide delivery system, e.g., the sulfur and/or methyl group delivery system, e.g., a DMDS slow release delivery system, is a slow controlled feed of a methyl capped sulfide compound, e.g., a sulfur and/or methyl group source, e.g., a slow controlled DMDS feed. In another embodiment, the slow release methyl capped sulfide delivery system, e.g., the sulfur and/or methyl group delivery system, e.g., the DMDS slow release delivery system, is a membrane that is permeable to a methyl capped sulfide compound, e.g., a sulfur and/or methyl group source, e.g., DMDS. In another embodiment, the DMDS slow release system is delivering DMDS in a gaseous state, for example by, evaporating or boiling liquid DMDS, or by, for example, bubbling air or oxygen through liquid DMDS on the way to the fermentation vessel. In one embodiment, the methionine producing microorganism belongs to the genus Corynebacterium. In another embodiment, the methionine producing microorganism is Corynebacterium glutamicum. In yet another embodiment, the methionine producing microorganism is selected from the group consisting of Gram-negative bacteria (e.g. Escherichia coli or related Enterobacteria), Gram-positive bacteria (e.g. Bacillus subtilis or related Bacillus), yeast (e.g. Saccharomyces cerevisiae or related yeast strains), and Archaea. In one embodiment, the methionine producing microorganism has at least one methionine biosynthetic enzyme deregulated. In another embodiment, the microorganism has a deregulated O-acetyl-homoserine sulfhydrylase. In yet another embodiment, the methionine producing microorganism has at least two methionine biosynthetic enzymes deregulated. In one embodiment, the microorganism has a deregulated homoserine acetyltransferase and a deregulated homoserine dehydrogenase. In another embodiment, the microorganism has a deregulated O-acetyl-homoserine sulfhydrylase and a deregulated homoserine acetyltransferase.

Another aspect of the invention features a method of producing methionine, comprising culturing a microorganism having a deregulated methionine biosynthetic pathway in the presence of a methyl capped sulfide compound, e.g., a sulfur and/or methyl group source, e.g., dimethyl disulfide (DMDS), such that methionine is produced. In one embodiment, the microorganism belongs to the genus Corynebacterium. In another embodiment, the microorganism is Corynebacterium glutamicum. In yet another embodiment, the microorganism is selected from the group consisting of: Gram-negative bacteria (e.g. Escherichia coli or related Enterobacteria), Gram-positive bacteria (e.g. Bacillus subtilis or related Bacillus), yeast (e.g. Saccharomyces cerevisiae or related yeast strains), and Archaea. In one embodiment, the microorganism has a deregulated O-acetyl-homoserine sulfhydrylase. In another embodiment, the microorganism has a deregulated homoserine acetyltransferase and a deregulated homoserine dehydrogenase. In yet another embodiment, the microorganism has a deregulated O-acetyl-homoserine sulfhydrylase and a deregulated homoserine acetyltransferase.

Yet another aspect of the invention features a product synthesized according to any of the above methods.

Another aspect of the invention features a recombinant microorganism for the production of methionine in the presence of a methyl capped sulfide compound, e.g., sulfur and/or methyl group source, e.g., dimethyl disulfide (DMDS), said microorganism having a deregulated methionine biosynthetic pathway. In one embodiment, the microorganism belongs to the genus Corynebacterium. In another embodiment, the microorganism is Corynebacterium glutamicum. In yet another embodiment, the microorganism is selected from the group consisting of: Gram-negative bacteria (e.g. Escherichia coli or related Enterobacteria), Gram-positive bacteria (e.g. Bacillus subtilis or related Bacillus), yeast (e.g. Saccharomyces cerevisiae or related yeast strains), and Archaea. In one embodiment, the microorganism has a deregulated O-acetyl-homoserine sulfhydrylase. In another embodiment, the microorganism has a deregulated homoserine acetyltransferase and a deregulated homoserine dehydrogenase. In yet another embodiment, the microorganism has a deregulated O-acetyl-homoserine sulfhydrylase and a deregulated homoserine acetyltransferase.

Yet another aspect of the invention features a method for identifying methionine feedback-resistant O-acetylhomoserine sulfhydrylase and/or O-succinylhomoserine sulfhydrylase enzymes and/or genes (e.g., mutant genes or alleles) encoding said methionine feedback-resistant enzymes. In one embodiment, the invention features a method for identifying a mutant allele that encodes an O-acetylhomoserine sulfhydrylase or O-succinylhomoserine sulfhydrylase that is resistant to feedback inhibition by methionine, comprising: a) contacting a microorganism that is dependent on DMDS and a plasmid encoded O-acetylhomoserine sulfhydrylase or O-succinylhomoserine sulfhydrylase for growth on a methionine free medium with a methionine analog that inhibits growth of said microorganism, b) selecting for mutant variants of said microorganism that are resistant to said analog, c) isolating said mutant variants wherein the resistant phenotype is encoded by said plasmid, and d) determining the DNA sequence of the relevant portion of said plasmid to identify mutant plasmids that have an altered sequence in the coding region for said O-acetylhomoserine sulfhydrylase or O-succinylhomoserine sulfhydrylase. The invention also features novel mutant O-acetylhomoserine sulfhydrylase or O-succinylhomoserine sulfhydrylase enzymes isolated by this method, genes encoding said mutant enzymes, as well as organisms that contain said mutant enzymes.

BRIEF DESCRIPTION OF THE DRAWINGS

FIGS. 8A-8B are schematics of the structure of the *C. glutamicum* chromosome in the region of metY before (8A) and after (8B) deletion of a portion of metY using plasmid H215.

DETAILED DESCRIPTION OF THE INVENTION

Figure 1:
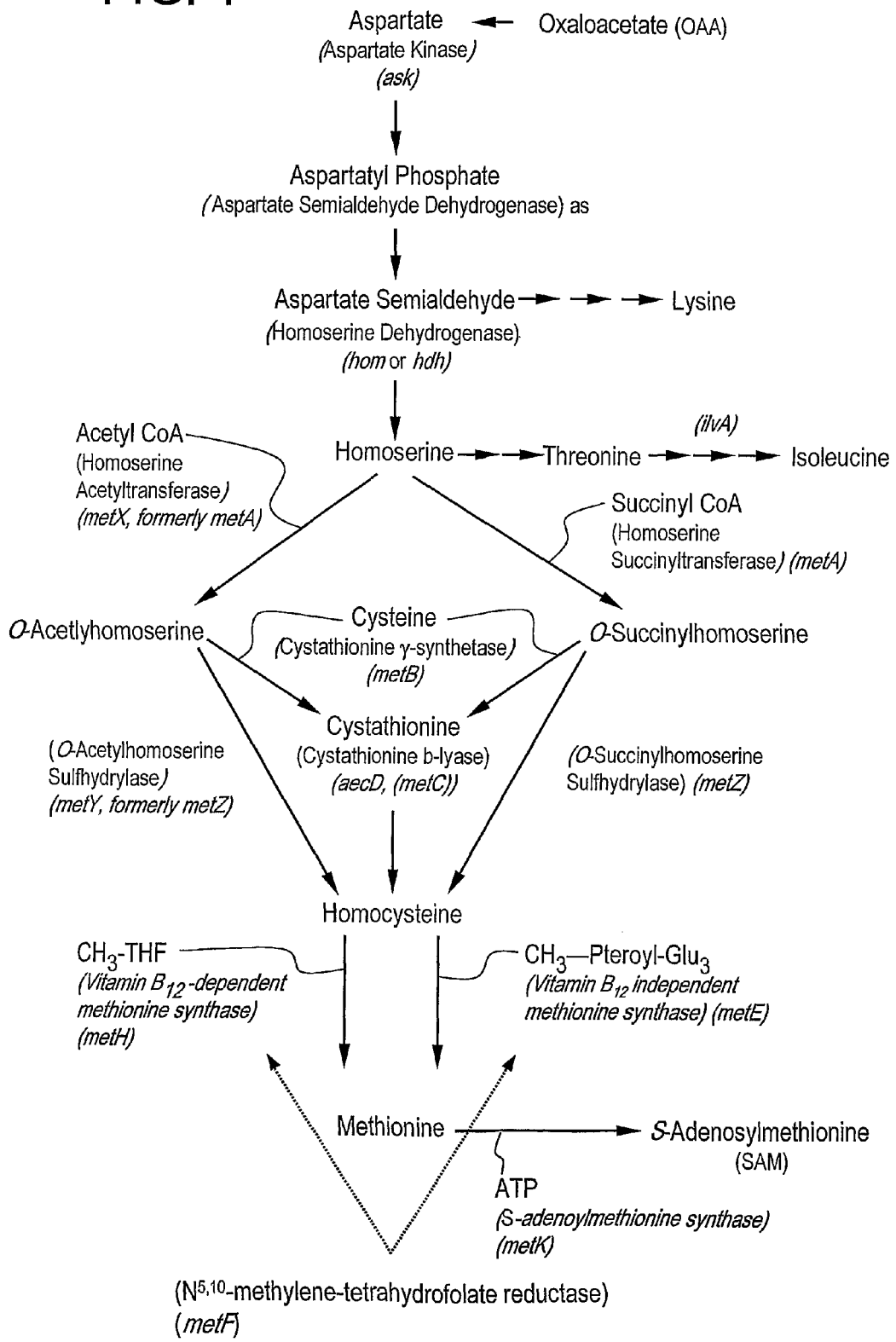
FIG. 1 is a schematic representation of the methionine biosynthetic pathway. Methionine biosynthetic enzymes are depicted in bold and their corresponding genes are indicated in italics.

The present invention is based, at least in part, on the discovery of improved methods (e.g., microbial syntheses) for the production of methionine. As described herein, the production of methionine by chemical methods currently uses noxious and dangerous chemicals, such as methane thiol, as a sulfur source. It has been discovered that a less hazardous and noxious source of sulfur can be utilized for the biosynthetic production of methionine. In particular, the present inventors have discovered that a methyl capped sulfide compound, e.g., a sulfur and/or methyl group source, e.g., dimethyl disulfide (DMDS), also referred to as methyl disulfide, can be added to a culture medium and used by a microorganism. As described in the appended examples, a ΔmetF strain or a ΔmetE ΔmetH strain of *C. glutamicum* can use a methyl capped sulfide compound, e.g., a sulfur and/or methyl group source, e.g. dimethyl disulfide (DMDS), as a source of both sulfide and a methyl group, bypassing the need for Met et E and MetF activity and the need to reduce sulfate, for the synthesis of methionine.

The use of a methyl capped sulfide compound, e.g., a sulfur and/or methyl group source, e.g., dimethyl disulfide, for the production of methionine, offers most of the advantages of methane thiol but not most of the disadvantages. DMDS is the oxidized disulfide dimer of methane thiol, which is a relatively inexpensive byproduct of the petroleum distilling industry. It is a liquid at room temperature, with a boiling point of about 109° C. DMDS is poorly soluble in water; if added to a growth medium at a concentration of 0.1% or higher, in particular at a concentration of 0.3% or higher, much of the DMDS remains as an oil on the bottom or on the sides of the container.

Furthermore, the present invention demonstrates that MetY (also referred to as MetZ; O-acetyl-homoserine sulfhydrylase) is an enzyme that incorporates a methyl capped sulfide compound, e.g., a sulfur and/or methyl group source, e.g., DMDS, directly or indirectly into methionine, since a ΔmetF ΔmetB strain of *C. glutamicum* can use a methyl capped sulfide compound, e.g., a sulfur and/or methyl group source, e.g., DMDS, as a source of both sulfide and a methyl group. Furthermore, methionine production by engineered prototrophic strains that accumulate O-acetyl-homoserine was improved by the addition of a methyl capped sulfide compound, e.g., a sulfur and/or methyl group source, e.g. DMDS.

Accordingly, the present invention provides methods and microorganisms for the production of methionine.

In order that the present invention may be more readily understood, certain terms are first defined herein.

The term "methionine biosynthetic pathway" includes the biosynthetic pathway involving methionine biosynthetic enzymes (e.g., polypeptides encoded by biosynthetic enzyme-encoding genes), compounds (e.g., precursors, substrates, intermediates or products), cofactors and the like utilized in the formation or synthesis of methionine. The term "methionine biosynthetic pathway" includes the biosynthetic pathway leading to the synthesis of methionine in a microorganism (e.g., in vivo) as well as the biosynthetic pathway leading to the synthesis of methionine in vitro.

The term "methionine biosynthetic enzyme" includes any enzyme utilized in the formation of a compound (e.g., intermediate or product) of the methionine biosynthetic pathway. "Methionine biosynthetic enzyme" includes enzymes involved in e.g., the "transsulfuration pathway" and in the "direct sulfhydrylation pathway", alternate pathways for the synthesis of methionine. For example, *E. coli*, utilizes a transsulfuration pathway, whereas, other microorganisms such as *Saccharomyces cerevisiae*, *C. glutamicum*, and *B. subtilis* and relatives of these microorganisms have developed a direct sulfhydrylation pathway. Although many microorganisms use either the transsulfuration pathway or the direct sulfhydrylation pathway, but not both, some microorganisms, such as for example, *C. glutamicum*, use both pathways for the synthesis of methionine.

"Methionine biosynthetic enzymes" encompass all enzymes normally found in microorganisms which contribute to the production of methionine. Table 1 lists various enzymes in the methionine biosynthetic pathway and the corresponding genes encoding them and FIG. 1 depicts a schematic representation of the methionine biosynthetic pathway. It is understood that in some microorganisms the names of the genes encoding the corresponding enzymes may vary from the names listed herein.

TABLE 1

Enzymes in the methionine biosynthetic pathway and the genes encoding them

| Enzyme | Gene |
|---|---|
| Aspartate kinase | ask |
| Homoserine Dehydrogenase | hom |
| Homoserine Acetyltransferase | metX |
| Homoserine Succinyltransferase | metA |
| Cystathionine γ-synthetase | metB |
| Cystathionine β-lyase | metC |
| O-Acetylhomoserine sulfhydrylase | metY |
| O-Succinylhomoserine sulfhydrylase | metZ |
| Vitamin $B_{12}$-dependent methionine synthase | metH |
| Vitamin $B_{12}$-independent methionine synthase | metE |
| $N^{5,10}$-methylene-tetrahydrofolate reductase | metF |
| S-adenosylmethionine synthase | metK |

According to FIG. 1, synthesis of methionine from oxaloacetate (OAA) proceeds via the intermediates, aspartate, aspartate phosphate and aspartate semialdehyde. Aspartate semialdehyde is converted to homoserine by homoserine dehydrogenase (the product of the hom gene, also known as thrA, metL, hdh, among other names in other organisms). The subsequent steps in methionine synthesis can proceed through the transsulfuration pathway and/or the direct sulfhydrylation pathway.

In the transsulfuration pathway, homoserine is converted to either O-acetylhomoserine by homoserine acetyltransferase (the product of the metX gene, sometimes also called metA) and the addition of acetyl CoA, or to O-succinylhomoserine by the addition of succinyl CoA by the product of a metA gene (homoserine succinyltransferase). Donation of a sulfur group from cysteine to either O-acetylhomoserine or O-succinylhomoserine by cystathionine γ-synthase, the product of a metB gene, produces cystathionine. Cystathionine is then converted to homocysteine by cystathionine β-lyase, the product of a metC gene (also referred to as the aecD gene in some organisms).

In the direct sulfhydrylation pathway, O-acetylhomoserine sulfhydrylase, the product of a metY gene (sometimes referred to as the metZ gene) catalyzes the direct addition of sulfide to O-acetylhomoserine to form homocysteine. Homocysteine can also be formed in the direct sulfhydrylation pathway by the direct addition of a sulfide group to O-succinylhomoserine by O-succinylhomoserine sulfhydralase, the product of a metZ gene.

Regardless of which pathway is used, the transsulfuration pathway or the direct sulfhydrylation pathway, methionine is subsequently produced from homocysteine by the addition of a methyl group by vitamin $B_{12}$-dependent methionine synthase (the product of the metH gene) or vitamin $B_{12}$-independent methionine synthase (the product of the metE gene). The methyl group of methionine is donated by methyl-tetrahydrofolate (methyl-THF), which in turn is produced by reduction of methylene-THF in a reaction catalyzed by the metF gene product.

I. Methods for Culturing Microorganisms in the Presence of Dimethyl Disulfide (DMDS) Such that Methionine is Produced and Recombinant Microorganisms for use in the Methods of the Invention In one aspect, the present invention features methods of producing methionine, comprising culturing a methionine-producing microorganism in the presence of a methyl capped sulfide compound, e.g., a sulfur and/or methyl group source, preferably, dimethyl disulfide (DMDS), such that L-methionine or a salt of L-methionine is produced. A "methionine-producing microorganism" is any microorganism capable of producing methionine, e.g., bacteria, yeast, fungus, Archaea, etc. In one embodiment, the methionine producing microorganism belongs to the genus *Corynebacterium*. In another embodiment, the methionine producing microorganism is *Corynebacterium glutamicum*. In yet another embodiment, the methionine producing microorganism is selected from the group consisting of: Gram-negative bacteria (e.g., *Escherichia coli* or related Enterobacteria), Gram-positive bacteria (e.g., *Bacillus subtilis* or related *Bacillus*), yeast (e.g., *Saccharomyces cerevisiae* or related yeast strains), and Archaea, e.g., a microorganism suitable for use in the methods of the invention. In one embodiment, the microorganism belonging to the group Enterobacteria is *Escherichia coli*. In another embodiment, the microorganism belonging to the genus *Bacillus* is *Bacillus subtilis*. In yet another embodiment, the yeast microorganism is *Saccharomyces cerevisiae* or a relative thereof.

In more than one embodiment of the invention, a microorganism of the invention is cultured in medium comprising a methyl capped sulfide compound, e.g., a sulfur and/or methyl group source, preferably dimethyl disulfide (DMDS). In one embodiment, a methyl capped sulfide compound, e.g., a sulfur and/or methyl group source, e.g., DMDS, is present in the culture medium at 0.02% or higher. In another embodiment, a methyl capped sulfide compound, e.g. a sulfur and/or methyl group source, e.g., DMDS, is present in the culture medium at 0.04% or higher. In yet another embodiment, a methyl capped sulfide compound, e.g., a sulfur and/or methyl group source, e.g., DMDS, is present in the culture medium at 0.06% or higher.

In more than one embodiment of the invention, the methyl capped sulfide compound, e.g., the sulfur and/or methyl group source, is dimethyl trisulfide, dimethyltetrasulfide, or a higher molecular weight polymer of sulfide, the ends of which are capped by methyl groups. An example of such a sulfide polymer capped by methyl groups is $H_3C—(S)_n—CH_3$, wherein n is 2-50. In one embodiment, n is 40-50. In another embodiment, n is 30-40. In another embodiment, n is 20-30. In another embodiment, n is 1-20. In another embodiment, n is 5-10. In a preferred embodiment, n is 5, 6, 7, 8, 9 or 10. In another, preferred embodiment, n is 2, 3, or 4. Other examples of sulfide containing polymers are poly(ethylene oxide sulfide), which consist of an internal ethylene oxide oligomer and disulfide linkages (see, for example, Lee et al., Biomacromolecules. 2005 January-February; 6(1):246) and poly(phenylene sulfide).

In one embodiment, the methyl capped sulfide compound, e.g. the sulfur and/or methyl group source, preferably DMDS, is provided to the culture using a slow release methyl capped sulfide delivery system, e.g. a slow release sulfur and/or methyl group delivery system, e.g., a slow release dimethyl disulfide (DMDS) delivery system. As used herein, the phrases "slow release methyl capped sulfide delivery system", "slow release sulfur and/or methyl group delivery system" and "slow release dimethyl disulfide (DMDS) delivery system" include any inert substance that can be added to, or otherwise interfaced with, culture media such that small hydrophobic organic compounds, such as a methyl capped sulfide compound, e.g., a sulfur and/or methyl group source, e.g. DMDS, can be released into the aqueous phase, such that the steady state concentration of a methyl capped sulfide compound, e.g., a sulfur and/or methyl group source, e.g., DMDS, is maintained at a sub-lethal concentration for the organism being used. A "slow release methyl capped sulfide delivery system", e.g., "a slow release sulfur and/or methyl group delivery system", e.g., "a slow release dimethyl disulfide (DMDS) delivery system", also allows the prolonged, sustained release of these compounds into solution over time at a level that is not toxic to the microorganism, and does not adversely affect the growth of a microorganism itself. In one embodiment, the slow release delivery system of a methyl capped sulfide compound, e.g., a sulfur and/or methyl group source, e.g., DMDS, is a liquid that is immiscible with water, but which dissolves a methyl capped sulfide compound, e.g., a sulfur and/or methyl group source, e.g. DMDS. In a preferred embodiment, the slow release delivery system of a methyl capped sulfide compound, e.g., a sulfur and/or methyl group source, e.g., DMDS, is a beaded macro-porous polystyrene resin, e.g., Amberlite™ XAD4. Amberlite™ XAD4 consists of insoluble beads supplied as a water wet product imbibed with sodium chloride and sodium carbonate. Prior to absorption of a methyl capped sulfide compound, e.g. a sulfur and/or methyl group source, e.g., DMDS, the Amberlite™ XAD4 is washed as recommended by the manufacturer with ethanol and water yielding a suspension in water. Following absorption of a methyl capped sulfide compound, e.g., a sulfur and/or methyl group source, e.g., DMDS, to Amberlite™ XAD4 and addition of this mixture to culture media, a methyl capped sulfide compound, e.g., a sulfur and/or methyl group source, e.g., DMDS, is released from the beads at a rate sufficient to support growth of a metF or metE, metH auxotroph. In one embodiment, the methyl capped sulfide compound, e.g., a sulfur and/or methyl group source, e.g., DMDS, is present at 0.1% or higher in the culture media containing Amberlite™ XAD4. In another embodiment, the methyl capped sulfide compound, e.g., a sulfur and/or methyl group source, e.g., DMDS, is present at 0.2% or higher in the culture media containing Amberlite™ XAD4. In yet another embodiment, the methyl capped sulfide compound, e.g., a sulfur and/or methyl group source, e.g., DMDS, is present at 0.3% or higher in the culture media containing Amberlite™ XAD4.

In another preferred embodiment, the slow release methyl capped sulfide delivery system, e.g., the slow release sulfur and/or methyl group delivery system, e.g., the DMDS slow release delivery system, is a slow controlled methyl capped sulfide compound feed, e.g., a sulfur and/or methyl group source feed, e.g., a DMDS feed. As used herein, the phrases a "slow controlled methyl capped sulfide compound feed", "a slow controlled sulfur and/or methyl group source feed, and a "slow controlled DMDS feed" is a slow controlled feed that delivers, e.g., incrementally or continuously, a methyl capped sulfide compound, e.g., a sulfur and/or methyl group source, e.g., DMDS, to the culture in sufficient quantities such that the desired product, e.g., methionine, is produced, but such that levels toxic to the production microorganism are avoided. In yet another preferred embodiment, the slow release delivery system of the invention is a membrane that is permeable to a methyl capped sulfide compound, e.g., a sulfur and/or methyl group source, e.g., DMDS, and the methyl capped sulfide compound, e.g., a sulfur and/or methyl group source, e.g., DMDS, is allowed to diffuse or flow through the membrane into the growth medium. Non-limiting examples of membranes include any membrane that can maintain structural and functional integrity in the presence of organic solvents (i.e., DMDS) and aqueous culture medium. Such membranes are described in the Millipore Corporation Catalog and technical references guide entitled "1994-1995 Millipore Direct", Millipore Corporation, Bedford, Mass., USA, hereby incorporated in its entirety by reference. Suitable membranes include those comprised of PVDF (polyvinylidene fluoride) PTFE (polytetrafluoroethylene), polypropylene, polyvinyl chloride, polyether sulfone, nylon, and polycarbonate, either with or without hydrophilic coatings. Additional, non-limiting examples of substances that can be used as a slow release dimethyl disulfide (MDS) delivery system include other beaded hydrophobic resins, animal oils, mineral oils, chemical oils, vegetable oils, synthetic oils, organic solvent, chloro-carbons, fluoro-carbons, chlorofluoro-carbons, or combinations thereof.

As described herein, microorganisms in which the methionine biosynthetic pathway has been genetically altered, e.g., to overproduce O-acetylhomoserine, results in the improved production of methionine in media containing a methyl capped sulfide compound, e.g., a sulfur and/or methyl group source, such as, for example, DMDS. Accordingly, the present invention also provides methods of producing methionine, comprising culturing a microorganism having a deregulated methionine biosynthetic pathway in the presence of a methyl capped sulfide compound, e.g., a sulfur and/or methyl group source, preferably dimethyl disulfide (DMDS), such that methionine is produced.

The methodologies of the present invention feature microorganisms, e.g., recombinant microorganisms, preferably including vectors or genes (e.g., wild-type and/or mutated genes) as described herein and/or cultured in a manner which results in the production of a desired product (e.g. methionine). The term "recombinant" microorganism includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived.

In another preferred embodiment, a recombinant microorganism is designed or engineered such that at least one non-native methionine biosynthetic enzyme is expressed or overexpressed. The term "overexpressed" or "overexpression" includes expression of a gene product (e.g., a biosynthetic enzyme) in an appropriate growth medium at a level greater than that expressed prior to manipulation of the microorganism or in a comparable microorganism which has not been manipulated. In one embodiment, the microorganism can be genetically designed or engineered to overexpress a level of gene product greater than that expressed in a comparable microorganism which has not been engineered. Preferably, the biosynthetic enzyme encoding-gene is included within a recombinant vector and/or a biosynthetic enzyme expressed from a recombinant vector. The ordinary skilled artisan will appreciate that a microorganism expressing or overexpressing a gene product produces or overproduces the gene product as a result of expression or overexpression of nucleic acid sequences and/or genes encoding the gene product.

The term "manipulated microorganism" include's a microorganism that has been engineered (e.g., genetically engineered) or modified such that the microorganism has at least one enzyme of the methionine biosynthetic pathway modified in amount or structure such that methionine production is increased. Modification or engineering of such microorganisms can be according to any methodology described herein including, but not limited to, deregulation of a biosynthetic pathway and/or overexpression of at least one biosynthetic enzyme. A "manipulated" enzyme (e.g., a "manipulated" biosynthetic enzyme) includes an enzyme, the expression, production, or activity of which has been altered or modified such that at least one upstream or downstream precursor, substrate or product of the enzyme is altered or modified (e.g., an altered or modified level, ratio, etc. of precursor, substrate and/or product), for example, as compared to a corresponding wild-type or naturally occurring enzyme. A "manipulated" enzyme also includes one where resistance to inhibition, e.g., feedback inhibition by one or more products or intermediates has been enhanced. For example, an enzyme that is capable of enzymatically functioning efficiently in the presence of, e.g. methionine.

The term "overexpressed" or "overexpression" includes expression of a gene product (e.g., a methionine biosynthetic enzyme) at a level greater than that expressed prior to manipulation of the microorganism or in a comparable microorganism which has not been manipulated. In one embodiment, the microorganism can be genetically manipulated (e.g., genetically engineered) to overexpress a level of gene product greater than that expressed prior to manipulation of the microorganism or in a comparable microorganism which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g. regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins and/or the use of mutator alleles, e.g., bacterial alleles that enhance genetic variability and accelerate, for example, adaptive evolution).

In another embodiment, the microorganism can be physically or environmentally manipulated to overexpress a level of gene product greater than that expressed prior to manipulation of the microorganism or in a comparable microorganism which has not been manipulated. For example, a microorganism can be treated with or cultured in the presence of an agent known or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

A preferred "recombinant" microorganism of the present invention is a microorganism having a deregulated methionine biosynthetic pathway or enzyme. The term "deregulated" or "deregulation" includes the alteration or modification of at least one gene in a microorganism that encodes an enzyme in a biosynthetic pathway, such that the level or activity of the biosynthetic enzyme in the microorganism is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene, e.g., 2, 3, 4, 5, 6, 7, in a given biosynthetic pathway) in a microorganism arises from the particular phenomenon of microorganisms in which more than one enzyme (e.g., 2, 3, 4, 5, 6, 7, etc., biosynthetic enzymes) are encoded by genes occurring adjacent to one another on a contiguous piece of genetic material termed an "operon".

The term "operon" includes at least two adjacent genes or ORFs, optionally overlapping in sequence at either the 5' or 3' end of at least one gene or ORF. The term "operon" includes a coordinated unit of gene expression that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of the regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant, or resistant to inhibition by a product or intermediate, or has a higher or lower specific activity.

A particularly preferred "recombinant" microorganism of the present invention has been genetically engineered to overexpress a bacterially-derived gene or gene product. The term "bacterially-derived" or "derived-from", for example bacteria, includes a gene which is naturally found in bacteria or a gene product (e.g., homoserine acetyltransferase, homoserine dehydrogenase, and O-acetylhomoserine sulfhydrylase) which is encoded by a bacterial gene (e.g. encoded by metX, hom (also known as hsd, etc.), and metY, respectively).

In one embodiment, the methionine-producing microorganism has at least one methionine biosynthetic enzyme deregulated. In a preferred embodiment the deregulated methionine biosynthetic enzyme is O-acetylhomoserine sulfhydrylase. In another embodiment, the methionine-producing microorganism has at least two methionine biosynthetic enzymes deregulated. In one preferred embodiment, the deregulated methionine biosynthetic enzymes are homoserine acetyltransferase and homoserine dehydrogenase. In another preferred embodiment, the deregulated methionine biosynthetic enzymes are O-acetyl-homoserine sulfhydrylase and homoserine acetyltransferase.

In one embodiment, the present invention features modification of various biosynthetic enzymes of the methionine biosynthetic pathway. In particular, the invention features modifying various enzymatic activities associated with said pathways by modifying or altering the genes encoding said biosynthetic enzymes.

The term "gene", as used herein, includes a nucleic acid molecule (e.g., a DNA molecule or segment thereof) that, in an organism, can be separated from another gene or other genes, by intergenic DNA (i.e., intervening or spacer DNA which naturally flanks the gene and/or separates genes in the chromosomal DNA of the organism). Alternatively, a gene may slightly overlap another gene (e.g., the 3' end of a first gene overlapping the 5' end of a second gene), the overlapping genes separated from other genes by intergenic DNA. A gene may direct synthesis of an enzyme or other protein molecule (e.g., may comprise coding sequences, for example, a contiguous open reading frame (ORF) which encodes a protein) or may itself be functional in the organism. A gene in an organism may be clustered in an operon, as defined herein, said operon being separated from other genes and/or operons by the intergenic DNA. An "isolated gene", as used herein, includes a gene which is essentially free of sequences which naturally flank the gene in the chromosomal DNA of the organism from which the gene is derived (i.e., is free of adjacent coding sequences that encode a second or distinct protein, adjacent structural sequences or the like) and optionally includes 5' and 3' regulatory sequences, for example promoter sequences and/or terminator sequences. In one embodiment, an isolated gene includes predominantly coding sequences for a protein (e.g., sequences which encode *Corynebacterium* proteins). In another embodiment, an isolated gene includes coding sequences for a protein (e.g., for a *Corynebacterium* protein) and adjacent 5' and/or 3' regulatory sequences from the chromosomal DNA of the organism from which the gene is derived (e.g., adjacent 5' and/or 3' *Corynebacterium* regulatory sequences). Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

A "gene having a mutation" or "mutant gene" as used herein, includes a gene having a nucleotide sequence which includes at least one alteration (e.g., substitution, insertion, deletion) such that the polypeptide or protein encoded by said mutant exhibits an activity that differs from the polypeptide or protein encoded by the wild-type nucleic acid molecule or gene. In one embodiment, a gene having a mutation or mutant gene encodes a polypeptide or protein having an increased activity as compared to the polypeptide or protein encoded by the wild-type gene, for example, when assayed under similar conditions (e.g., assayed in microorganisms cultured at the same temperature). As used herein, an "increased activity" or "increased enzymatic activity" is one that is at least 5% greater than that of the polypeptide or protein encoded by the wild-type nucleic acid molecule or gene, preferably at least 5-10% greater, more preferably at least 10-25% greater and even more preferably at least 25-50%, 50-75% or 75-100% greater than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, an "increased activity" or "increased enzymatic activity" can also include an activity that is at least 1.25-fold greater than the activity of the polypeptide or protein encoded by the wild-type gene, preferably at least 1.5-fold greater, more preferably at least 2-fold greater and even more preferably at least 3-fold, 4-fold, 5-fold, 10-fold, 20-fold, 50-fold, 100-fold greater than the activity of the polypeptide or protein encoded by the wild-type gene.

In another embodiment, a gene having a mutation or mutant gene encodes a polypeptide or protein having a reduced activity as compared to the polypeptide or protein encoded by the wild-type gene, for example, when assayed under similar conditions (e.g., assayed in microorganisms cultured at the same temperature). A mutant gene also can encode no polypeptide or have a reduced level of production of the wild-type polypeptide. As used herein, a "reduced activity" or "reduced enzymatic activity" is one that is at least 5% less than that of the polypeptide or protein encoded by the wild-type nucleic acid molecule or gene, preferably at least 5-10% less, more preferably at least 10-25% less and even more preferably at least 25-50%, 50-75% or 75-100% less than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, a "reduced activity" or "reduced enzymatic activity" can also include an activity that has been deleted or "knocked out" (e.g., approximately 100% less activity than that of the polypeptide or protein encoded by the wild-type nucleic acid molecule or gene).

In more than one embodiment, the microorganisms of the invention having a combination of deregulated genes produce methionine, for example, at a level which is at least 1-2% greater, or at least 3-5% greater, or at least 5-10% greater, or at least 10-20% greater, or at least 20-30% greater, or at least 30-40% greater, or at least 40-50% greater, or at least 50-60% greater, or at least 60-70% greater, or at least 70-80% greater, or at least 80-90% greater, or at least 90-95% greater than the sum of methionine levels produced in presence of each individual deregulated gene.

In some embodiments, the level of methionine produced by microorganisms including a combination of deregulated genes is at least 2-fold, or at least 2.5-fold, or at least 3-fold, or at least 3.5-fold, or at least 4-fold, or at least 4.5-fold, or at least 5-fold, or at least 10-fold, or at least 15-fold, or at least 20-fold, or at least 25-fold, or at least 30-fold, or at least 35-fold, or at least 40-fold, or at least 45-fold, or at least 50-fold, or at least 100-fold higher than the sum of levels of methionine produced in presence of each individual deregulated gene.

In yet other embodiments, amount of methionine produced by a microorganism under suitable fermentation conditions, including a combination of altered genes, is at least 5 g, or at least 7 g, or at least 8 g, or at least 9 g, or at least 10 g, or at least 11 g, or at least 12 g, or at least 13 g, or at least 14 g, or at least 15 g, or at least 16 g, or at least 17 g, or at least 18 g, or at least 19 g, or at least 20 g, or at least 25 g, or at least 30 g, or at least 40 g, or at least 50 g greater per liter relative to the sum of amounts produced by a microorganism in the presence of each individual altered gene, or in presence of no gene alterations.

The level of methionine produced by microorganisms described herein can be easily measured using one or more assays described herein.

Activity can be determined according to any well accepted assay for measuring activity of a particular protein of interest. Activity can be measured or assayed directly, for example, measuring an activity of a protein isolated or purified from a cell or microorganism. Alternatively, an activity can be measured or assayed within a cell or microorganism or in an extracellular medium. For example, assaying for a mutant gene (i.e., said mutant encoding a reduced enzymatic activity) can be accomplished by expressing the mutated gene in a microorganism, for example, a mutant microorganism in which the enzyme is a temperature-sensitive, and assaying the mutant gene for the ability to complement a temperature sensitive (Ts) mutant for enzymatic activity. A mutant gene that encodes an "increased enzymatic activity" can be one that complements the Ts mutant more effectively than, for example, a corresponding wild-type gene. A mutant gene that encodes a "reduced enzymatic activity" is one that complements the Ts mutant less effectively than, for example, a corresponding wild-type gene.

It will be appreciated by the skilled artisan that even a single substitution in a nucleic acid or gene sequence (e.g., a base substitution that encodes an amino acid change in the corresponding amino acid sequence) can dramatically affect the activity of an encoded polypeptide or protein as compared to the corresponding wild-type polypeptide or protein. A mutant gene (e.g., encoding a mutant polypeptide or protein), as defined herein, is readily distinguishable from a nucleic acid or gene encoding a protein homologue in that a mutant gene encodes a protein or polypeptide having an altered activity, optionally observable as a different or distinct phenotype in a microorganism expressing said mutant gene or producing said mutant protein or polypeptide (i.e., a mutant microorganism) as compared to a corresponding microorganism expressing the wild-type gene. By contrast, a protein homologue can have an identical or substantially similar activity, optionally phenotypically indiscernible when produced in a microorganism, as compared to a corresponding microorganism expressing the wild-type gene. Accordingly it is not, for example, the degree of sequence identity between nucleic acid molecules, genes, protein or polypeptides that serves to distinguish between homologues and mutants, rather it is the activity of the encoded protein or polypeptide that distinguishes between homologues and mutants: homologues having, for example, low (e.g., 30-50% sequence identity) sequence identity yet having substantially equivalent functional activities, and mutants, for example sharing 99% sequence identity yet having dramatically different or altered functional activities.

In one embodiment, a recombinant microorganism of the present invention is a Gram positive organism (e.g., a microorganism which retains basic dye, for example, crystal violet, due to the presence of a Gram-positive wall surrounding the microorganism). In a preferred embodiment, the recombinant microorganism of the present invention is of the genus *Corynebacterium*. In one embodiment, the recombinant microorganism is of the genus *Bacillus*. In another preferred embodiment, the recombinant microorganism is selected from the group consisting of *Bacillus licheniformis, Bacillus amyloliquefaciens, Bacillus halodurans, Bacillus subtilis,* and *Bacillus pumilus*.

In another embodiment, the recombinant microorganism is a Gram negative (excludes basic dye) organism. In another embodiment, the recombinant microorganism of the present invention is a microorganism belonging to the group Enterobacteria. In a preferred embodiment, the recombinant microorganism is a microorganism belonging to a genus selected from the group consisting of *Salmonella, Escherichia, Klebsiella, Serratia,* and *Proteus*. In a more preferred embodiment, the recombinant microorganism is of the genus *Escherichia*. In an even more preferred embodiment, the recombinant microorganism is *Escherichia coli*. In another embodiment, the recombinant microorganism is a yeast of the genus *Saccharomyces* (e.g., *S. cerevisiae*), and an Archaea An important aspect of the present invention involves culturing the microorganisms of the present invention, such that a desired compound (e.g., methionine) is produced.

The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid medium) comprising nutrients essential or beneficial to the maintenance and/or growth of the microorganism (e.g., carbon sources or carbon substrate, for example carbohydrate, hydrocarbons, oils, fats, fatty acids, organic acids, and alcohols; nitrogen sources, for example, peptone, yeast extracts, meat extracts, malt extracts, urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, nickel, molybdenum, and/or cobalt salts; as well as growth factors such as amino acids, vitamins, growth promoters and the like).

The microorganisms produced according to the invention may be cultured continuously or batchwise or in a fed batch or repeated fed batch process to produce methionine. An overview of known cultivation methods can be found in the textbook by Chmiel (*Bioprozeßtechnik 1. Einführung in die Bioverahrenstechnik* (Gustav Fischer Verlag, Stuttgart, 1991)) or in the textbook by Storhas (*Bioreaktoren und periphere Einrichtungen* (Vieweg Verlag, Braunschweig/Wiesbaden, 1994)).

Preferably, microorganisms of the present invention are cultured under controlled pH. The term "controlled pH" includes any pH which results in production of the desired product (e.g., methionine). In one embodiment microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., methionine). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the culture vessel (e.g., tube or flask) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, microorganisms of the present invention can be cultured under controlled temperatures. The term "controlled temperature" includes any temperature which results in production of the desired product (e.g., methionine). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 50° C.

Microorganisms can be cultured (e.g., maintained and/or grown) in liquid media and preferably are cultured, either continuously or intermittently, by conventional culturing methods such as standing culture, test tube culture, shaking culture. (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous processes or methods of fermentation. The phrase "batch process" or "batch fermentation" refers to a system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., methionine). Varieties of such processes have been developed and are well-known in the art.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Carbon sources that are appropriate for use in the culture medium are, for example, sugars and carbohydrates, such as e.g. glucose, sucrose, lactose, fructose, maltose, molasses, starch and cellulose, oils and fats, such as e.g., soya oil, sunflower oil, groundnut oil and coconut fat, fatty acids, such as e.g. palmitic acid, stearic acid and linoleic acid, alcohols, such as e.g., glycerol and ethanol, and organic acids, such as e.g. acetic acid. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus.

In addition to DMDS, dimethyl trisulfide, dimethyltetrasulfide, or a higher molecular weight polymer of sulfide, the ends of which are capped by methyl groups, organic and inorganic sulfur-containing compounds, such as, for example, sulfides, sulfites, sulfates and thiosulfates, can be used as additional sources of sulfur.

The culture medium may furthermore comprise salts of metals, such as e.g., magnesium sulfate or iron sulfate, which are necessary for growth. Finally, essential and non-essential growth substances, such as amino acids and vitamins, can be employed in addition to the above-mentioned substances. Suitable precursors can moreover be added to the culture medium. The staring substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The phrase "culturing under conditions such that a desired compound is produced" includes maintaining and/or growing microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a compound (e.g., methionine). Preferably, culturing is continued for a time sufficient to substantially reach suitable production of the compound (e.g., a time sufficient to reach a suitable concentration of methionine). In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In another embodiment, culturing is continued for a time sufficient to reach desirable production yields of methionine, for example, microorganisms are cultured such that at least about 7 to 10 g/L, or at least 10 to 15 g/L, or at least about 15 to 20 g/L, or at least about 20 to 25 g/L, or at least about 25 to 30 g/L, or at least about 30 to 35 g/L, or at least about 35 to 40 g/L, or at least about 40 to 50 g/L methionine is produced. In yet other embodiments, microorganisms are cultured under conditions such that a preferred yield of methionine, for example, a yield within a range set forth above, is produced in about 24 hours, in about 36 hours, in about 48 hours, in about 72 hours, or in about 96 hours.

The methodology of the present invention can further include a step of recovering a desired compound (e.g., methionine). The term "recovering" a desired compound includes concentrating, extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization, drying, evaporation, and the like. For example, methionine can be recovered from culture media by first removing the microorganisms from the culture.

Preferably, a desired compound of the present invention is "extracted", "isolated" or "purified" such that the resulting preparation is substantially free of other media components (e.g., free of media components and/or fermentation byproducts). The language "substantially free of other media components" includes preparations of the desired compound in which the compound is separated from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts).

This disclosure further encompasses biotransformation processes which feature various recombinant microorganisms described herein. The term "biotransformation process," also referred to herein as "bioconversion processes," includes biological processes which results in the production (e.g., transformation or conversion) of appropriate substrates and/or intermediate compounds into a desired product (e.g., methionine).

Microorganism(s) and/or enzymes used in biotransformation reactions are in a form that allows them to perform their intended function (e.g. producing a desired compound). Such microorganisms can be whole cells, or can be only those portions of a cell (for example genes and/or enzymes) necessary to obtain the desired end result. These microorganisms can be suspended (e.g. in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeabilized (e.g., have permeabilized membranes and/or walls such that compounds, for example, substrates, intermediates or products can more easily pass through said membrane or wall).

In an alternative embodiment, the desired compound is not purified from the microorganism, for example, when the microorganism is biologically non-hazardous (e.g., safe). For example, the entire culture (or culture supernatant) can be used as a source of product (e.g., crude product). In one embodiment, the culture (or culture supernatant) is used without modification. In another embodiment, the culture (or culture supernatant) is concentrated. In yet another embodiment, the culture (or culture supernatant) is dried or lyophilized. The product obtained by the present invention can include in addition to methionine, other components of the fermentation broth, e.g. phosphates, carbonates, remaining carbohydrates, biomass, complex media components, etc.

II. Recombinant Nucleic Acid Molecules, Vectors, and Polypeptides

The present invention further features recombinant nucleic acid molecules (e.g., recombinant DNA molecules) that include genes described herein (e.g., isolated genes), preferably *Corynebacterium* genes, more preferably *Corynebacterium glutamicum* genes, even more preferably *Corynebacterium glutamicum* methionine biosynthetic genes. The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Preferably, a recombinant nucleic acid molecule (e.g., a recombinant DNA molecule) includes an isolated gene of the present invention operably linked to regulatory sequences. The phrase "operably linked to regulatory sequence(s)" means that the nucleotide sequence of the gene of interest is linked to the regulatory sequence(s) in a manner which allows for expression (e.g., enhanced, increased, constitutive, basal, attenuated, decreased or repressed expression) of the gene, preferably expression of a gene product encoded by the gene (e.g., when the recombinant nucleic acid molecule is included in a recombinant vector, as defined herein, and is introduced into a microorganism).

The term "heterologous nucleic acid" is used herein to refer to nucleic acid sequences not typically present in a target organism. They may also comprise nucleic acid sequences present in a target organism, but not normally found in a genetic region of a target organism of interest. Similarly, the term "heterologous gene" refers to a gene not present in a wild-type isolate of the host organism. Heterologous nucleic acids and heterologous genes generally comprise recombinant nucleic acid molecules. The heterologous nucleic acid or heterologous gene may or may not comprise modifications (e.g., by addition, deletion or substitution of one or more nucleotides).

Also encompassed by this disclosure are homologs of the various genes and proteins described herein. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homolog of. Homologs of the genes described herein can be identified by percent identity between amino acid or nucleotide sequences for putative homologs and the sequences for the genes or proteins encoded by them (e.g., nucleotide sequences for *Corynebacterium glutamicum* genes ask, hom, metX, metY, metB, metH, metE, metF, metC, and metK, or their complementary strands). Percent identity may be determined, for example, by visual inspection or by using various computer programs known in the art or as described herein. For example, percent identity of two nucleotide sequences can be determined by comparing sequence information using the GAP computer program described by Devereux et al. (1984) *Nucl. Acids. Res.*, 12:387 and available from the University of Wisconsin Genetics Computer Group (UWGCG). Percent identity can also be determined by aligning two nucleotide sequences using the Basic Local Alignment Search Tool BLAST®) program as described by Tatusova et al. (1999) *FEMS Microbiol. Lett.*, 174:247. For example, for nucleotide sequence alignments using the BLAST™ program, the default settings are as follows: reward for match is 2, penalty for mismatch is −2, open gap and extension gap penalties are 5 and 2 respectively, gap-.times.dropoff is 50, expect is 10, word size is 11, and filter is OFF.

As used herein, the terms "homology" and "homologous" are not limited to designate proteins having a theoretical common genetic ancestor, but includes proteins which may be genetically unrelated that have, none the less, evolved to perform similar functions and/or have similar structures. Functional homology to the various proteins described herein also encompasses proteins that have an activity of the corresponding protein it is a homolog of. For proteins to have functional homology, it is not required that they have significant identity in their amino acid sequences, but, rather, proteins having functional homology are so defined by having similar or identical activities, e.g., enzymatic activities. Similarly, proteins with structural homology are defined as having analogous tertiary (or quaternary) structure and do not necessarily require amino acid homology or nucleic acid homology for the genes encoding them. In certain circumstances, structural homologs may include proteins which maintain structural homology only at the active site or binding site of the protein.

In addition to structural and functional homology, the present invention further encompasses proteins having at least partial amino acid identity to the various proteins and enzymes described herein. To determine the percent identity of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

In some embodiments, nucleic acid and amino acid sequences of molecules described herein comprise a nucleotide sequence or amino acid sequence which hybridizes to or is at least about 50%, 60%, 70%, 80%, 90%, 95%, 96%, 97%, 98%, 99% or more identical to a nucleic acid or amino acid sequence described herein.

The present invention also encompasses techniques well known in the art useful for the genetic engineering of the proteins described herein to produce enzymes with improved or modified characteristics. For example, it is well within the teachings available in the art to modify a protein such that the protein has increased or decreased substrate binding affinity. It also may be advantageous, and within the teachings of the art, to design a protein which has increased or decreased enzymatic rates. Particularly for multifunctional enzymes, it may be useful to differentially fine tune the various activities of a protein to perform optimally under specified circumstances. Further the ability to modulate an enzyme's sensitivity to feedback inhibition (e.g., by methionine) may be accomplished through selective change of amino acids involved in binding or coordination of methionine or other cofactors which may be involved in negative or positive feedback. Further, genetic engineering encompasses events associated with the regulation of expression at the levels of both transcription and translation. For example, when a complete or partial operon is used for cloning and expression, regulatory sequences e.g. promoter or enhancer sequences of the gene may be modified such that they yield desired levels of transcription.

A "homolog" of any of the genes described herein can also be identified by an activity of the protein encoded by the homolog. For example, such a homolog can complement a mutation in the gene which it is a homolog of.

As used herein, the term "regulatory sequence" includes nucleic acid sequences which affect (e.g., modulate or regulate) expression of other nucleic acid sequences (i.e., genes). In one embodiment, a regulatory sequence is included in a recombinant nucleic acid molecule in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule operably linked to a regulatory sequence which accompanies or is adjacent to the gene of interest in the natural organism (e.g., operably linked to "native" regulatory sequences (e.g., to the "native" promoter). Alternatively, a gene of interest can be included in a recombinant nucleic acid molecule operably linked to a regulatory sequence which accompanies or is adjacent to another (e.g. a different) gene in the natural organism. Alternatively, a gene of interest can be included in a recombinant nucleic acid molecule operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Preferred regulatory sequences include promoters, enhancers, termination signals, anti-termination signals and other expression control elements (e.g., sequences to which repressors or inducers bind and/or binding sites for transcriptional and/or translational regulatory proteins, for example, in the transcribed mRNA). Such regulatory sequences are described, for example, in Sambrook, J., Fritsh, E. F., and Maniatis, T. *Molecular Cloning. A Laboratory Manual.* 2nd, ed., Cold Spring Harbor Laboratory, Cold Spring Harbor Laboratory Press, Cold Spring Harbor, N.Y., 1989, and in Patek, M. et al, (2003) *Journal of Biotechnology* 104:311-323. Regulatory sequences include those which direct constitutive expression of a nucleotide sequence in a microorganism (e.g., constitutive promoters and strong constitutive promoters), those which direct inducible expression of a nucleotide sequence in a microorganism (e.g., inducible promoters, for example, xylose inducible promoters) and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule of the present invention includes a nucleic acid sequence or gene that encodes at least one bacterial gene product (e.g., A methionine biosynthetic enzyme) operably linked to a promoter or promoter sequence. Preferred promoters of the present invention include *Corynebacterium* promoters and/or bacteriophage promoters (e.g., bacteriophage which infect *Corynebacterium*). In one embodiment, a promoter is a *Corynebacterium* promoter, preferably a strong, *Corynebacterium* promoter (e.g. a promoter associated with a biochemical housekeeping gene in *Corynebacterium*). In another embodiment, a promoter is a bacteriophage promoter. Additional preferred promoters, for example, for use in Gram positive microorganisms include, but are not limited to, superoxide dismutase, groEL, elongation factor Tu, amy and SPO1 promoters. Additional preferred promoters, for example, for use in Gram negative microorganisms include, but are not limited to, cos, tac, trp, tet, trp-tet, lpp, lac, lpp-lac, lacIQ, T7, T5, T3, gal, trc, ara, SP6, λ-PR or λ-PL.

In another embodiment, a recombinant nucleic acid molecule of the present invention includes a terminator sequence or terminator sequences (e.g., transcription terminator sequences). The term "terminator sequences" includes regulatory sequences that serve to terminate transcription of mRNA. Terminator sequences (or tandem transcription terminators) can further serve to stabilize mRNA (e.g., by adding structure to mRNA), for example, against nucleases.

In yet another embodiment, a recombinant nucleic acid molecule of the present invention includes sequences that allow for detection of the vector containing said sequences (i.e., detectable and/or selectable markers), for example, genes that encode antibiotic resistance sequences or that overcome auxotrophic mutations, for example, trpC, drug markers, fluorescent markers, and/or colorimetric markers (e.g., lacZ/β-galactosidase). In yet another embodiment, a recombinant nucleic acid molecule of the present invention includes an artificial ribosome binding site (RBS) or a sequence that gets transcribed into an artificial RBS. The term "artificial ribosome binding site (RBS)" includes a site within an mRNA molecule (e.g. coded within DNA) to which a ribosome binds (e.g., to initiate translation) which differs from a native RBS (e.g., a RBS found in a naturally-occurring gene) by at least one nucleotide. Preferred artificial RBSs include about 5-6, 7-8, 9-10, 11-12, 13-14, 15-16, 17-18, 19-20, 21-22, 23-24, 25-26, 27-28, 29-30 or more nucleotides of which about 1-2, 3-4, 5-6, 7-8, 9-10, 11-12, 13-15 or more differ from the native RBS (e.g., the native RBS of a gene of interest.

The present invention further features vectors (e.g., recombinant vectors) that include nucleic acid molecules (e.g., genes or recombinant nucleic acid molecules comprising said genes) as described herein. The term "recombinant vector" includes a vector (e.g., plasmid, phage, phagemid, virus, cosmid, or other purified nucleic acid vector) that has been altered, modified or engineered such that it contains greater, fewer or different nucleic acid sequences than those included in the native or natural nucleic acid molecule from which the recombinant vector was derived. Preferably, the recombinant vector includes a biosynthetic enzyme-encoding gene or recombinant nucleic acid molecule including said gene, operably linked to regulatory sequences, for example, promoter sequences, terminator sequences and/or artificial ribosome binding sites (RBSs), as defined herein. In another embodiment, a recombinant vector of the present invention includes sequences that enhance replication in bacteria (e.g., replication-enhancing sequences). In one embodiment, replication-enhancing sequences function in *E. coli* or *C. glutamicum*. In another embodiment, replication-enhancing sequences are derived from pBR322.

In yet another embodiment, a recombinant vector of the present invention includes antibiotic resistance sequences. The term "antibiotic resistance sequences" includes sequences which promote or confer resistance to antibiotics on the host organism (e.g., *Corynebacterium*). In one embodiment, the antibiotic resistance sequences are selected from the group consisting of cat (chloramphenicol resistance) sequences, tet (tetracycline resistance) sequences, erm (erythromycin resistance) sequences, neo (neomycin resistance) sequences, kan (kanamycin resistance) sequences and spec (spectinomycin resistance) sequences. Recombinant vectors of the present invention can further include homologous recombination sequences (e.g., sequences designed to allow recombination of the gene of interest into the chromosome of the host organism). It will further be appreciated by one of skill in the art that the design of a vector can be tailored depending on such factors as the choice of microorganism to be genetically engineered, the level of expression of gene product desired and the like.

It will further be appreciated by one of skill in the art that the design of a vector can be tailored depending on such factors as the choice of microorganism to be genetically engineered, the level of expression of gene product desired and the like.

"Campbell in," as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point. The name comes from Professor Alan Campbell, who first proposed this kind of recombination.

"Campbell out," as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above).

A "Campbell out" cell or strain is usually, but not necessarily, obtained by a counter-selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA Moreover, the first homologous DNA sequence and the second homologous DNA sequence are usually separated by a region of partial non-homology, and it is this region of non-homology that remains deposited in a chromosome of the "Campbell out" cell.

For practicality, in *C. glutamicum*, typical first and second homologous DNA sequence are at least about 200 base pairs in length, and can be up to several thousand base pairs in length, however, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

This invention is further illustrated by the following examples which should not be construed as limiting. The contents of all references, patents and published patent applications cited throughout this application are incorporated herein by reference.

EXAMPLES

Example 1

Generation of the M2014 Strain

Figure 2:
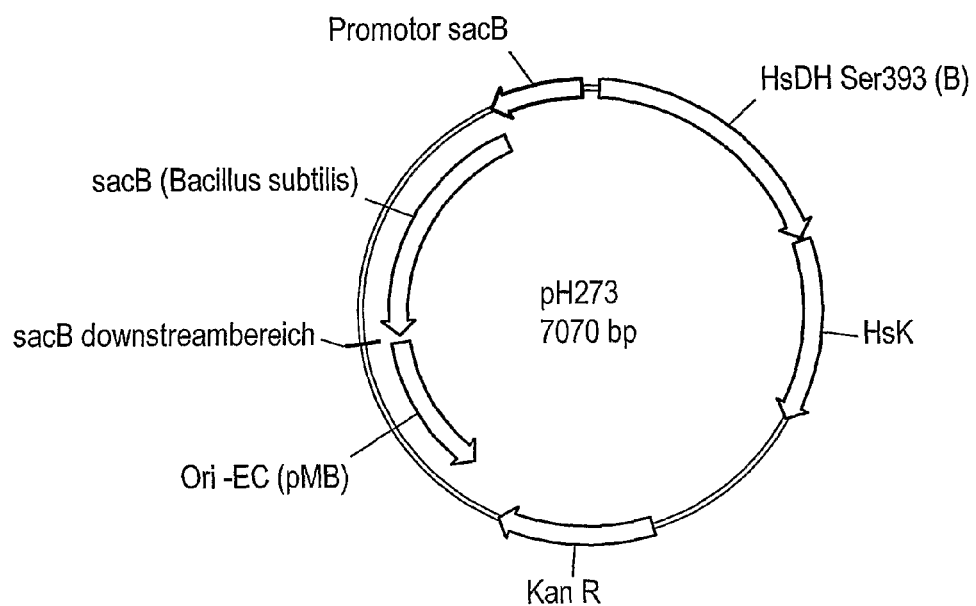
FIG. 2 is a schematic of the pH273 vector.

*C. glutamicum* strain ATCC 13032 was transformed with DNA A (also referred to as pH273) (SEQ ID NO: 1) and "Campbelled in" to yield a "Campbell in" strain. FIG. 2 shows a schematic of plasmid pH273. The "Campbell in" strain was then "Campbelled out" to yield a "Campbell out" strain, M440, which contains a gene encoding a feedback resistant homoserine dehydrogenase enzyme (hom$^{fbr}$). The resultant homoserine dehydrogenase protein included an amino acid change where S393 was changed to F393 (referred to as Hsdh S393F).

Figure 3:
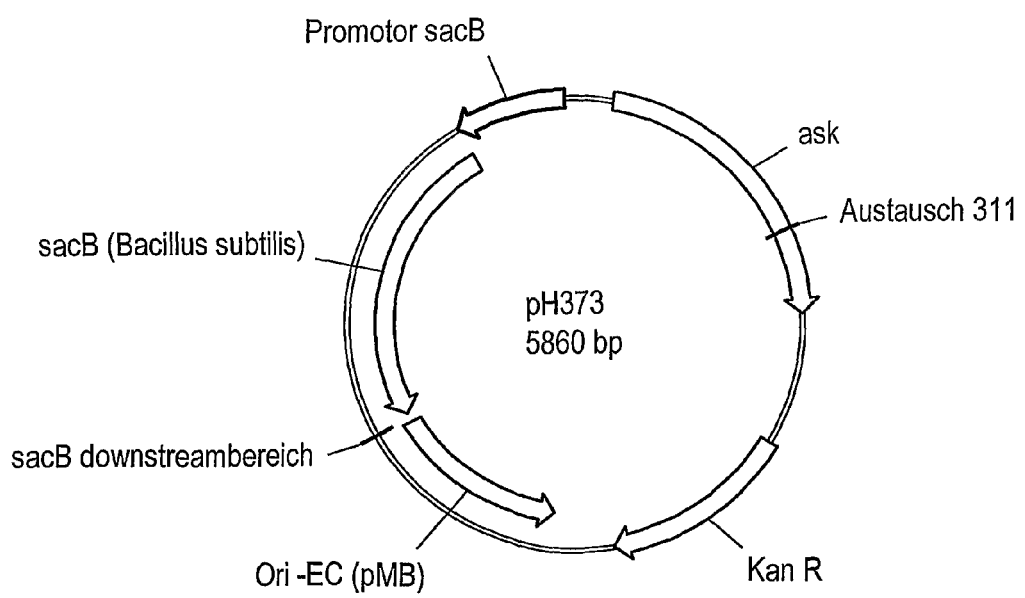
FIG. 3 is a schematic of the pH373 vector.

The strain M440 was subsequently transformed with DNA B (also referred to as pH373) (SEQ ID NO:2) to yield a "Campbell in" strain. FIG. 3 depicts a schematic of plasmid pH373. The "Campbell in" strain was then "Campbelled out" to yield a "Campbell out" strain, M603, which contains a gene encoding a feedback resistant aspartate kinase enzyme (Ask$^{fbr}$) (encoded by lysC). In the resulting aspartate kinase protein, T311 was changed to I311 (referred to as LysC T311I).

It was found that the strain M603 produced about 17.4 mM lysine, while the ATCC13032 strain produced no measurable amount of lysine. Additionally, the M603 strain produced about 0.5 mM homoserine, compared to no measurable amount produced by the ATCC13032 strain, as summarized in Table 2.

TABLE 2

Amounts of homoserine, O-acetyl homoserine, methionine and lysine produced by strains ATCC13032 and M603

| Strain | Homoserine (mM) | O-acetyl homoserine (mM) | Methionine (mM) | Lysine (mM) |
|---|---|---|---|---|
| ATCC13032 | 0.0 | 0.4 | 0.0 | 0.0 |
| M603 | 0.5 | 0.7 | 0.0 | 17.4 |

Figure 4:
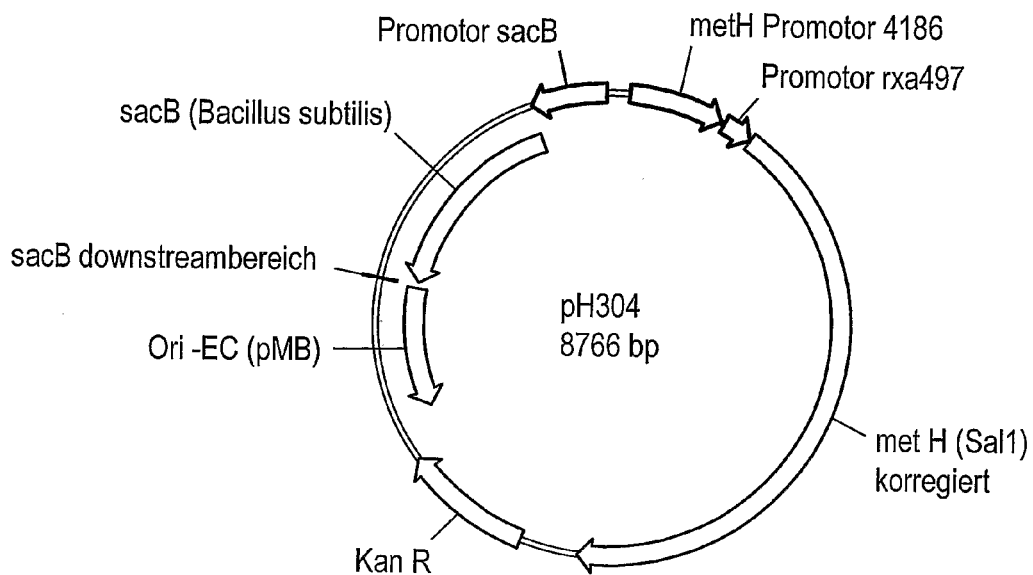
FIG. 4 is a schematic of the pH304 vector.

The strain M603 was transformed with DNA C (also referred to as pH304, a schematic of which is depicted in FIG. 4) (SEQ ID NO:3) to yield a "Campbell in" strain, which was then "Campbelled out" to yield a "Campbell out" strain, M690. The M690 strain contained a PgroES promoter upstream of the metH gene (referred to as $P_{497}$ metH) (the nucleic acid sequence of $P_{497}$ is set forth in SEQ ID NO:12) The M690 strain produced about 77.2 mM lysine and about 41.6 mM homoserine, as shown below in Table 3.

TABLE 3

Amounts of homoserine, O-acetyl homoserine, methionine and lysine produced by the strains M603 and M690

| Strain | Homoserine (mM) | O-acetyl homoserine (mM) | Methionine (mM) | Lysine (mM) |
|---|---|---|---|---|
| M603 | 0.5 | 0.7 | 0.0 | 17.4 |
| M690 | 41.6 | 0.0 | 0.0 | 77.2 |

The M690 strain was subsequently mutagenized as follows: an overnight culture of M603, grown in BHI medium (BECTON DICKINSON), was washed in 50 mM citrate buffer pH 5.5, treated for 20 min at 30° C. with N-methyl-N-nitrosoguanidine (10 mg/ml in 50 mM citrate pH 5.5). After treatment, the cells were again washed in 50 mM citrate buffer pH 5.5 and plated on a medium containing the following ingredients: (all mentioned amounts are calculated for 500 ml medium) 10 g $(NH_4)_2SO_4$; 0.5 g $KH_2PO_4$; 0.5 g $K_2HPO_4$; 0.125 g $MgSO_4 \cdot 7H_2O$; 21 g MOPS; 50 mg $CaCl_2$; 15 mg protocatechuic acid; 0.5 mg biotin; 1 mg thiamine; and 5 g/l D,L-ethionine (SIGMA CHEMICALS, CATALOG #E5139), adjusted to pH 7.0 with KOH. In addition the medium contained 0.5 ml of a trace metal solution composed of: 10 g/l $FeSO_4 \cdot 7H_2O$; 1 g/l $MnSO_4 \cdot H_2O$; 0.1 g/l $ZnSO_4 \cdot 7H_2O$; 0.02 g/l $CuSO_4$; and 0.002 g/l $NiCl_2 \cdot 6H_2O$, all dissolved in 0.1 M HCl. The final medium was sterilized by filtration and to the medium, 40 mls of sterile 50% glucose solution (40 ml) and sterile agar to a final concentration of 1.5% were added. The final agar containing medium was poured to agar plates and was labeled as minimal-ethionine medium. The mutagenized strains were spread on the plates (minimal-ethionine) and incubated for 3-7 days at 30° C. Clones that grew on the medium were isolated and restreaked on the same minimal-ethionine medium. Several clones were selected for methionine production analysis.

Methionine production was analyzed as follows. Strains were grown on CM-agar medium for two days at 30° C., which contained: 10 g/l D-glucose, 2.5 μl NaCl; 2 g/l urea; 10 g/l Bacto Peptone (DIFCO); 5 g/l Yeast Extract (DIFCO); 5 g/l Beef Extract (DIFCO); 22 g/l Agar (DIFCO); and which was autoclaved for 20 min at about 121° C.

After the strains were grown, cells were scraped off and resuspended in 0.15 M NaCl. For the main culture, a suspension of scraped cells was added at a starting OD of 600 nm to about 1.5 to 10 ml of Medium II (see below) together with 0.5 g solid and autoclaved $CaCO_3$ (REDEL DE HAEN) and the cells were incubated in a 100 ml shake flask without baffles for 72 h on a orbital shaking platform at about 200 rpm at 30° C. Medium II contained: 40 g/l sucrose; 60 g/l total sugar from molasses (calculated for the sugar content); 10 g/l $M)_2SO_4$; 0.4 g/l $MgSO_4 \cdot 7H_2O$; 0.6 g/l $KH_2PO_4$; 0.3 mg/l thiamine*HCl; 1 mg/l biotin; 2 mg/l $FeSO_4$; and 2 mg/l $MnSO_4$. The medium was adjusted to pH 7.8 with $NH_4OH$ and autoclaved at about 121° C. for about 20 min). After autoclaving and cooling, vitamin $B_{12}$ (cyanocobalamin) (SIGMA CHEMICALS) was added from a filter sterile stock solution (200 μg/ml) to a final concentration of 100 μg/l.

Samples were taken from the medium and assayed for amino acid content. Amino acids produced, including methionine, were determined using the Agilent amino acid method on an Agilent 1100 Series LC System HPLC. (AGILENT). A pre-column derivatization of the sample with ortho-phthalaldehyde allowed the quantification of produced amino acids after separation on a Hypersil AA-column (AGILENT).

Clones that showed a methionine titer that was at least twice that in M690 were isolated. One such clone, used in further experiments, was named M1179 and was deposited on May 18, 2005, at the DSMZ strain collection as strain number DSM 17322. Amino acid production by this strain was compared to that by the strain M690, as summarized below in Table 4.

TABLE 4

Amounts of homoserine, O-acetylhomoserine, methionine and lysine produced by strains M690 and M1197

| Strain | Homoserine (mM) | O-acetyl-homoserine (mM) | Methionine (mM) | Lysine (mM) |
|---|---|---|---|---|
| M690 | 41.6 | 0.0 | 0.0 | 77.2 |
| M1179 | 26.4 | 1.9 | 0.7 | 79.2 |

Figure 5:
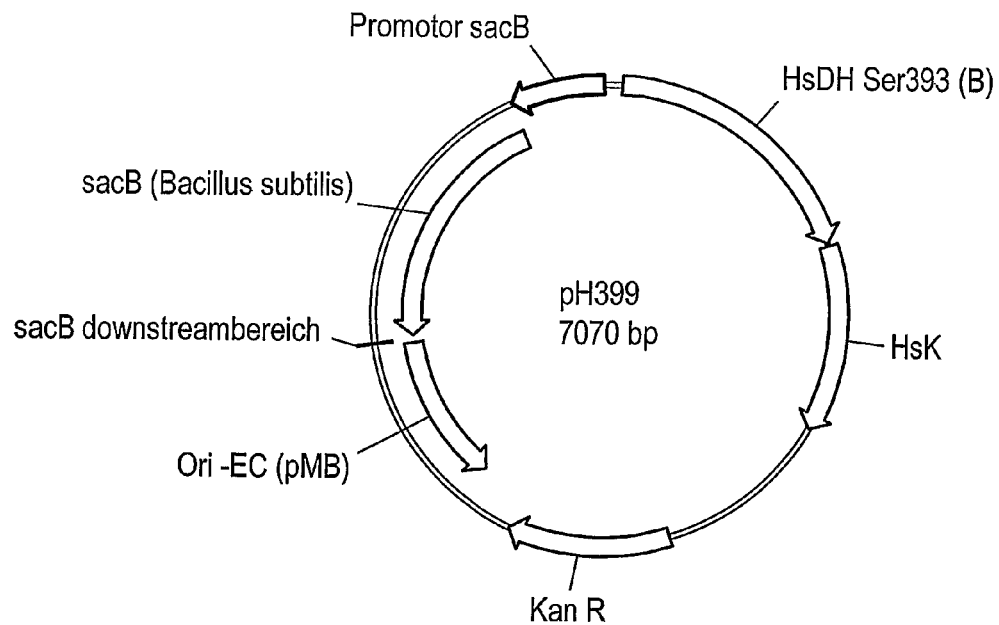
FIG. 5 is a schematic of the pH399 vector.

The strain M1179 was transformed with DNA F (also referred to as pH399, a schematic of which is depicted in FIG. 5) (SEQ ID NO: 4) to yield a "Campbell in" strain, which was subsequently "Campbelled out" to yield strain M1494. This strain contains a mutation in the gene for the homoserine kinase, which results in an amino acid change in the resulting homoserine kinase enzyme from T190 to A190 (referred to as HskT190A). Amino acid production by the strain M1494 was compared to the production by strain M1197, as summarized below in Table 5.

TABLE 5

Amounts of homoserine, O-acetylhomoserine, methionine and lysine produced by strains LU11197 and M1494

| Strain | Homoserine (mM) | O-acetyl-homoserine (mM) | Methionine (mM) | Lysine (mM) |
|---|---|---|---|---|
| M1179 | 26.4 | 1.9 | 0.7 | 79.2 |
| M1494 | 18.3 | 0.2 | 2.5 | 50.1 |

Figure 6:
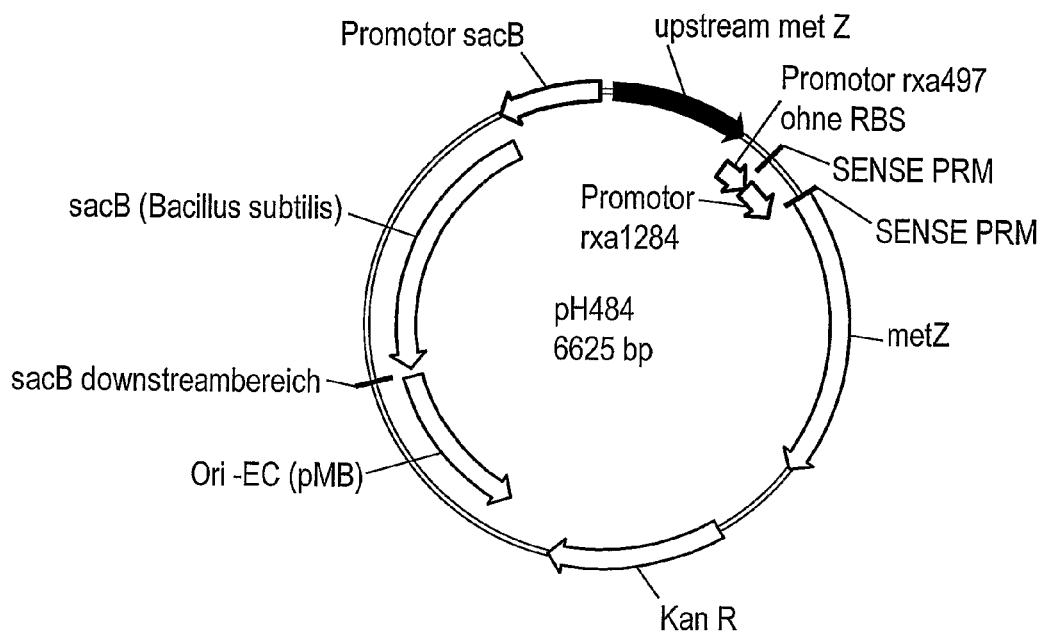
FIG. 6 is a schematic of the pH484 vector.

The strain M1494 was transformed with DNA D (also referred to as pH484, a schematic of which is shown in FIG. 6) (SEQ ID NO: 5) to yield a "Campbell in" strain, which was subsequently "Campbelled out" to yield the M1990 strain.

The M1990 strain overexpresses a metY allele using both a groES-promoter and an EFTU (elongation factor Tu)-promoter (referred to as $P_{497} P_{1284}$ metY) (the sequence of $P_{497} P_{1284}$ is shown in SEQ ID NO: 6). Amino acid production by the strain M1494 was compared to the production by strain M1990, as summarized below in Table 6.

TABLE 6

Amounts of homoserine, O-acetylhomoserine, methionine and lysine produced by strains M1494 and M1990

| Strain | Homoserine (mM) | O-acetyl-homoserine (mM) | Methionine (mM) | Lysine (mM) |
|---|---|---|---|---|
| M1494 | 18.3 | 0.2 | 2.5 | 50.1 |
| M1990 | 18.2 | 0.3 | 5.6 | 48.9 |

Figure 7:
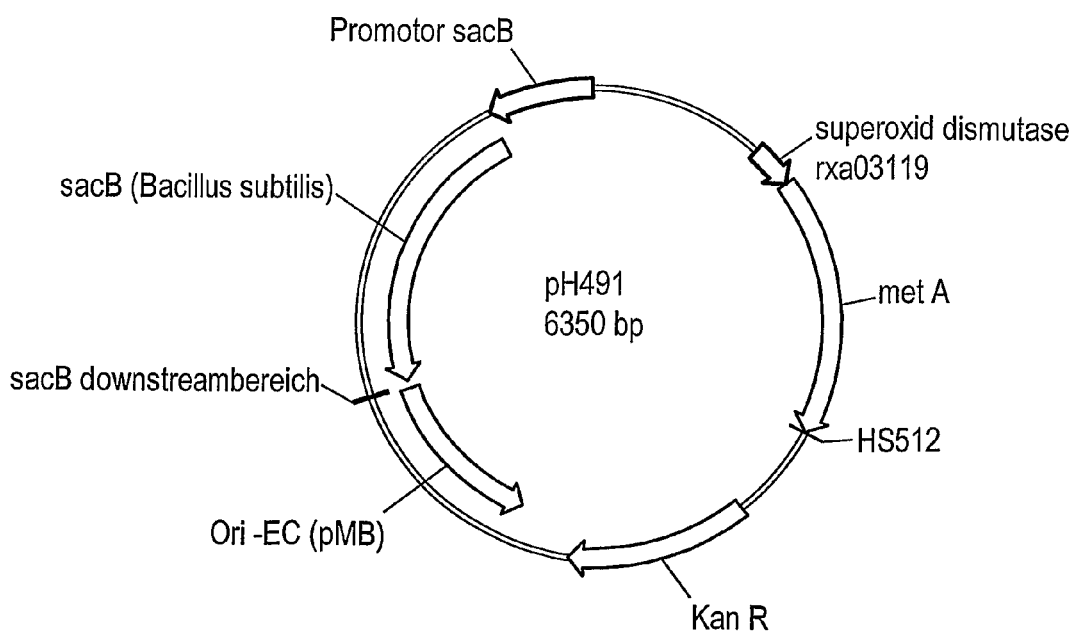
FIG. 7 is a schematic of the pH491 vector.

The strain M1990 was transformed with DNA E (also referred to as pH 491, a schematic of which is depicted in FIG. 7) (SEQ ID NO: 7) to yield a "Campbell in" strain, which was then "Campbelled out" to yield a "Campbell out" strain M2014. The M2014 strain overexpresses a metA allele using a superoxide dismutase promoter (referred to as $P_{3119}$ metA).

methionine, test tube cultures of OM63 and the parent M2014 were assayed for growth by measuring OD at 600 nm. The cultures were grown in Methionine-free medium (for recipe, see below), methionine-free medium supplemented with methionine, or methionine-free medium supplemented with various different amounts of DMDS (Aldrich Catalog No. 32,041-2). This experiment was designed to determine whether DMDS can cross the membrane of the bacterium, become reduced once inside the cytoplasm to methane thiol, and be subsequently utilized by either MetY or MetB, or another enzyme, for example MetC, as a substrate in conjunction with O-acetyl-homoserine to form methionine directly. This experiment was also designed to determine the toxicity of DMDS, if any, on cell growth.

As shown in Table 8, the *C. glutamicum* metF auxotrophs can utilize DMDS as a substrate for growth, and therefore for methionine production. In addition, the optical densities were similar for all strains in test tubes containing 5 ml of methionine-free medium supplemented with 0.02%, 0.04%, or 0.06% DMDS. Test tubes containing 5 ml of methionine-free medium supplemented with either 0.08% or 0.1% DMDS had little or no growth, presumably due to toxicity of DMDS at these concentrations. Lastly, as expected, methionine-free medium without DMDS supported growth of M2014 but not OM63.

TABLE 8

Optical densities at 600 nm of *C. glutamicum* test tube cultures[1] grown in methionine free medium with or without supplemented methionine or dimethyl disulfide (DMDS) for 36 hours at 30° C.

| Strain | Genotype | Met Free[2] (MF) | MF + Met[3] | MF + 0.02% DMDS | MF + 0.04% DMDS | MF + 0.06% DMDS | MF + 0.08% DMDS | MF + 0.1% DMDS |
|---|---|---|---|---|---|---|---|---|
| M2014 | Parent | 5.6 | 5.8 | 5.5 | 5.3 | 6.6 | 0.0 | 0.0 |
| OM63 | ΔmetF | 0.0 | 5.2 | 5.4 | 5.9 | 5.2 | 0.2 | 0.0 |

[1] Test tube cultures were securely wrapped with parafilm around the metal cap.
[2] Methionine-free medium supplemented
[3] Met free supplemented with 40 mg/l methionine.

Amino acid production by the strain M2014 was compared to the production by strain M2014, as summarized below in Table 7.

TABLE 7

Amounts of homoserine, O-acetylhomoserine, methionine and lysine produced by strains M1494 and M1990

| Strain | Homoserine (mM) | O-acetyl-homoserine (mM) | Methionine (mM) | Lysine (mM) |
|---|---|---|---|---|
| M1990 | 18.2 | 0.3 | 5.6 | 48.9 |
| M2014 | 12.3 | 1.2 | 5.7 | 49.2 |

Example 2

Figure 9:
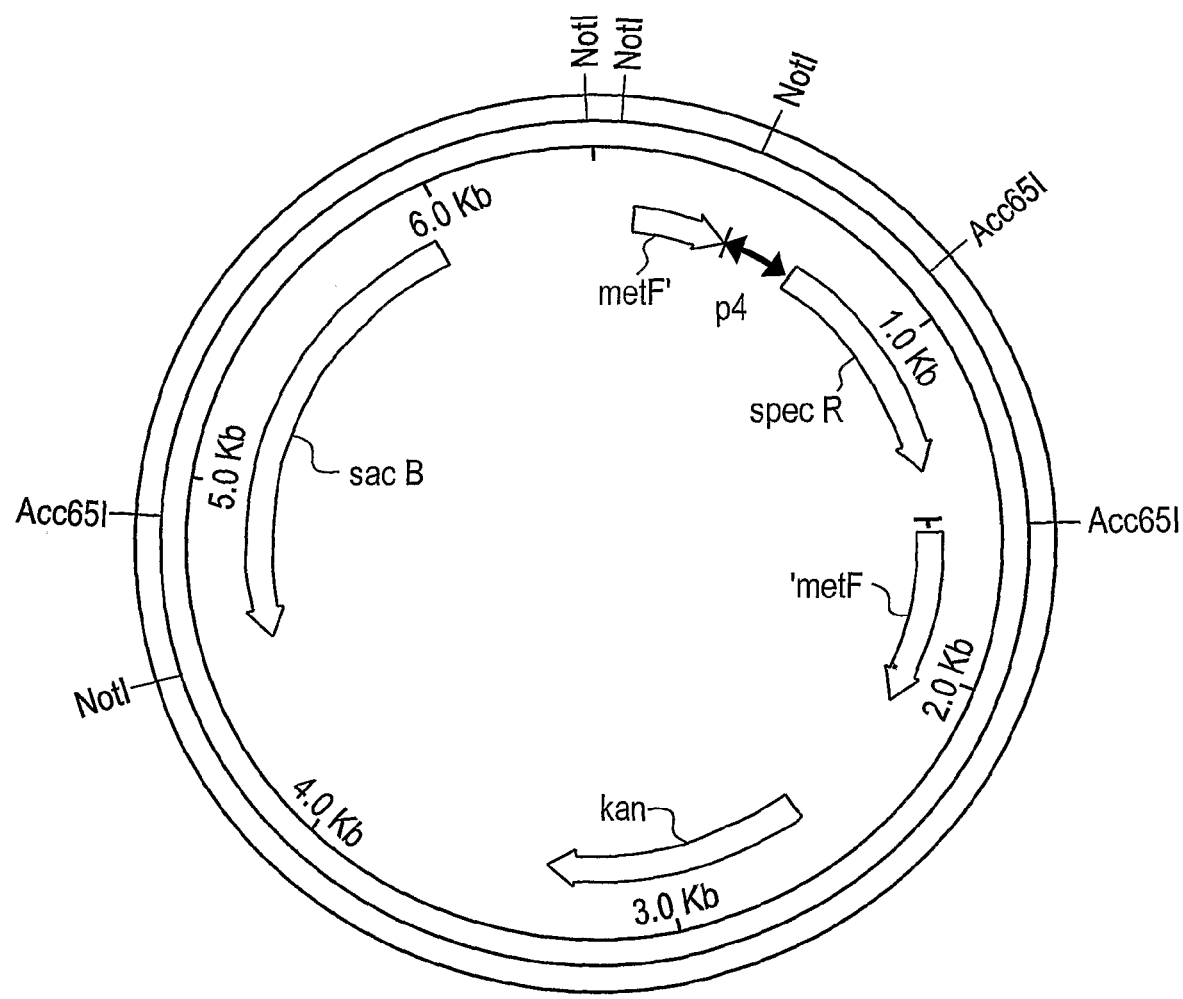
FIG. 9 is a schematic of the vector pOM86, a plasmid designed to disrupt the *C. glutamicum* metF gene with a spectinomycin resistance cassette.

*C. glutamicum* Methionine Auxotrophs Incorporate Dimethyl Disulfide into Methionine In order to determine whether *C. glutamicum* has the ability to incorporate DMDS into methionine, a deletion of metF in strain M2014 (described in Example 1) was constructed. M2014 was transformed with plasmid pOM86 (FIG. 9) (SEQ ID NO:8) to yield a "Campbell in" strain. The "Campbell in" strain was then "Cambelled out" to yield a "Campbell out" strain named OM63. To determine whether this methionine auxotroph, OM63, could utilize DMDS to synthesize The results of this experiment show that DMDS can be taken up and reductively cleaved into methane thiol by C glutamicum and enter the methionine pathway to support growth of a methionine auxotroph. Alternatively, DMDS is a direct substrate for O-acetyl-homoserine sulfhydrylase or O—O-succinyl-homoserine sulfhydrylase or another enzyme. In other words, it is possible that a single enzyme might catalyze the reductive cleavage and incorporation of DMDS into methionine.

Methionine-Free Medium—1 Liter
100 ml of Difco™ Methionine Assay Medium (105 g/l)
100 ml of 10× Spizizen's salts*
6 ml Glucose (50%)
4 ml of "4B" solution**
100 mg threonine
40 mg cysteine
785 ml $dH_2O$
5 ml 2% $CaCl_2$
**4B Solution
thiamine ($B_1$)—0.25 mg/ml cyanocolbalamin ($B_{12}$)—50 μg/ml
biotin—281 g/ml in 50 mM $KPO_4$ pH=7.0
pyridoxine HCl—1.25 mg/ml
10× Spizizen's Salts*
20 g/l Ammonium sulfate
174 g/l Potassium phosphate dibasic (trihydrate)
60 g/l Potassium phosphate monobasic (anhydrous)
10 g/l Sodium citrate 2 g/l Magnesium sulfate (heptahydrate)
After autoclaving add 3.5 ml 0.4% $FeCl_3*6H20$ and
1 ml Micronutrient solution[1]
[1]Micronutrient Solution—1 liter
0.15 g $Na_2MoO_4.2H_2O$
2.5 g $H_3BO_3$
0.7 g $CuSO_4.5H_2O$
1.6 g $MnCl_2.4H_2O$
0.3 g $ZnSO_4.7H_2O$ A solid version of this medium can be made by including about 15 to 20 g/L of agar. This is accomplished by standard procedures, such as adding 20 g agar to about 750 ml water, autoclaving, and while still melted, adding the above listed ingredients as sterile stock solutions.

Example 3

Development of a Delivery System of DMDS to *C. glutamicum* for Incorporation into Methionine As discussed above, DMDS is toxic if added directly to liquid cultures at amounts greater than about 0.06%. In order to overcome this problem, a delivery system that would allow the slow release of DMDS into solution over time was sought. Amberlite™ XAD4, a beaded macro-porous polystyrene resin, referred to hereafter as "XAD4", was chosen as a delivery system because it is inert, able to adsorb small hydrophobic organic compounds, is capable of being wetted by water, and has a high surface area and small pore size.

A test tube experiment was performed in order to determine the maximal amount of DMDS that can be adsorbed by XAD4 and still allow growth. To this end, test tube experiments using 5 ml of medium were performed on OM63 and M2014. Each test tube contained 100 µl of a 50% suspension (v/v) of XAD4 and either methionine-free medium, methionine-free medium supplemented with methionine, or methionine-free medium supplemented with various amounts of DMDS.

Test tube assays were prepared by adding 5 ml of methionine-free medium to sterile 20 mM×20 mM×150 mM test tubes covered with loose fitting metal caps. To each test tube 100 µl of a sterile suspension of XAD4 in water (50% v/v) was added. The test tubes were inoculated with cells that were grown overnight in test tubes containing BHI medium (Bacto™ Brain Heart Infusion (Becton, Dickinson and Company, Sparks, Md.) and then spun and rinsed two times with methionine-free medium. Cells were resuspended in 50% of the starting volume in methionine-free medium. The cell suspension (5 µl) was used as the inoculum for each test tube. After cell inoculation DMDS was added to each test tube at the concentration indicated (v/v). The test tubes were incubated at 30° C. at 200 rpm in a platform shaker for 24-48 hours. Cell growth was measured by optical density at 600 nm employing a Genesys™ 2 spectrophotometer.

As shown in Table 9, the optical densities were fairly similar for all strains in test tubes containing methionine-free medium supplemented with 0.1%, 0.2%, 0.3% or 0.4% DMDS. Test tubes supplemented with 0.5% DMDS showed a negative effect on OM63 growth, however, this level of DMDS seemed tolerated by M2014. In conclusion, adsorbing the DMDS onto XAD4 beads allows more DMDS to be added to liquid test tube cultures of *C. glutamicum*. Enough DMDS is released from the beads to allow for full growth of a methionine auxotroph.

TABLE 9

Optical densities at 600 nm of OM63 and M2014 grown in methionine free medium[1] with or without the indicated amounts of DMDS in the presence of XAD4[2] for 42 hours at 30° C.

| Strain | DMDS 0% | DMDS 0.1% | DMDS 0.2% | DMDS 0.3% | DMDS 0.4% | DMDS 0.5% | Met 40 mg/l |
|---|---|---|---|---|---|---|---|
| OM63 | 0.0 | 6.3 | 6.5 | 4.9 | 3.6 | 1.6 | 4.4 |
| M2014 | 6.4 | 6.6 | 6.9 | 7.3 | 7.3 | 5.5 | 7.1 |

[1]Methionine-free medium
[2]Each test tube contains 5 ml medium plus 100 µl of a 50% suspension of Amberlite XAD4. Porosity = 0.5 ml/ml.
DMDS was added after the test tubes were inoculated.
Inoculum- Cells were grown overnight in test tubes containing BHI and then spun and rinsed 2x with Met free medium. Cells were resuspended in 50% of the starting volume. The cell suspension (5 µl) of was used as the inoculum for each test tube.

Furthermore, XAD4 alone has no apparent adverse effect on cell growth. Test tubes containing methionine-free medium without DMDS supported growth of M2014, but not OM63, as expected. Test tubes containing methionine-free medium supplemented with 40 mg/l methionine, but without DMDS, resulted in a similar final optical density for M2014, but somewhat lower optical density than expected for OM63. This may be due to the XAD4 adsorbing some of the supplemented methionine, thus limiting OM63 cell growth.

Example 4

DMDS in the Gaseous State can Support Methionine Synthesis and Growth of OM101 (ΔmetB,ΔmetF)

It had been shown previously that an analog of DMDS, dimethyldiselenide (DMDSe), is toxic to microorganisms in a gaseous state but could be used to select for mutants that lacked O-acetylhomoserine sulfhydrylase (Brzywczy, J., and Paszewski, A. (1994) *Yeast* 9:1335-1342 and Treichler, H. J., et al. (1978) in FEMS Symposium No. 5, pp 177-199, R. Hutter et al, eds, Academic Press, New York). The DMDSe was introduced as a drop on the underside of the cover of a Petri plate to give a final concentration of about 5 µM, if the entire supply of DMDSe diffused into and dissolved in the agar. However, the compound DMDS was not mentioned, and it was not obvious whether diffusion through a gaseous state could supply sufficient levels of DMDS for growth (as opposed to analog inhibition). For comparison, in the liquid growth experiments of Examples 1-3 above, the concentration of DMDS was about 10 mM (for example in the case of 0.1%) or about 2000 fold higher than the DMDSe in the above cited references. However, delivery of DMDS in the gaseous state might circumvent the toxicity that was seen with liquid DMDS.

To test this possibility, lawns containing about $10^8$ cells of OM101 (ΔmetB,ΔmetF) were rinsed to be relatively free of methionine were plated on methionine-free agar plates containing about 25 ml of agar medium. DMDS was delivered either by spotting 50 µl on the center of the plate or by cutting a well in the agar at the center of the plate, and placing 50 µl of DMDS in the well. If the DMDS diffused throughout the plate, the final concentration would be about 25 mM. Control plates received the lawn of cells, but no DMDS. The plates were placed together in a sealed polypropylene plastic box that was slightly bigger than the stack of plates and incubated at 30° C. for 48-60 hours. The plates spotted with DMDS directly on the lawn had a killing zone of approximately 30 mm from where the liquid DMDS was spotted, but the remainder of the plate was covered evenly with a lawn of growth. Plates that contained liquid DMDS placed into a well had no killing zone, but rather a lawn of growth that evenly covered the entire plate, including the periphery of the plate and right up to the center well. Normally, when a required nutrient is placed in the middle of a lawn that is auxotrophic for the nutrient, a gradient of growth is seen, with the most rapid growth occurring closest to the nutrient. Finally, control plates without added DMDS, but placed in the same sealed plastic box with plates that received DMDS, gave complete lawns of growth of OM101. These observations suggested that growth of the C. glutamicum auxotrophs could be supported by diffusion of DMDS in the gas state.

In order to prove gaseous transfer, an experiment was performed where circular (25×25×5 mm) holes were cut from the center of the agar of methionine-free plates previously spread with a lawn of OM101. In these holes was placed sterile red polypropylene screw caps ((20×20×5 mm) from Sarstedt© (No. 62.554.002)) conical tubes, which served as cups for 50 µl of liquid DMDS. This method ensured that liquid DMDS did not come in direct contact with the cells and could only reach the cells by diffusion through a gaseous state, since DMDS does not quickly diffuse through polypropylene. The plates were incubated at 30° C. enclosed in an airtight plastic box. The control plates for this experiment were methionine-free plates spread with a lawn of OM101 and incubated at 30° C. in the absence of DMDS in a separate closed plastic box. After two days it was observed that a complete bacterial lawn covered the plates that had the sterile cap containing liquid DMDS and that the control plates, lacking DMDS, in a separate container, showed no growth. These experiments, taken together, indicate that direct contact of liquid DMDS is necessary for toxicity to OM101 and that, in contrast, DMDS in the gas state is not toxic but can still be utilized by OM101 for growth, and therefore, methionine synthesis. Thus, in a fermentation tank, DMDS could be delivered to the cells in a gaseous state in order to circumvent DMDS toxicity to cells in the liquid state. This could be accomplished by evaporating or boiling DMDS and pumping the DMDS vapor into the fermentation vessel, or by bubbling air or oxygen through liquid DMDS on its route to the fermentation vessel.

Example 5

Construction of a ΔmetE ΔmetH Strain

Figure 10:
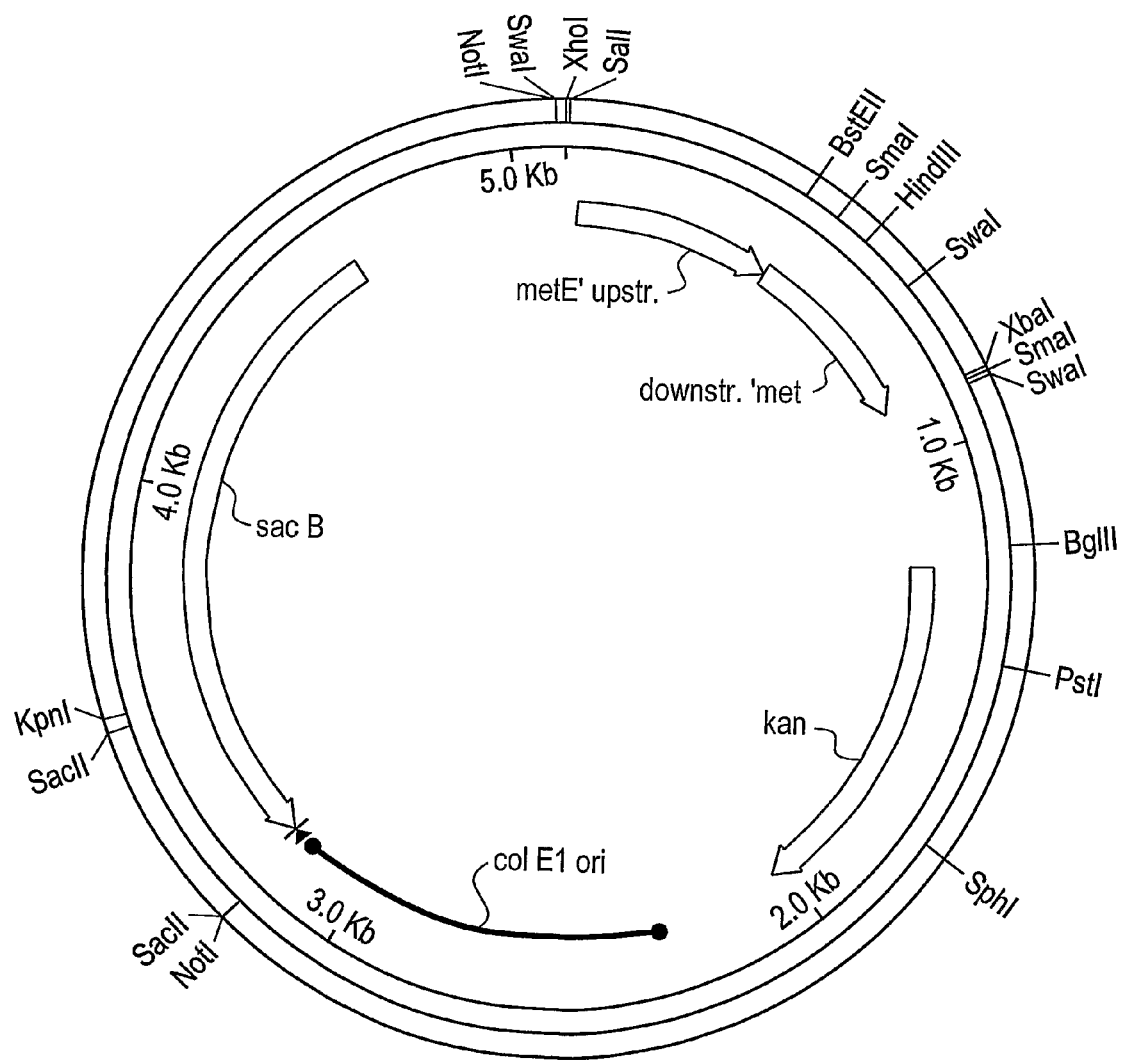
FIG. 10 is a schematic of the pH469 vector.
Figure 11:
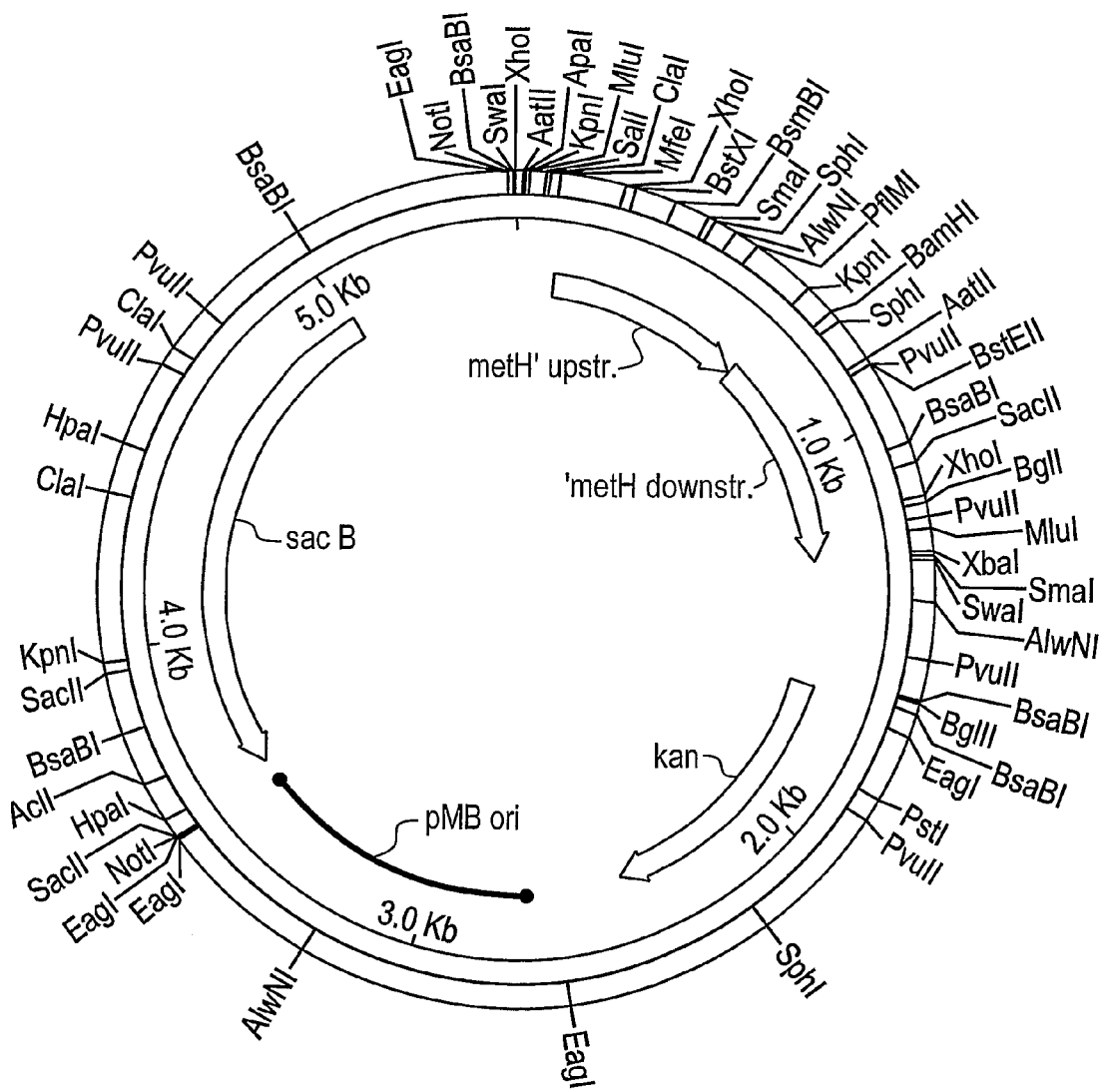
FIG. 11 is a schematic of the pH300 vector.

A C. glutamicum strain that is deleted for both metE and metH was constructed. M2014 was transformed with plasmid pH469 (FIG. 10) (SEQ ID NO:9) to yield a "Campbell in" strain. The "Campbell in" strain was then "Campbelled out" to yield a "Campbell out" strain, OM228C-2, which contains the mete deletion. Then OM228C-2 was transformed with plasmid pH300 (FIG. 11) (SEQ ID NO:10) to yield a "Campbell in" strain. The "Campbell in" strain was then "Campbelled out" to yield a "Campbell out" strain, OM246C, which contains both the ΔmetE and ΔmetH. As expected, two isolates of the double deletion strain, OM246C-1 and OM246C-2, are methionine auxotrophs and do not produce methionine in test tube cultures in molasses medium.

Example 6

MetY is Responsible for the Majority of the Enzymatic Activity Catalyzing the Reaction Between Methane Thiol with O-Acetyl-Homoserine for the Production of Methionine Since literature reports suggest that either MetB lavin, M. and S. Slaughter 1967. Biochim. Biophys. Acta, 132:400-405; Kanzaki, H. et al. 1987. Eur. J. Biochem. 163:105-112; Kiene, R. P. et al. 1999. Appl. Environ. Microbiol. 65:4549-4558) or MetZ (Yamagata, S. 1971. J. Biochem. (Tokyo) 70:1035) could be involved in methane thiol incorporation, an experiment was performed with an OM63 derivative containing a ΔMetB allele to identify the enzyme involved in methane thiol incorporation in C. glutamicum. As demonstrated above, C. glutamicum can incorporate dimethyl disulfide (DMDS), via methane thiol, directly into methionine. In Example 3, it was determined that DMDS is tolerated by the cells if added directly to liquid cultures at amounts less than about 0.06%, however if added in the presence of a delivery system, such as the adsorbent Amberlite™ XAD4, the amounts of DMDS added to liquid cultures can be increased 5-fold before toxicity is observed.

The methionine auxotroph OM63 (ΔmetF) was used for "proof of concept" experiments showing that C. glutamicum can utilize DMDS to support growth of a ΔmetF methionine auxotroph. In order to further define which enzyme(s) are involved in the incorporation of methane thiol into methionine in C. glutamicum, strains that contain a deletion in metB were tested for their ability to grow in the presence of DMDS.

OM101C (ΔmetF, ΔmetB), derived from OM63 transformed with H216, which contains the same metB deletion allele as pSH315 (Hwang B J, et al. J. Bacteriol. 2002 March; 184(5):1277-86) to delete metB, OM246c (ΔmetH, ΔmetE), described in Example 4, OM63 (ΔmetF), and M2014 were grown in test tubes containing 100 µl of a 50% suspension of Amberlite XAD4 and either methionine-free medium, or methionine-free medium supplemented with various amounts of DMDS. As shown in Table 10, the optical densities were similar for all strains in test tubes containing methionine-free medium supplemented with 0.1 or 0.2% DMDS. All strains were able to grow in methionine-free medium supplemented with 0.4% DMDS with the exception of OM101C, which showed an inhibition of growth at 0.3% DMDS. Only strain OM246C was able to grow in the presence of 0.5% DMDS. Taken together, these results show that MetB, MetH/MetE and MetF are not necessary for the incorporation of methane thiol into methionine. Therefore, MetY is sufficient for the enzymatic activity that allows incorporation of DMDS into methionine.

TABLE 10

Optical densities at 600 nm of OM63, OM101C, OM246C and M2014 grown in test tubes in methionine-free medium[1] for 24 hours at 30° C. with the indicated amounts of DMDS and in the presence of Amberlite XAD4[2].

| Strain | Parent | Genotype | DMDS 0% | DMDS 0.1% | DMDS 0.2% | DMDS 0.3% | DMDS 0.4% | DMDS 0.5% | met 100 mg/l |
|---|---|---|---|---|---|---|---|---|---|
| OM63 | M2014 | ΔmetF | 0.0 | 3.0 | 1.7 | 3.9 | 1.5 | 0.1 | 2.4 |
|  |  |  | 0.0 | 3.3 | 3.4 | 2.1 | 1.6 | 0.1 | 3.0 |

TABLE 10-continued

Optical densities at 600 nm of OM63, OM101C, OM246C and M2014 grown in test tubes in methionine-free medium[1] for 24 hours at 30° C. with the indicated amounts of DMDS and in the presence of Amberlite XAD4[2].

| Strain | Parent | Genotype | DMDS 0% | DMDS 0.1% | DMDS 0.2% | DMDS 0.3% | DMDS 0.4% | DMDS 0.5% | met 100 mg/l |
|---|---|---|---|---|---|---|---|---|---|
| OM101C | OM63 | ΔmetF | 0.0 | 2.5 | 3.1 | 1.6 | 0.05 | 0.02 | 1.9 |
| | | ΔmetB | 0.0 | 2.7 | 3.9 | 0.8 | 0.03 | 0.01 | 2.1 |
| OM246C | M2014 | ΔmetE | 0.0 | 4.3 | 4.2 | 3.3 | 3.6 | 3.1 | 3.9 |
| | | ΔmetH | 0.0 | 4.5 | 3.8 | 3.6 | 3.2 | 2.4 | 4.3 |
| M2014 | | parent | 4.3 | 4.4 | 4.0 | 3.8 | 1.3 | 0.07 | 4.4 |
| | | | 4.1 | 4.3 | 4.2 | 3.5 | 2.3 | 0.03 | 4.7 |

[1]Methionine-free medium.
[2]Each test tube contains 5 ml medium plus 100 μl of a 50% suspension of XAD4. Test tubes were inoculated after the XAD4 and DMDS were added.
Inoculum- Cells were grown overnight in test tubes containing BHI and then spun and rinsed 2x with Met free medium. Cells were resuspended in 50% of the starting volume. 5 μl of the cell suspension was used as the inoculum for each test tube.

Example 7

Identification of MetY as the Enzyme with O-acetylhomoserine Methane Thiol Sulfhydrylase Activity Here we show directly that MetY, but not MetB, is the enzyme necessary and sufficient for O-acetylhomoserine methane thiol sulfhydrylase activity. A test tube experiment was performed with M2014 derivatives that contain different combinations of deletions of metY, metB, and metF. The strains were grown in methionine free medium with Amberlite™ XAD4 beads and with or without DMDS at 200 mg/l or methionine at 100 mg/l. The inoculum was approximately $5 \times 10^3$ cells per tube. Cells were grown at 30° C. in a platform shaker for 60 hours, and cell densities were measured at $OD_{600}$.

As shown in Table 11, DMDS can support growth of the methionine auxotrophs OM63 (ΔmetF) and OM101 (ΔmetF, ΔmetB), however, DMDS does not support the growth of any methionine auxotroph containing a metY deletion, such as OM158 or OM174. OM158 was constructed by transforming OM63 with plasmid pH215 (SEQ ID NO:11) to yield a "Campbell in" strain. The nucleic acid sequence shown in SEQ ID NO: 11 is the region in pH215 of the deleted metY gene, extending from the start codon of metY, residues 1-3, to the stop codon of metA, residues 912-914. The two bases surrounding the deletion are at residues 609-610. The "Campbell in" strain was then "Campbelled out" to yield a "Campbell out" strain, OM158, which contains ΔmetF, ΔmetY. OM174 was constructed by transforming OM101 with plasmid pH215 to yield a "Campbell in" stain. The "Campbell in" strain was then "Campbelled out" to yield a "Campbell out" strain, OM174, which contains ΔmetF, ΔmetB, ΔmetY. FIG. 8 shows of the structure of the *C. glutamicum* chromosome in the region of metY before (8A) and after (8B) deletion of a portion of metY using plasmid pH215.

This data shows that MetY is the sole enzyme responsible for O-acetylhomoserine methane thiol sulfhydrylase activity, and neither MetB nor MetC contains a sufficient level of this enzymatic activity for growth under these conditions.

TABLE 11

$OD_{600}$ of strains grown in test tubes in methionine-free medium for 60 hours at 30° C. with or without 0.2% DMDS and Amberlite XAD4.

| Strain | Parent | Relevant Genotype | DMDS 0% | DMDS 0.2% | Met 100 mg/ml |
|---|---|---|---|---|---|
| M2014 | | | 2.3 | 3.6 | 2.3 |
| | | | 2.3 | 4.5 | 2.2 |
| OM63 | M2014 | ΔmetF | 0.0 | 1.2 | 1.6 |
| | | | 0.0 | 1.3 | 1.9 |
| OM158 | OM63 | ΔmetF., ΔmetY | 0.0 | 0.0 | 3.2 |
| | | | 0.0 | 0.0 | 2.7 |
| OM101 | OM63 | ΔmetF., ΔmetB | 0.0 | 2.4 | 1.8 |
| | | | 0.0 | 1.8 | 1.8 |
| OM174 | OM101 | ΔmetF., ΔmetB, ΔmetY | 0.0 | 0.0 | 1.5 |
| | | | 0.0 | 0.0 | 1.2 |

Example 8

Efficiency of Methionine Production in Auxotrophic Strains of *C. glutamicum*

Once it was established that a ΔmetF or ΔmetE ΔmetH *C. glutamicum* auxotroph could utilize DMDS for the synthesis of methionine, it was of interest to determine the efficiency of methionine production. A shake flask experiment was performed where OM246C was compared to M2014. Each shake flask contained 20 ml molasses medium and 800 μl of a 50% suspension of Amberlite™ XAD4 with or with out 0.4% DMDS. As shown in Table 12, OM246C without DMDS accumulated little methionine. In contrast, 0M246C supplemented with DMDS accumulated about 0.3 g/l methionine. Thus, the production of methionine occurs from the conversion of O-acetyl-homoserine directly to methionine, bypassing homocysteine. Most importantly, the net increase in methionine titer in OM246C, grown in the presence of DMDS, firmly establishes that methionine can be produced by *C. glutamicum* mutants defective in the last step in methionine synthesis when DMDS is present. The control strain M2014 accumulated similar profiles of amino acids, whether grown in the presence of DMDS or not. Interestingly, DMDS slightly stimulated methionine production in M2014 from about 0.5 g/l to about 0.7 g/l. This is explained by an additive effect of the incorporation of DMDS in combination with the production of methionine from the conventional methionine biosynthetic pathways.

TABLE 12

Shake flask study of M2014 and OM246C grown in molasses medium[1] at 30° C. with or without 0.4% DMDS[2].

| Strain | DMDS | Glu[3] | Gly + Hse | O—Ac-hse | Met | Ile | Lys | OD$_{600}$ |
|---|---|---|---|---|---|---|---|---|
| 2014 | 0 μl | 0.0 | 1.2 | 5.4 | 0.5 | 0.0 | 2.6 | 33 |
|  |  | 0.0 | 1.6 | 4.4 | 0.4 | 0.0 | 2.9 | 34 |
|  | 80 μl | 0.1 | 1.4 | 3.6 | 0.7 | 0.0 | 2.5 | 30 |
|  |  | 0.0 | 1.0 | 4.3 | 0.6 | 0.0 | 2.5 | 38 |
| OM246C | 0 μl | 5.3 | 0.7 | 0.3 | 0.0 | 0.1 | 1.8 | 32 |
|  |  | 3.0 | 0.7 | 1.1 | 0.0 | 0.2 | 1.7 | 30 |
|  | 80 μl | 0.0 | 1.7 | 4.6 | 0.4 | 0.0 | 3.2 | 32 |
|  |  | 0.2 | 1.3 | 4.3 | 0.2 | 0.0 | 3.4 | 35 |

[1]Molasses medium was supplemented with 1% yeast extract, biotin, B$_1$, B$_{12}$, B$_6$, and 100 mg/l threonine.
[2]Each shake flask contains 20 ml medium plus 800 μl of a 50% suspension of XAD4. Shake flasks were inoculated after the XAD4 and 80 μl of DMDS (with or without) were added. The final concentration of DMDS added is 0.4% v/v.
Inoculum- Cells were grown overnight in test tubes containing BHI and then spun and rinsed 2× with Met free medium. Cells were resuspended in 50% of the starting volume. 100 μl of the cell suspension was used as inoculum for each shake flask.
[3]Amino acids are reported in g/l.

Example 9

Further Development of a Delivery System of DMDS to *C. glutamicum* for Incorporation into Methionine In order to further explore potential delivery systems of DMDS (in addition to Amberlite™ XAD4) both heavy white mineral oil (Sigma cat. no. 400-5) and a vegetable oil, canola oil, were investigated. Since oils are hydrophobic, they should be able to dissolve DMDS and potentially allow the slow release of DMDS into the aqueous medium. Oil (0.5 ml) containing various amounts of dissolved DMDS was added to test tubes containing 5 ml of methionine-free medium with or without 100 mg/l methionine. Optical densities of cell cultures containing 0, 0.2, 0.4, 0.8 and 1.2% final concentrations of DMDS were measured after incubation at 30° C. for 24 hours in a platform shaker. As shown in Table 13, growth of OM246C occurred in test tubes containing up to 0.4% DMDS, while growth of AU014 occurred in test tubes containing up to 0.8% DMDS dissolved in mineral oil. However, the optical densities were less than half compared to those of test tube cultures containing methionine-free medium without mineral oil. The maximum amount of DMDS in mineral oil compared to Amberlite™ XAD4 that allowed cell growth was slightly higher for M2014 (0.8% vs. 0.4%) but similar for OM63 (0.4% vs. 0.4%). Similar results were observed when canola oil was tested as a delivery system; however, canola oil alone does not have as great a negative affect on cell growth as mineral oil (Table 14). The reduced growth in the presence of these oils may be due, in part, to the lack of sufficient aeration in the test tube cultures, disruption of the cell membrane, or a combination of the two. Nonetheless, it is clear that oils can be used as a delivery system for DMDS in fermentations. Oils derived from animal, mineral, chemical or vegetable sources, or a combination thereof could be used for delivery of DMDS to cells. Other possible delivery systems include synthetic oils, organic solvents, chloro-carbons, fluoro-carbons, or chloro-fluoro-carbons. An additional approach would be a slow controlled DMDS feed that provides a steady state level to the cells that is below the toxic level. Selecting DMDS resistant *C. glutamicum* strains would also alleviate the DMDS toxicity issues. Finally, utilizing a host species that is inherently more resistant to DMDS toxicity would also alleviate this problem.

TABLE 13

Optical densities at 600 nm of *C. glutamicum* test tube cultures grown in methionine free medium with or without methionine or dimethyl disulfide (DMDS) and mineral oil for 24 hours at 30° C.

| Strain | Genotype | MF[1] | MF + Met[2] | MF + Mineral Oil[3] | MF + Met + Mineral Oil | MF + Mineral Oil + 0.2% DMDS | MF + Mineral Oil + 0.4% DMDS | MF + Mineral Oil + 0.8% DMDS | MF + Mineral Oil + 1.2% DMDS |
|---|---|---|---|---|---|---|---|---|---|
| M2014 | Parent | 4.7 | 4.6 | 1.2 | 2.4 | 1.4 | 1.5 | 1.4 | 0.0 |
|  |  | 4.8 | 4.8 | 1.9 | 1.1 | 1.2 | 1.3 | 1.7 | 0.0 |
| OM246C | ΔmetH, | 0.0 | 4.9 | 0.0 | 1.5 | 1.1 | 1.2 | 0.0 | 0.0 |
|  | ΔmetE | 0.0 | 4.7 | 0.0 | 1.8 | 1.6 | 1.5 | 0.0 | 0.0 |

[1]Methionine-free medium
[2]100 mg/l methionine.
[3]0.5 ml of mineral oil added to each 5 ml of medium.

TABLE 14

Optical densities at 600 nm of *C. glutamicum* test tube cultures grown in methionine free medium with or without methionine or dimethyl disulfide (DMDS) and canola oil for 24 hours at 30° C.

| Strain | Genotype | MF[1] | MF + Met[2] | MF + Canola Oil[3] | MF + Met + Canola Oil | MF + Canola Oil + 0.2% DMDS | MF + Canola Oil + 0.4% DMDS | MF + Canola Oil + 0.8% DMDS |
|---|---|---|---|---|---|---|---|---|
| M2014 | Parent | 4.7 | 4.6 | 3.2 | 3.8 | 1.5 | 0.3 | 0.0 |
|  |  | 4.8 | 4.8 | 3.6 | 3.5 | 1.4 | 1.3 | 0.1 |
| OM246C | ΔmetH, | 0.0 | 4.9 | 0.0 | 3.7 | 1.9 | 1.1 | 0.0 |
|  | ΔmetE | 0.0 | 4.7 | 0.0 | 3.0 | 1.7 | 1.3 | 0.0 |

[1]Methionine-free medium
[2]100 mg/l methionine.
[3]0.5 ml of canola oil added to each 5 ml of medium.

Example 10

Strain Improvement

The *E. coli* metB gene has been mutated or evolved to utilize methane thiol (WO 2004/076659 A2). Similar selection procedures can be applied using methionine auxotrophs, for example lacking MetF, and MetH or MetF, but using DMDS rather than methane thiol in the selective medium. Thus, microorganisms can be selected for that have a greater capacity for incorporating DMDS into methionine, by starting with a methionine auxotroph that, for example, can produce O-acetyl homoserine or O-succinyl homoserine, but can not use homocysteine, and selecting for growth, or more rapid growth, on a minimal medium lacking methionine but containing DMDS, and with or without mutagenesis by chemicals, radiation, or mutator alleles. This type of selection can be focused on a particular gene, for example, a metB gene, a metY gene, a metC gene, or a metI gene (Auger et al., 2002 *Microbiology* 148: 507-518), by installing the gene on a plasmid and introducing the plasmid into a strain that lacks (by deletion or mutation) endogenous ability to incorporate DMDS, and performing the selection as describe above. Descendants of such selected microorganisms, or genes isolated from such selected microorganisms, are also useful for constructing or deriving methionine production strains.

Example 11

*E. coli* can Metabolize DMDS into Methionine if Supplied with O-Acetyl Homoserine Sulfhydrylase or O-Succinyl Homoserine Sulfhydrylase

*E. coli* methionine auxotrophs CGSC 3592 (metF64) and RY714B, a metE::Tn10, ΔmetH derivative of MM294, also known as ATCC 33625 and CGSC 6315 (endA1, thi-1, supE44, hsdR17), were transformed with pH357 (SEQ ID NO:13; a plasmid that expresses *C. glutamicum* metY and metX), pH309 (SEQ ID NO:14; a plasmid that expresses *C. glutamicum* metY), or pCLIK, which is an empty vector related to pH357 and pH309 that replicates in *E. coli* and *C. glutamicum* (SEQ ID NO:15). The selection was for resistance to kanamycin sulfate at 25 mg/L on rich medium Curia Broth agar). The six transformants were plated on methionine free agar medium, a well was cut in the center of the agar, 50 microliters of DMDS was added to the well, and the plates were incubated as described in Example 4 at 30° C. Both strains transformed with either pH309 or pH357 grew on the plates, but neither strain transformed with empty vector pCLIK grew, demonstrating that metY was necessary and sufficient for *E. coli* to utilize DMDS to synthesize methionine. These results also support the contention that MetY has both O-acetyl homoserine sulfhydrylase and O-succinyl homoserine sulfhydrylase activity, since RY714B/pH309, for example, relies on the *E. coli* MetA enzyme, which is known to produce primarily O-succinyl homoserine.

Thus, *E. coli* if engineered as described herein, has the ability to import DMDS, reduce it, and incorporate it into methionine. Since *E. coli* and *C. glutamicum*, which are not closely related organisms, both have this ability, we anticipate that a wide variety of organisms have this ability, and that a wide variety of organisms can be engineered to produce methionine using DMDS as one of the fed compounds.

Example 12

Selection for Feedback Resistant O-Acetylhomoserine Sulfhydrylase or O-Succinylhomoserine Sulfhydrylase Enzyme To make methionine biosynthetically, it is desirable to use feedback resistant O-acetylhomoserine sulfhydrylase and/or O-succinylhomoserine sulfhydrylase enzymes. In many organisms, these enzymes are feedback inhibited by methionine. For example, MetY (O-acetylhomoserine sulfhydrylase) in *Corynebacterium glutamicum* is feedback inhibited by methionine, which is counterproductive for methionine synthesis. Mutated versions of MetY that are supposedly resistant to inhibition by methionine have been described (WO 2004/108894 A2), but these versions might not be the best versions for improving methionine biosynthesis. Thus, there is still a need for suitable feedback resistant versions of MetY. Since MetY has been shown herein to be an enzyme that can confer growth on DMDS, a novel scheme for selecting useful metY alleles were developed as follows. A C glutamicum strain that lacks MetF or MetE and MetH, and optionally also lacks MetY, Met and/or MetC, but which is engineered for relatively high O-acetyl homoserine synthesis (for example, OM174 (ΔmetF, ΔmetB, ΔmetY) or OM246C (ΔmetE, ΔmetH)) (U.S. Provisional Patent Application No. 60/700,699, filed on Jul. 18, 2005, entitled "Methionine Producing Recombinant Microorganism"), is transformed with a plasmid that expresses MetY such as pH357 or pH309. The resulting strain can grow on methionine free medium that contains DMDS by virtue of the MetY produced by the plasmid pH357 or pH309. Methionine analogs, such as α-methyl methionine, selenomethionine, norleucine, trifluoromethionine, methionine hydroxamate, ethionine, S-methyl cysteine, and the like, are screened for those that inhibit growth of the strain. An analog that inhibits growth of the strain will in some cases do so by false feedback inhibition of MetY. In other words, the analog will bind to the methionine binding site on MetY, and inhibit the enzyme's activity. Selection (with or without mutagenesis) for mutants resistant to said analog will result in variants of MetY that are resistant to binding of the analog and to methionine. Plasmid DNA is isolated from such mutant candidates and retransformed into the naïve, unmutated host strain, and it is determined whether the analog resistant phenotype is encoded by the introduced plasmid. Plasmids that pass this screen will contain one or more mutations, some of which will confer the desired feedback resistance to methionine.

The scheme described above for creating and identifying feedback resistant O-acetylhomoserine sulfhydrylase variants is also appropriate for isolating feedback resistant O-succinylhomoserine sulfhydrylase enzyme variants. The method is similar, but the starting organism produces O-succinylhomoserine as an intermediate instead of O-acetylhomoserine, and the plasmid encodes an O-succinylhomoserine sulfhydrylase enzyme instead of O-acetylhomoserine sulfhydrylase. In other words, the plasmid contains a metZ gene instead of a metY gene.

The above described selection for feedback resistant MetY or MetZ can also be carried out in organisms other than *C. glutamicum*. For example, as shown in Example 11 above, *E. coli* RY 714B/pH309 or *E. coli* CGSC 3592/pH357, etc., can also grow on methionine free medium with DMDS, so such strains can also be used to select for desirable variants of MetY by growing on methionine free medium containing DMDS, and selecting for resistance to methionine analogs.

Since *E. coli* MetA is also sensitive to inhibition by methionine and to some analogs, such as β-methyl methionine (Usuda Y, Kurahashi O., *Appl. Environ. Microbiol.*, 2005 June; 71 (6):3228-34), the selection for desirable metY alleles can be enhanced by using an *E. coli* metA⁻ mutant and supplying a feedback resistant MetA or MetX, for example with pH357, or using a metA allele that has already been selected for resistance to the analog. In general, this method should work in a wide variety of bacteria, yeasts, fungi, Archaea, and plants.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method of producing methionine, comprising culturing a methionine producing microorganism in the presence of a methyl capped sulfide compound, such that methionine is produced, wherein the methyl capped sulfide compound is $H_3C$—$(S)n$—$CH_3$, and n is 2-50.

2. A method of producing methionine, comprising culturing a methionine producing microorganism in the presence of dimethyl disulfide (DMDS), such that methionine is produced.

3. The method of claim 1 or 2, wherein the DMDS is present at 0.02% or higher in the culture.

4. The method of claim 1 or 2, wherein the DMDS is present at 0.06% or higher in the culture.

5. A method of producing methionine, comprising culturing a methionine producing microorganism in the presence of a slow release dimethyl disulfide (DMDS) delivery system, such that methionine is produced.

6. The method of claim 5, wherein the slow release DMDS delivery system comprises a liquid that is immiscible with water, but which dissolves DMDS.

7. The method of claim 6, wherein the slow release DMDS delivery system comprises a liquid selected from the group consisting of: animal oils, mineral oils, chemical oils, vegetable oils, synthetic oils, organic solvent, chloro-carbons, fluoro-carbons, chloro-fluoro-carbons, or a combination thereof.

8. The method of claim 5, wherein the slow release DMDS delivery system is a slow controlled DMDS feed.

9. The method of claim 5, wherein the slow release DMDS delivery system is flow or diffusion of DMDS through a membrane that is permeable to DMDS.

10. The method of claim 5, wherein the slow release DMDS delivery system comprises feeding DMDS in a gaseous state.

11. The method of claim 10, wherein the DMDS in a gaseous state is generated by evaporating or boiling liquid DMDS.

12. The method of claim 10, wherein the DMDS in a gaseous state is generated by bubbling air or oxygen through liquid DMDS.

13. The method of any one of claims 2, and 5, wherein the methionine producing microorganism belongs to the genus *Corynebacterium*.

14. The method of any one of claims 2, and 5, wherein the methionine producing microorganism is *Corynebacterium glutamicum*.

15. The method of any one of claims 2, and 5, wherein the methionine producing microorganism is selected from the group consisting of Gram-negative bacteria, Gram-positive bacteria, yeast, and Archaea.

16. The method of any one of claims 2, and 5, wherein the methionine producing microorganism has at least one methionine biosynthetic enzyme deregulated.

17. The method of claim 16, wherein said microorganism has a deregulated O-acetyl-homoserine sulfhydrylase or O-succinyl-homoserine sulfhydrylase.

18. The method of any one of claims 2, and 5, wherein the methionine producing microorganism has at least two methionine biosynthetic enzymes deregulated.

19. The method of claim 18, wherein said microorganism has a deregulated homoserine acetyltransferase or homoserine succinyltransferase and a deregulated homoserine dehydrogenase.

20. The method of claim 18, wherein said microorganism has a deregulated O-acetyl-homoserine sulfhydrylase and a deregulated homoserine acetyltransferase or a deregulated O-succinyl-homoserine sulfhydrylase and a deregulated homoserine succinyltransferase.

21. A method of producing methionine, comprising culturing a microorganism having a deregulated methionine biosynthetic pathway in the presence of dimethyl disulfide (DMDS), such that methionine is produced.

22. The method of claim 21 wherein the microorganism belongs to the genus *Corynebacterium*.

23. The method of claim 21, wherein the microorganism is *Corynebacterium* glutamicum.

24. The method of claim 21, wherein the microorganism belongs to the genus *Escherichia*.

25. The method of claim 21, wherein the microorganism is selected from the group consisting of: Gram-negative bacteria, Gram-positive bacteria, yeast, and Archaea.

26. The method of claim 21, wherein said microorganism has a deregulated O-acetyl-homoserine sulfhydrylase or O-succinyl-homoserine sulfhydrylase.

27. The method of claim 21, wherein said microorganism has a deregulated homoserine acetyltransferase or homoserine succinyltransferase and a deregulated homoserine dehydrogenase.

28. The method of claim 21, wherein said microorganism has a deregulated O-acetyl-homoserine sulfhydrylase and a deregulated homoserine acetyltransferase or a deregulated O-succinyl-homoserine sulfhydrylase and a deregulated homoserine succinyltransferase.

29. The method of claim 21, further comprising the step of isolating the methionine.

30. A recombinant microorganism that produces methionine in the presence of dimethyl disulfide (DMDS), said microorganism having a deregulated methionine biosynthetic pathway.

31. The microorganism of claim 30 belonging to the genus *Corynebacterium*.

32. The microorganism of claim 31 which is *Corynebacterium* glutamicum.

33. The microorganism of claim 30 belonging to the genus *Escherichia*.

* * * * *

```
                       SEQUENCE LISTING

<160> NUMBER OF SEQ ID NOS: 15

<210> SEQ ID NO 1
<211> LENGTH: 7070
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 1
tcgagaggcc tgacgtcggg cccggtacca cgcgtcatat gactagttgg agaatcatga      60
cctcagcatc tgccccaagc tttaaccccg gcaagggtcc cggctcagca gtcggaattg     120
cccttttagg attcggaaca gtcggcactg aggtgatgcg tctgatgacc gagtacggtg     180
atgaacttgc gcaccgcatt ggtggcccac tggaggttcg tggcattgct gtttctgata     240
tctcaaagcc acgtgaaggc gttgcacctg agctgctcac tgaggacgct tttgcactca     300
tcgagcgcga ggatgttgac atcgtcgttg aggttatcgg cggcattgag tacccacgtg     360
aggtagttct cgcagctctg aaggccggca agtctgttgt taccgccaat aaggctcttg     420
ttgcagctca ctctgctgag cttgctgatg cagcggaagc cgcaaacgtt gacctgtact     480
tcgaggctgc tgttgcaggc gcaattccag tggttggccc actgcgtcgc tccctggctg     540
gcgatcagat ccagtctgtg atgggcatcg ttaacgcgca caccaacttc atcttggacg     600
ccatggattc caccggcgct gactatgcag attctttggc tgaggcaact cgtttgggtt     660
acgccgaagc tgatccaact gcagacgtcg aaggccatga cgccgcatcc aaggctgcaa     720
ttttggcatc catcgctttc cacacccgtg ttaccgcgga tgatgtgtac tgcgaaggta     780
tcagcaacat cagcgctgcc gacattgagg cagcacagca ggcaggccac accatcaagt     840
tgttggccat ctgtgagaag ttcaccaaca aggaaggaaa gtcggctatt tctgctcgcg     900
tgcacccgac tctattacct gtgtcccacc cactggcgtc ggtaaacaag tcctttaatg     960
caatctttgt tgaagcagaa gcagctggtc gcctgatgtt ctacggaaac ggtgcaggtg    1020
gcgcgccaac cgcgtctgct gtgcttggcg acgtcgttgg tgccgcacga aacaaggtgc    1080
acggtggccg tgctccaggt gagtccacct acgctaacct gccgatcgct gatttcggtg    1140
agaccaccac tcgttaccac ctcgacatgg atgtggaaga tcgcgtgggg gttttggctg    1200
aattggctag cctgttctct gagcaaggaa tcttcctgcg tacaatccga caggaagagc    1260
gcgatgatga tgcacgtctg atcgtggtca cccactctgc gctggaatct gatctttccc    1320
gcaccgttga actgctgaag gctaagcctg ttgttaaggc aatcaacagt gtgatccgcc    1380
tcgaaaggga ctaattttac tgacatggca attgaactga acgtcggtcg taaggttacc    1440
gtcacggtac ctggatcttc tgcaaaccct ggacctggct ttgacacttt aggtttggca    1500
ctgtcggtat acgacactgt cgaagtggaa attattccat ctggcttgga agtggaagtt    1560
```

```
tttggcgaag gccaaggcga agtccctctt gatggctccc acctggtggt taaagctatt    1620
cgtgctggcc tgaaggcagc tgacgctgaa gttcctggat tgcgagtggt gtgccacaac    1680
aacattccgc agtctcgtgg tcttggctcc tctgctgcag cggcggttgc tggtgttgct    1740
gcagctaatg gtttggcgga tttcccgctg actcaagagc agattgttca gttgtcctct    1800
gcctttgaag gccacccaga taatgctgcg gcttctgtgc tgggtggagc agtggtgtcg    1860
tggacaaatc tgtctatcga cggcaagagc cagccacagt atgctgctgt accacttgag    1920
gtgcaggaca atattcgtgc gactgcgctg gttcctaatt tccacgcatc caccgaagct    1980
gtgcgccgag tccttcccac tgaagtcact cacatcgatg cgcgatttaa cgtgtcccgc    2040
gttgcagtga tgatcgttgc gttgcagcag cgtcctgatt tgctgtggga gggtactcgt    2100
gaccgtctgc accagcctta tcgtgcagaa gtgttgccta ttacctctga gtgggtaaac    2160
cgcctgcgca accgtggcta cgcggcatac cttttcggtg ccggcccaac cgccatggtg    2220
ctgtccactg agccaattcc agacaaggtt ttggaagatg ctcgtgagtc tggcattaag    2280
gtgcttgagc ttgaggttgc gggaccagtc aaggttgaag ttaaccaacc ttaggcccaa    2340
caaggaaggc cccctccgaa tcaagaaggg ggccttatta gtgcagcaat tattcgctga    2400
acacgtgaac cttacaggtg cccggcgcgt tgagtggttt gagttccagc tggatgcggt    2460
tgttttcacc gaggctttct tggatgaatc cggcgtggat ggcgcagacg aaggctgatg    2520
ggcgtttgtc gttgaccaca aatgggcagc tgtgtagagc gagggagttt gcttcttcgg    2580
tttcggtggg gtcaaagccc atttcgcgga ggcggttaat gagcggggag agggcttcgt    2640
cgagttcttc ggcttcggcg tggttaatgc ccatgacgtg tgcccactgg gttccgatgg    2700
aaagtgcttt ggcgcggagg tcggggttgt gcattgcgtc atcgtcgaca tcgccgagca    2760
tgttggccat gagttcgatc agggtgatgt attctttggc gacagcgcgg ttgtcgggga    2820
cgcgtgtttg gaagatgagg gaggggcggg atcctctaga cccgggattt aaatcgctag    2880
cgggctgcta aaggaagcgg aacacgtaga aagccagtcc gcagaaacgg tgctgacccc    2940
ggatgaatgt cagctactgg gctatctgga caagggaaaa cgcaagcgca aagagaaagc    3000
aggtagcttg cagtgggctt acatggcgat agctagactg gcggttttta tggacagcaa    3060
gcgaaccgga attgccagct ggggcgccct ctggtaaggt tgggaagccc tgcaaagtaa    3120
actggatggc tttcttgccg ccaaggatct gatggcgcag gggatcaaga tctgatcaag    3180
agacaggatg aggatcgttt cgcatgattg aacaagatgg attgcacgca ggttctccgg    3240
ccgcttgggt ggagaggcta ttcggctatg actgggcaca acagacaatc ggctgctctg    3300
atgccgccgt gttccggctg tcagcgcagg ggcgcccggt tctttttgtc aagaccgacc    3360
tgtccggtgc cctgaatgaa ctgcaggacg aggcagcgcg gctatcgtgg ctggccacga    3420
cgggcgttcc ttgcgcagct gtgctcgacg ttgtcactga agcgggaagg gactggctgc    3480
tattgggcga agtgccgggg caggatctcc tgtcatctca ccttgctcct gccgagaaag    3540
tatccatcat ggctgatgca atgcggcggc tgcatacgct tgatccggct acctgcccat    3600
tcgaccacca agcgaaacat cgcatcgagc gagcacgtac tcggatggaa gccggtcttg    3660
tcgatcagga tgatctggac gaagagcatc aggggctcgc gccagccgaa ctgttcgcca    3720
ggctcaaggc gcgcatgccc gacggcgagg atctcgtcgt gacccatggc gatgcctgct    3780
tgccgaatat catggtggaa aatggccgct tttctggatt catcgactgt ggccggctgg    3840
gtgtggcgga ccgctatcag gacatagcgt tggctacccg tgatattgct gaagagcttg    3900
gcggcgaatg ggctgaccgc ttcctcgtgc tttacggtat cgccgctccc gattcgcagc    3960
```

```
gcatcgcctt ctatcgcctt cttgacgagt tcttctgagc gggactctgg ggttcgaaat   4020
gaccgaccaa gcgacgccca acctgccatc acgagatttc gattccaccg ccgccttcta   4080
tgaaaggttg ggcttcggaa tcgttttccg ggacgccggc tggatgatcc tccagcgcgg   4140
ggatctcatg ctggagttct tcgcccacgc tagcggcgcg ccggccggcc cggtgtgaaa   4200
taccgcacag atgcgtaagg agaaaatacc gcatcaggcg ctcttccgct tcctcgctca   4260
ctgactcgct gcgctcggtc gttcggctgc ggcgagcggt atcagctcac tcaaaggcgg   4320
taatacggtt atccacagaa tcaggggata acgcaggaaa gaacatgtga gcaaaaggcc   4380
agcaaaaggc caggaaccgt aaaaaggccg cgttgctggc gtttttccat aggctccgcc   4440
cccctgacga gcatcacaaa aatcgacgct caagtcagag gtggcgaaac ccgacaggac   4500
tataaagata ccaggcgttt ccccctggaa gctccctcgt gcgctctcct gttccgaccc   4560
tgccgcttac cggatacctg tccgcctttc tcccttcggg aagcgtggcg ctttctcata   4620
gctcacgctg taggtatctc agttcggtgt aggtcgttcg ctccaagctg gctgtgtgc   4680 acgaaccccc cgttcagccc gaccgctgcg ccttatccgg taactatcgt cttgagtcca   4740
acccggtaag acacgactta tcgccactgg cagcagccac tggtaacagg attagcagag   4800
cgaggtatgt aggcggtgct acagagttct tgaagtggtg gcctaactac ggctacacta   4860
gaaggacagt atttggtatc tgcgctctgc tgaagccagt taccttcgga aaaagagttg   4920
gtagctcttg atccggcaaa caaaccaccg ctggtagcgg tggttttttt gtttgcaagc   4980
agcagattac gcgcagaaaa aaaggatctc aagaagatcc tttgatcttt tctacggggt   5040
ctgacgctca gtggaacgaa aactcacgtt aagggatttt ggtcatgaga ttatcaaaaa   5100
ggatcttcac ctagatcctt ttaaaggccg ccgcggccg ccatcggcat tttcttttgc   5160 gttttttattt gttaactgtt aattgtcctt gttcaaggat gctgtctttg acaacagatg   5220
ttttcttgcc tttgatgttc agcaggaagc tcggcgcaaa cgttgattgt ttgtctgcgt   5280
agaatcctct gtttgtcata tagcttgtaa tcacgacatt gtttccttc gcttgaggta   5340 cagcgaagtg tgagtaagta aaggttacat cgttaggatc aagatccatt tttaacacaa   5400
ggccagtttt gttcagcggc ttgtatgggc cagttaaaga attagaaaca taaccaagca   5460
tgtaaatatc gttagacgta atgccgtcaa tcgtcatttt tgatccgcgg gagtcagtga   5520
acaggtacca tttgccgttc atttttaaga cgttcgcgcg ttcaatttca tctgttactg   5580
tgttagatgc aatcagcggt ttcatcactt ttttcagtgt gtaatcatcg tttagctcaa   5640
tcataccgag agcgccgttt gctaactcag ccgtgcgttt tttatcgctt tgcagaagtt   5700
tttgactttc ttgacggaag aatgatgtgc ttttgccata gtatgctttg ttaaataaag   5760
attcttcgcc ttggtagcca tcttcagttc cagtgtttgc ttcaaatact aagtatttgt   5820
ggcctttatc ttctacgtag tgaggatctc tcagcgtatg gttgtcgcct gagctgtagt   5880
tgccttcatc gatgaactgc tgtacatttt gatacgtttt tccgtcaccg tcaaagattg   5940
atttataatc ctctacaccg ttgatgttca aagagctgtc tgatgctgat acgttaactt   6000
gtgcagttgt cagtgtttgt ttgccgtaat gtttaccgga gaaatcagtg tagaataaac   6060 ggattttttcc gtcagatgta aatgtggctg aacctgacca ttcttgtgtt tggtctttta   6120
ggatagaatc atttgcatcg aatttgtcgc tgtctttaaa gacgcggcca gcgttttcc   6180 agctgtcaat agaagtttcg ccgactttt gatagaacat gtaaatcgat gtgtcatccg   6240 cattttagg atctccggct aatgcaaaga cgatgtggta gccgtgatag tttgcgacag   6300
tgccgtcagc gttttgtaat ggccagctgt cccaaacgtc caggcctttt gcagaagaga   6360
```

-continued

```
tattttttaat tgtggacgaa tcaaattcag aaacttgata ttttttcattt ttttgctgtt    6420 cagggatttg cagcatatca tggcgtgtaa tatgggaaat gccgtatgtt tccttatatg    6480
gcttttggtt cgtttctttc gcaaacgctt gagttgcgcc tcctgccagc agtgcggtag    6540
taaaggttaa tactgttgct tgttttgcaa acttttgat gttcatcgtt catgtctcct    6600
tttttatgta ctgtgttagc ggtctgcttc ttccagccct cctgtttgaa gatggcaagt    6660
tagttacgca aataaaaaa agacctaaaa tatgtaaggg gtgacgccaa agtatacact    6720 ttgccctta cacattttag gtcttgcctg ctttatcagt aacaaacccg cgcgatttac    6780
ttttcgacct cattctatta gactctcgtt tggattgcaa ctggtctatt ttcctctttt    6840
gtttgataga aaatcataaa aggatttgca gactacgggc taaagaact aaaaaatcta    6900 tctgtttctt ttcattctct gtattttta tagtttctgt tgcatgggca taagttgcc    6960 tttttaatca caattcagaa aatatcataa tatctcattt cactaaataa tagtgaacgg    7020
caggtatatg tgatgggtta aaaggatcg gcggccgctc gatttaaatc    7070
```

<210> SEQ ID NO 2
<211> LENGTH: 7070
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 2

```
tcgagaggcc tgacgtcggg cccggtacca cgcgtcatat gactagttgg agaatcatga      60
cctcagcatc tgccccaagc tttaaccccg gcaagggtcc cggctcagca gtcggaattg     120
cccttttagg attcggaaca gtcggcactg aggtgatgcg tctgatgacc gagtacggtg     180
atgaacttgc gcaccgcatt ggtggcccac tggaggttcg tggcattgct gtttctgata     240
tctcaaagcc acgtgaaggc gttgcacctg agctgctcac tgaggacgct tttgcactca     300
tcgagcgcga ggatgttgac atcgtcgttg aggttatcgg cggcattgag tacccacgtg     360
aggtagttct cgcagctctg aaggccggca agtctgttgt taccgccaat aaggctcttg     420
ttgcagctca ctctgctgag cttgctgatg cagcggaagc cgcaaacgtt gacctgtact     480
tcgaggctgc tgttgcaggc gcaattccag tggttggccc actgcgtcgc tccctggctg     540
gcgatcagat ccagtctgtg atgggcatcg ttaacggcac caccaacttc atcttggacg     600
ccatggattc caccggcgct gactatgcag attctttggc tgaggcaact cgtttgggtt     660
acgccgaagc tgatccaact gcagacgtcg aaggccatga cgccgcatcc aaggctgcaa     720
ttttggcatc catcgctttc cacacccgtt taccgcgga tgatgtgtac tgcgaaggta     780
tcagcaacat cagcgctgcc gacattgagg cagcacagca ggcaggccac accatcaagt     840
tgttggccat ctgtgagaag ttcaccaaca aggaaggaaa gtcggctatt tctgctcgcg     900
tgcacccgac tctattacct gtgtcccacc cactggcgtc ggtaaacaag tcctttaatg     960
caatctttgt tgaagcagaa gcagctggtc gcctgatgtt ctacgaaac ggtgcaggtg    1020 gcgcgccaac cgcgtctgct gtgcttggcg acgtcgttgg tgccgcacga aacaaggtgc    1080
acggtggccg tgctccaggt gagtccacct cgctaacct gccgatcgct gatttcggtg    1140
agaccaccac tcgttaccac ctcgacatgg atgtggaaga tcgcgtgggg gttttggctg    1200
aattggctag cctgttctct gagcaaggaa tcttcctgcg tacaatccga caggaagagc    1260
gcgatgatga tgcacgtctg atcgtggtca cccactctgc gctggaatct gatctttccc    1320
gcaccgttga actgctgaag gctaagcctg ttgttaaggc aatcaacagt gtgatccgcc    1380
```

```
tcgaaaggga ctaattttac tgacatggca attgaactga acgtcggtcg taaggttacc    1440
gtcacggtac ctggatcttc tgcaaacctc ggacctggct ttgacacttt aggtttggca    1500
ctgtcggtat acgacactgt cgaagtggaa attattccat ctggcttgga agtggaagtt    1560
tttggcgaag gccaaggcga agtccctctt gatggctccc acctggtggt taaagctatt    1620
cgtgctggcc tgaaggcagc tgacgctgaa gttcctggat tgcgagtggt gtgccacaac    1680
aacattccgc agtctcgtgg tcttggctcc tctgctgcag cggcggttgc tggtgttgct    1740
gcagctaatg gtttggcgga tttcccgctg actcaagagc agattgttca gttgtcctct    1800
gcctttgaag gccacccaga taatgctgcg gcttctgtgc tgggtggagc agtggtgtcg    1860
tggacaaatc tgtctatcga cggcaagagc cagccacagt atgctgctgt accacttgag    1920
gtgcaggaca atattcgtgc gactgcgctg gttcctaatt tccacgcatc caccgaagct    1980
gtgcgccgag tccttcccac tgaagtcact cacatcgatg cgcgatttaa cgtgtcccgc    2040
gttgcagtga tgatcgttgc gttgcagcag cgtcctgatt tgctgtggga gggtactcgt    2100
gaccgtctgc accagcctta tcgtgcagaa gtgttgccta ttacctctga gtgggtaaac    2160
cgcctgcgca accgtggcta cgcggcatac ctttccggtg ccggcccaac cgccatggtg    2220
ctgtccactg agccaattcc agacaaggtt ttggaagatg ctcgtgagtc tggcattaag    2280
gtgcttgagc ttgaggttgc gggaccagtc aaggttgaag ttaaccaacc ttaggcccaa    2340
caaggaaggc ccccttcgaa tcaagaaggg ggccttatta gtgcagcaat tattcgctga    2400
acacgtgaac cttacaggtg cccggcgcgt tgagtggttt gagttccagc tggatgcggt    2460
tgttttcacc gaggctttct tggatgaatc cggcgtggat ggcgcagacg aaggctgatg    2520
ggcgtttgtc gttgaccaca aatgggcagc tgtgtagagc gagggagttt gcttcttcgg    2580
tttcggtggg gtcaaagccc atttcgcgga ggcggttaat gagcggggag agggcttcgt    2640
cgagttcttc ggcttcggcg tggttaatgc ccatgacgtg tgcccactgg gttccgatgg    2700
aaagtgcttt ggcgcggagg tcggggttgt gcattgcgtc atcgtcgaca tcgccgagca    2760
tgttggccat gagttcgatc agggtgatgt attcttttggc gacagcgcgg ttgtcgggga    2820
cgcgtgtttg gaagatgagg gaggggcggg atcctctaga cccgggattt aaatcgctag    2880
cgggctgcta aaggaagcgg aacacgtaga aagccagtcc gcagaaacgg tgctgacccc    2940
ggatgaatgt cagctactgg gctatctgga caagggaaaa cgcaagcgca aagagaaagc    3000
aggtagcttg cagtgggctt acatggcgat agctagactg gcggttttta tggacagcaa    3060
gcgaaccgga attgccagct ggggcgccct ctggtaaggt tgggaagccc tgcaaagtaa    3120
actggatggc tttcttgccg ccaaggatct gatggcgcag gggatcaaga tctgatcaag    3180
agacaggatg aggatcgttt cgcatgattg aacaagatgg attgcacgca ggttctccgg    3240
ccgcttgggt ggagaggcta ttcggctatg actgggcaca acagacaatc ggctgctctg    3300
atgccgccgt gttccggctg tcagcgcagg ggcgcccggt tctttttgtc aagaccgacc    3360
tgtccggtgc cctgaatgaa ctgcaggacg aggcagcgcg gctatcgtgg ctggccacga    3420
cgggcgttcc ttgcgcagct gtgctcgacg ttgtcactga agcgggaagg gactggctgc    3480
tattgggcga agtgccgggg caggatctcc tgtcatctca ccttgctcct gccgagaaag    3540
tatccatcat ggctgatgca atgcggcggc tgcatacgct tgatccggct acctgcccat    3600
tcgaccacca agcgaaacat cgcatcgagc gagcacgtac tcggatggaa gccggtcttg    3660
tcgatcagga tgatctggac gaagagcatc aggggctcgc gccagccgaa ctgttcgcca    3720
ggctcaaggc gcgcatgccc gacggcgagg atctcgtcgt gacccatggc gatgcctgct    3780
```

```
tgccgaatat catggtggaa aatggccgct tttctggatt catcgactgt ggccggctgg   3840
gtgtggcgga ccgctatcag gacatagcgt tggctacccg tgatattgct gaagagcttg   3900
gcggcgaatg ggctgaccgc ttcctcgtgc tttacggtat cgccgctccc gattcgcagc   3960
gcatcgcctt ctatcgcctt cttgacgagt tcttctgagc gggactctgg ggttcgaaat   4020
gaccgaccaa gcgacgccca acctgccatc acgagatttc gattccaccg ccgccttcta   4080
tgaaaggttg ggcttcggaa tcgttttccg ggacgccggc tggatgatcc tccagcgcgg   4140
ggatctcatg ctggagttct tcgcccacgc tagcggcgcg ccggccggcc cggtgtgaaa   4200
taccgcacag atgcgtaagg agaaaatacc gcatcaggcg ctcttccgct tcctcgctca   4260
ctgactcgct gcgctcggtc gttcggctgc ggcgagcggt atcagctcac tcaaaggcgg   4320
taatacggtt atccacagaa tcaggggata acgcaggaaa gaacatgtga gcaaaaggcc   4380
agcaaaaggc caggaaccgt aaaaaggccg cgttgctggc gtttttccat aggctccgcc   4440
cccctgacga gcatcacaaa aatcgacgct caagtcagag gtggcgaaac ccgacaggac   4500
tataaagata ccaggcgttt ccccctggaa gctccctcgt gcgctctcct gttccgaccc   4560
tgccgcttac cggatacctg tccgcctttc tcccttcggg aagcgtggcg ctttctcata   4620
gctcacgctg taggtatctc agttcggtgt aggtcgttcg ctccaagctg ggctgtgtgc   4680
acgaaccccc cgttcagccc gaccgctgcg ccttatccgg taactatcgt cttgagtcca   4740
acccggtaag acacgactta tcgccactgg cagcagccac tggtaacagg attagcagag   4800
cgaggtatgt aggcggtgct acagagttct tgaagtggtg gcctaactac ggctacacta   4860
gaaggacagt atttggtatc tgcgctctgc tgaagccagt taccttcgga aaaagagttg   4920
gtagctcttg atccggcaaa caaaccaccg ctggtagcgg tggtttttttt gtttgcaagc   4980 agcagattac gcgcagaaaa aaaggatctc aagaagatcc tttgatcttt tctacggggt   5040
ctgacgctca gtggaacgaa aactcacgtt aagggatttt ggtcatgaga ttatcaaaaa   5100
ggatcttcac ctagatcctt ttaaaggccg ccgcggccg ccatcggcat tttcttttgc   5160 gttttttatttt gttaactgtt aattgtcctt gttcaaggat gctgtctttg acaacagatg   5220
ttttcttgcc tttgatgttc agcaggaagc tcggcgcaaa cgttgattgt ttgtctgcgt   5280
agaatcctct gtttgtcata tagcttgtaa tcacgacatt gtttcctttc gcttgaggta   5340
cagcgaagtg tgagtaagta aaggttacat cgttaggatc aagatccatt tttaacacaa   5400
ggccagtttt gttcagcggc ttgtatgggc cagttaaaga attagaaaca taaccaagca   5460
tgtaaatatc gttagacgta atgccgtcaa tcgtcatttt tgatccgcgg gagtcagtga   5520
acaggtacca tttgccgttc attttaaaga cgttcgcgcg ttcaatttca tctgttactg   5580
tgttagatgc aatcagcggt ttcatcactt ttttcagtgt gtaatcatcg tttagctcaa   5640
tcataccgag agcgccgttt gctaactcag ccgtgcgttt tttatcgctt gcagaagtt    5700 tttgactttc ttgacggaag aatgatgtgc ttttgccata gtatgctttg ttaaataaag   5760
attcttcgcc ttggtagcca tcttcagttc cagtgtttgc ttcaaatact aagtatttgt   5820
ggcctttatc ttctacgtag tgaggatctc tcagcgtatg gttgtcgcct gagctgtagt   5880
tgccttcatc gatgaactgc tgtacatttt gatacgtttt ccgtcaccg tcaaagattg    5940 atttataatc ctctacaccg ttgatgttca aagagctgtc tgatgctgat acgttaactt   6000
gtgcagttgt cagtgtttgt ttgccgtaat gttaccgga gaaatcagtg tagaataaac    6060 ggattttttcc gtcagatgta aatgtggctg aacctgacca ttcttgtgtt tggtcttta    6120 ggatagaatc attttgcatcg aatttgtcgc tgtctttaaa gacgcggcca gcgttttttcc 6180
```

```
agctgtcaat agaagtttcg ccgactttt gatagaacat gtaaatcgat gtgtcatccg   6240 cattttagg atctccggct aatgcaaaga cgatgtggta gccgtgatag tttgcgacag    6300
tgccgtcagc gttttgtaat ggccagctgt cccaaacgtc caggccttt gcagaagaga   6360 tattttaat tgtggacgaa tcaaattcag aaacttgata ttttcatt ttttgctgtt    6420 cagggatttg cagcatatca tggcgtgtaa tatgggaaat gccgtatgtt tccttatatg   6480
gcttttggtt cgtttctttc gcaaacgctt gagttgcgcc tcctgccagc agtgcggtag   6540
taaaggttaa tactgttgct tgttttgcaa acttttgat gttcatcgtt catgtctcct    6600 tttatgta ctgtgttagc ggtctgcttc ttccagcct cctgtttgaa gatggcaagt    6660
tagttacgca caataaaaaa agacctaaaa tatgtaaggg gtgacgccaa agtatacact   6720 ttgccctta cacattttag gtcttgcctg ctttatcagt aacaaacccg cgcgatttac   6780
ttttcgacct cattctatta gactctcgtt tggattgcaa ctggtctatt ttcctctttt   6840
gtttgataga aaatcataa aggatttgca gactacgggc ctaagaact aaaaaatcta   6900 tctgttctt tcattctct gtattttta tagtttctgt tgcatgggca taaagttgcc    6960 ttttaatca caattcagaa aatatcataa tatctcattt cactaaataa tagtgaacgg   7020
caggtatatg tgatgggtta aaaaggatcg gcggccgctc gatttaaatc              7070

<210> SEQ ID NO 3
<211> LENGTH: 8766
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 3
tcgagaggcc tgacgtcggg cccggtacca cgcgtcatat gactagttcg gacctaggga     60
tatcgtcgac atcgatgctc ttctgcgtta attaacaatt gggatctctc aactaatgca    120
gcgatgcgtt cttccagaa tgctttcatg acagggatgc tgtcttgatc aggcaggcgt    180
ctgtgctgga tgccgaagct ggattattg tcgccttgg aggtgaagtt gacgctcact    240
cgagaatcat cggccaacca tttggcattg aatgttctag gttcggaggc ggaggttttc    300
tcaattagtg cgggatcgag ccactgcgcc gcaggtcat cgtctccgaa gagcttccac    360 acttttcga ccggcaggtt aagggttttg gaggcattgg ccgcgaaccc atcgctggtc    420
atcccgggtt tgcgcatgcc acgttcgtat tcataaccaa tcgcgatgcc ttgagcccac    480
cagccactga catcaaagtt gtccacgatg tgctttgcga tgtgggtgtg agtccaagag    540 gtggcttta cgtcgtcaag caattttagc cactcttccc acggctttcc ggtgccgttg    600
aggatagctt caggggacat gcctggtgtt gagccttgcg gagtggagtc agtcatgcga    660
ccgagactag tggcgctttg ggtaccgggc cccccctcga ggtcgagcgg cttaaagttt    720
ggctgccatg tgaatttta gcaccctcaa cagttgagtg ctggcactct cggggtaga    780 gtgccaaata ggttgtttga cacacagttg ttcacccgcg acgacggctg tgctggaaac    840
ccacaaccgg cacacacaaa atttttctca tggagggatt catcatgtcg acttcagtta    900
cttcaccagc ccacaacaac gcacattcct ccgaattttt ggatgcgttg caaaccatg    960 tgttgatcgg cgacggcgcc atgggcaccc agctccaagg ctttgacctg acgtggaaa   1020 aggattttcct tgatctggag gggtgtaatg agattctcaa cgacaccgc cctgatgtgt   1080 tgaggcagat tcaccgcgcc tactttgagg cgggagctga cttggttgag accaatactt   1140
```

```
ttggttgcaa cctgccgaac ttggcggatt atgacatcgc tgatcgttgc cgtgagcttg   1200
cctacaaggg cactgcagtg gctagggaag tggctgatga gatggggccg ggccgaaacg   1260
gcatgcggcg tttcgtggtt ggttccctgg gacctggaac gaagcttcca tcgctgggcc   1320
atgcaccgta tgcagatttg cgtgggcact acaaggaagc agcgcttggc atcatcgacg   1380
gtggtggcga tgccttttttg attgagactg ctcaggactt gcttcaggtc aaggctgcgg   1440
ttcacggcgt tcaagatgcc atggctgaac ttgatacatt cttgcccatt atttgccacg   1500
tcaccgtaga gaccaccggc accatgctca tgggttctga gatcggtgcc gcgttgacag   1560
cgctgcagcc actgggtatc gacatgattg gtctgaactg cgccaccggc ccagatgaga   1620
tgagcgagca cctgcgttac ctgtccaagc acgccgatat tcctgtgtcg gtgatgccta   1680
acgcaggtct tcctgtcctg ggtaaaaacg gtgcagaata cccacttgag gctgaggatt   1740
tggcgcaggc gctggctgga ttcgtctccg aatatggcct gtccatggtg gtggttgtt    1800
gtggcaccac acctgagcac atccgtgcgg tccgcgatgc ggtggttggt gttccagagc   1860
aggaaacctc cacactgacc aagatccctg caggccctgt tgagcaggcc tcccgcgagg   1920
tggagaaaga ggactccgtc gcgtcgctgt acacctcggt gccattgtcc caggaaaccg   1980
gcatttccat gatcggtgag cgcaccaact ccaacggttc caaggcattc cgtgaggcaa   2040
tgctgtctgg cgattgggaa aagtgtgtgg atattgccaa gcagcaaacc cgcgatggtg   2100
cacacatgct ggatctttgt gtggattacg tgggacgaga cggcaccgcc gatatggcga   2160
ccttggcagc acttcttgct accagctcca ctttgccaat catgattgac tccaccgagc   2220
cagaggttat tcgcacaggc cttgagcact gggtggacg aagcatcgtt aactccgtca    2280
actttgaaga cggcgatggc cctgagtccc gctaccagcg catcatgaaa ctggtaaagc   2340
agcacggtgc ggccgtggtt gcgctgacca ttgatgagga aggccaggca cgtaccgctg   2400
agcacaaggt gcgcattgct aaacgactga ttgacgatat caccggcagc tacggcctgg   2460
atatcaaaga catcgttgtg gactgcctga ccttcccgat ctctactggc caggaagaaa   2520
ccaggcgaga tggcattgaa accatcgaag ccatccgcga gctgaagaag ctctacccag   2580
aaatccacac cacccctgggt ctgtccaata tttccttcgg cctgaaccct gctgcacgcc   2640
aggttcttaa ctctgtgttc ctcaatgagt gcattgaggc tggtctggac tctgcgattg   2700
cgcacagctc caagattttg ccgatgaacc gcattgatga tcgccagcgc gaagtggcgt   2760
tggatatggt ctatgatcgc cgcaccgagg attacgatcc gctgcaggaa ttcatgcagc   2820
tgtttgaggg cgtttctgct gccgatgcca aggatgctcg cgctgaacag ctggccgcta   2880
tgcctttgtt tgagcgtttg gcacagcgca tcatcgacgg cgataagaat ggccttgagg   2940
atgatctgga agcaggcatg aaggagaagt ctcctattgc gatcatcaac gaggaccttc   3000
tcaacggcat gaagaccgtg ggtgagctgt ttggttccgg acagatgcag ctgccattcg   3060
tgctgcaatc ggcagaaacc atgaaaactg cggtggccta tttggaaccg ttcatggaag   3120
aggaagcaga agctaccgga tctgcgcagg cagagggcaa gggcaaaatc gtcgtggcca   3180
ccgtcaaggg tgacgtgcac gatatcggca agaacttggt ggacatcatt ttgtccaaca   3240
acggttacga cgtggtgaac ttgggcatca agcagccact gtccgccatg ttggaagcag   3300
cggaagaaca caaagcagac gtcatcggca tgtcgggact tcttgtgaag tccaccgtgg   3360
tgatgaagga aaaccttgag gagatgaaca acgccggcgc atccaattac ccagtcattt   3420
tgggtggcgc tgcgctgacg cgtacctacg tggaaaacga tctcaacgag gtgtacaccg   3480
gtgaggtgta ctacgcccgt gatgctttcg agggcctgcg cctgatggat gaggtgatgg   3540
```

```
cagaaaagcg tggtgaagga cttgatccca actcaccaga agctattgag caggcgaaga    3600
agaaggcgga acgtaaggct cgtaatgagc gttcccgcaa gattgccgcg gagcgtaaag    3660
ctaatgcggc tcccgtgatt gttccggagc gttctgatgt ctccaccgat actccaaccg    3720
cggcaccacc gttctgggga acccgcattg tcaagggtct gcccttggcg gagttcttgg    3780
gcaaccttga tgagcgcgcc ttgttcatgg ggcagtgggg tctgaaatcc acccgcggca    3840
acgagggtcc aagctatgag gatttggtgg aaactgaagg ccgaccacgc ctgcgctact    3900
ggctggatcg cctgaagtct gagggcattt tggaccacgt ggccttggtg tatggctact    3960
tcccagcggt cgcggaaggc gatgacgtgg tgatcttgga atccccggat ccacacgcag    4020
ccgaacgcat gcgctttagc ttcccacgcc agcagcgcgg caggttcttg tgcatcgcgg    4080
atttcattcg cccacgcgag caagctgtca aggacgccaa agtggacgtc atgccattcc    4140
agctggtcac catgggtaat cctattgctg atttcgccaa cgagttgttc gcagccaatg    4200
aataccgcga gtacttggaa gttcacggca tcggcgtgca gctcaccgaa gcattggccg    4260
agtactggca ctcccgagtg cgcagcgaac tcaagctgaa cgacggtgga tctgtcgctg    4320
attttgatcc agaagacaag accaagttct tcgacctgga ttaccgcggc gcccgcttct    4380
cctttggtta cggttcttgc cctgatctgg aagaccgcgc aaagctggtg gaattgctcg    4440
agccaggccg tatcggcgtg gagttgtccg aggaactcca gctgcaccca gagcagtcca    4500
cagacgcgtt tgtgctctac cacccagagg caaagtactt taacgtctaa tctagacccg    4560
ggatttaaat cgctagcggg ctgctaaagg aagcggaaca cgtagaaagc cagtccgcag    4620
aaacggtgct gaccccggat gaatgtcagc tactgggcta tctggacaag ggaaaacgca    4680
agcgcaaaga gaaagcaggt agcttgcagt gggcttacat ggcgatagct agactgggcg    4740
gttttatgga cagcaagcga accggaattg ccagctgggg cgccctctgg taaggttggg    4800
aagccctgca aagtaaactg gatggctttc ttgccgccaa ggatctgatg gcgcagggga    4860
tcaagatctg atcaagagac aggatgagga tcgtttcgca tgattgaaca agatggattg    4920
cacgcaggtt ctccgccgcc ttgggtggag aggctattcg gctatgactg gcacaacag    4980
acaatcggct gctctgatgc cgccgtgttc ggctgtcag cgcaggggcg cccggttctt    5040
tttgtcaaga ccgacctgtc cggtgccctg aatgaactgc aggacgaggc agcgcggcta    5100
tcgtggctgg ccacgacggg cgttccttgc gcagctgtgc tcgacgttgt cactgaagcg    5160
ggaagggact ggctgctatt gggcgaagtg ccggggcagg atctcctgtc atctcaccttt   5220
gctcctgccg agaaagtatc catcatggct gatgcaatgc ggcggctgca tacgcttgat    5280
ccggctacct gcccattcga ccaccaagcg aaacatcgca tcgagcgagc acgtactcgg    5340
atggaagccg gtcttgtcga tcaggatgat ctggacgaag agcatcaggg gctcgcgcca    5400
gccgaactgt tcgccaggct caaggcgcgc atgcccgacg gcgaggatct cgtcgtgacc    5460
catggcgatg cctgcttgcc gaatatcatg gtggaaaatg gccgcttttc tggattcatc    5520
gactgtggcc ggctgggtgt ggcggaccgc tatcaggaca tagcgttggc tacccgtgat    5580
attgctgaag agcttggcgg cgaatgggct gaccgcttcc tcgtgcttta cggtatcgcc    5640
gctcccgatt cgcagcgcat cgccttctat cgccttcttg acgagttctt ctgagcggga    5700
ctctggggtt cgaaatgacc gaccaagcga cgcccaacct gccatcacga tttcgatt     5760
ccaccgccgc cttctatgaa aggttgggct tcggaatcgt tttccgggac gccggctgga    5820
tgatcctcca gcgcggggat ctcatgctgg agttcttcgc ccacgctagc ggcgcgccgg    5880
ccggcccggt gtgaaatacc gcacagatgc gtaaggagaa aataccgcat caggcgctct    5940
```

-continued

```
tccgcttcct cgctcactga ctcgctgcgc tcggtcgttc ggctgcggcg agcggtatca    6000
gctcactcaa aggcggtaat acggttatcc acagaatcag gggataacgc aggaaagaac    6060
atgtgagcaa aaggccagca aaaggccagg aaccgtaaaa aggccgcgtt gctggcgttt    6120
ttccataggc tccgccccc tgacgagcat cacaaaaatc gacgctcaag tcagaggtgg     6180
cgaaacccga caggactata aagataccag gcgtttcccc ctggaagctc cctcgtgcgc    6240
tctcctgttc cgaccctgcc gcttaccgga tacctgtccg cctttctccc ttcgggaagc    6300
gtggcgcttt ctcatagctc acgctgtagg tatctcagtt cggtgtaggt cgttcgctcc    6360
aagctgggct gtgtgcacga accccccgtt cagcccgacc gctgcgcctt atccggtaac    6420
tatcgtcttg agtccaaccc ggtaagacac gacttatcgc cactggcagc agccactggt    6480
aacaggatta gcagagcgag gtatgtaggc ggtgctacag agttcttgaa gtggtggcct    6540
aactacggct acactagaag gacagtattt ggtatctgcg ctctgctgaa gccagttacc    6600
ttcggaaaaa gagttggtag ctcttgatcc ggcaaacaaa ccaccgctgg tagcggtggt    6660
ttttttgttt gcaagcagca gattacgcgc agaaaaaaag gatctcaaga agatcctttg    6720
atctttccta cggggtctga cgctcagtgg aacgaaaact cacgttaagg gattttggtc    6780
atgagattat caaaaaggat cttcacctag atcctttta aggccggccg cggccgccat    6840
cggcattttc ttttgcgttt ttatttgtta actgttaatt gtccttgttc aaggatgctg    6900
tctttgacaa cagatgtttt cttgcctttg atgttcagca ggaagctcgg cgcaaacgtt    6960
gattgtttgt ctgcgtagaa tcctctgttt gtcatatagc ttgtaatcac gacattgttt    7020
cctttcgctt gaggtacagc gaagtgtgag taagtaaagg ttacatcgtt aggatcaaga    7080
tccattttta acacaaggcc agttttgttc agcggcttgt atgggccagt taaagaatta    7140
gaaacataac caagcatgta aatatcgtta gacgtaatgc cgtcaatcgt cattttgat    7200 ccgcggagt cagtgaacag gtaccatttg ccgttcattt taaagacgtt cgcgcgttca    7260
atttcatctg ttactgtgtt agatgcaatc agcggtttca tcactttttt cagtgtgtaa    7320
tcatcgttta gctcaatcat accgagagcg ccgtttgcta actcagccgt gcgttttta    7380 tcgcttttgca gaagttttg acttctttga cggaagaatg atgtgctttt gccatagtat    7440
gctttgttaa ataaagattc ttcgccttgg tagccatctt cagttccagt gtttgcttca    7500
aatactaagt atttgtggcc tttatcttct acgtagtgag gatctctcag cgtatggttg    7560
tcgcctgagc tgtagttgcc ttcatcgatg aactgctgta cattttgata cgttttccg    7620 tcaccgtcaa agattgattt ataatcctct acaccgttga tgttcaaaga gctgtctgat    7680
gctgatacgt taacttgtgc agttgtcagt gtttgtttgc cgtaatgttt accggagaaa    7740
tcagtgtaga ataaacggat ttttccgtca gatgtaaatg tggctgaacc tgaccattct    7800
tgtgtttggt cttttaggat agaatcattt gcatcgaatt tgtcgctgtc tttaaagacg    7860
cggccagcgt ttttccagct gtcaatagaa gtttcgccga cttttttgata gaacatgtaa    7920 atcgatgtgt catccgcatt tttaggatct ccggctaatg caaagacgat gtggtagccg    7980
tgatagtttg cgacagtgcc gtcagcgttt tgtaatggcc agctgtccca aacgtccagg    8040
ccttttgcag aagagatatt tttaattgtg gacgaatcaa attcagaaac ttgatatttt    8100
tcattttttt gctgttcagg gatttgcagc atatcatggc gtgtaatatg ggaaatgccg    8160
tatgtttcct tatatggctt ttggttcgtt tctttcgcaa acgcttgagt tgcgcctcct    8220
gccagcagtg cggtagtaaa ggttaatact gttgcttgtt ttgcaaactt tttgatgttc    8280
atcgttcatg tctcctttttt tatgtactgt gttagcggtc tgcttcttcc agccctcctg    8340
```

| | |
|---|---|
| tttgaagatg gcaagttagt tacgcacaat aaaaaaagac ctaaaatatg taaggggtga | 8400 |
| cgccaaagta tacactttgc cctttacaca ttttaggtct tgcctgcttt atcagtaaca | 8460 |
| aacccgcgcg atttactttt cgacctcatt ctattagact ctcgtttgga ttgcaactgg | 8520 |
| tctatttttcc tcttttgttt gatagaaaat cataaaagga tttgcagact acgggcctaa | 8580 |
| agaactaaaa aatctatctg tttcttttca ttctctgtat ttttttatagt ttctgttgca | 8640 |
| tgggcataaa gttgccttttt taatcacaat tcagaaaata tcataatatc tcatttcact | 8700 |
| aaataatagt gaacggcagg tatatgtgat gggttaaaaa ggatcggcgg ccgctcgatt | 8760 |
| taaatc | 8766 |

<210> SEQ ID NO 4
<211> LENGTH: 7070
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 4

| | |
|---|---|
| tcgagaggcc tgacgtcggg cccggtacca cgcgtcatat gactagttgg agaatcatga | 60 |
| cctcagcatc tgccccaagc tttaaccccg gcaagggtcc cggctcagca gtcggaattg | 120 |
| cccttttagg attcggaaca gtcggcactg aggtgatgcg tctgatgacc gagtacggtg | 180 |
| atgaacttgc gcaccgcatt ggtggcccac tggaggttcg tggcattgct gtttctgata | 240 |
| tctcaaagcc acgtgaaggc gttgcacctg agctgctcac tgaggacgct tttgcactca | 300 |
| tcgagcgcga ggatgttgac atcgtcgttg aggttatcgg cggcattgag tacccacgtg | 360 |
| aggtagttct cgcagctctg aaggccggca agtctgttgt taccgccaat aaggctcttg | 420 |
| ttgcagctca ctctgctgag cttgctgatg cagcggaagc cgcaaacgtt gacctgtact | 480 |
| tcgaggctgc tgttgcaggc gcaattccag tggttggccc actgcgtcgc tcccctggctg | 540 |
| gcgatcagat ccagtctgtg atgggcatcg ttaacggcac caccaacttc atcttggacg | 600 |
| ccatggattc caccggcgct gactatgcag attctttggc tgaggcaact cgtttgggtt | 660 |
| acgccgaagc tgatccaact gcagacgtcg aaggccatga cgccgcatcc aaggctgcaa | 720 |
| ttttggcatc catcgctttc cacacccgtg ttaccgcgga tgatgtgtac tgcgaaggta | 780 |
| tcagcaacat cagcgctgcc gacattgagg cagcacagca ggcaggccac accatcaagt | 840 |
| tgttggccat ctgtgagaag ttcaccaaca aggaaggaaa gtcggctatt tctgctcgcg | 900 |
| tgcacccgac tctattacct gtgtcccacc cactggcgtc ggtaaacaag tcctttaatg | 960 |
| caatctttgt tgaagcagaa gcagctggtc gcctgatgtt ctacgaaaac ggtgcaggtg | 1020 |
| gcgcgccaac cgcgtctgct gtgcttggcg acgtcgttgg tgccgcacga aacaaggtgc | 1080 |
| acggtggccg tgctccaggt gagtccacct acgctaacct gccgatcgct gatttcggtg | 1140 |
| agaccaccac tcgttaccac ctcgacatgg atgtggaaga tcgcgtgggg gttttggctg | 1200 |
| aattggctag cctgttctct gagcaaggaa tcttcctgcg tacaatccga caggaagagc | 1260 |
| gcgatgatga tgcacgtctg atcgtggtca cccactctgc gctggaatct gatctttccc | 1320 |
| gcaccgttga actgctgaag gctaagcctg ttgttaaggc aatcaacagt gtgatccgcc | 1380 |
| tcgaaaggga ctaattttac tgacatggca attgaactga acgtcggtcg taaggttacc | 1440 |
| gtcacggtac ctggatcttc tgcaaacctc ggacctggct ttgacacttt aggtttggca | 1500 |
| ctgtcggtat acgacactgt cgaagtggaa attattccat ctggcttgga agtggaagtt | 1560 |
| tttggcgaag gccaaggcga agtccctctt gatggctccc acctggtggt taaagctatt | 1620 |

```
cgtgctggcc tgaaggcagc tgacgctgaa gttcctggat tgcgagtggt gtgccacaac    1680
aacattccgc agtctcgtgg tcttggctcc gctgctgcag cggcggttgc tggtgttgct    1740
gcagctaatg gtttggcgga tttcccgctg actcaagagc agattgttca gttgtcctct    1800
gcctttgaag gccacccaga taatgctgcg gcttctgtgc tgggtggagc agtggtgtcg    1860
tggacaaatc tgtctatcga cggcaagagc cagccacagt atgctgctgt accacttgag    1920
gtgcaggaca atattcgtgc gactgcgctg gttcctaatt ccacgcatc caccgaagct     1980 gtgcgccgag tccttcccac tgaagtcact cacatcgatg cgcgatttaa cgtgtcccgc    2040
gttgcagtga tgatcgttgc gttgcagcag cgtcctgatt tgctgtggga gggtactcgt    2100
gaccgtctgc accagcctta tcgtgcagaa gtgttgccta ttacctctga gtgggtaaac    2160
cgcctgcgca accgtggcta cgcggcatac ctttccggtg ccggcccaac cgccatggtg    2220
ctgtccactg agccaattcc agacaaggtt ttggaagatg ctcgtgagtc tggcattaag    2280
gtgcttgagc ttgaggttgc gggaccagtc aaggttgaag ttaaccaacc ttaggcccaa    2340
caaggaaggc ccccttcgaa tcaagaaggg ggccttatta gtgcagcaat tattcgctga    2400
acacgtgaac cttacaggtg cccggcgcgt tgagtggttt gagttccagc tggatgcggt    2460
tgttttcacc gaggctttct tggatgaatc cggcgtggat ggcgcagacg aaggctgatg    2520
ggcgtttgtc gttgaccaca atgggcagc tgtgtagagc gagggagttt gcttcttcgg     2580
tttcggtggg gtcaaagccc atttcgcgga ggcggttaat gagcggggag agggcttcgt    2640
cgagttcttc ggcttcggcg tggttaatgc ccatgacgtg tgcccactgg gttccgatgg    2700
aaagtgcttt ggcgcggagg tcggggttgt gcattgcgtc atcgtcgaca tcgccgagca    2760
tgttggccat gagttcgatc agggtgatgt attctttggc gacagcgcgg ttgtcgggga    2820
cgcgtgtttg gaagatgagg gagggcggg atcctctaga cccgggattt aaatcgctag     2880
cgggctgcta aggaagcgg aacacgtaga aagccagtcc gcagaaacgg tgctgacccc      2940
ggatgaatgt cagctactgg gctatctgga caagggaaaa cgcaagcgca aagagaaagc    3000
aggtagcttg cagtgggctt acatggcgat agctagactg gcggttttta tggacagcaa    3060
gcgaaccgga attgccagct ggggcgccct ctggtaaggt tgggaagccc tgcaaagtaa    3120
actggatggc tttcttgccg ccaaggatct gatggcgcag gggatcaaga tctgatcaag    3180
agacaggatg aggatcgttt cgcatgattg aacaagatgg attgcacgca ggttctccgg    3240
ccgcttgggt ggagaggcta ttcggctatg actgggcaca acagacaatc ggctgctctg    3300
atgccgccgt gttccggctg tcagcgcagg gcgcccggt tcttttttgtc aagaccgacc     3360 tgtccggtgc cctgaatgaa ctgcaggacg aggcagcgcg gctatcgtgg ctggccacga    3420
cgggcgttcc ttgcgcagct gtgctcgacg ttgtcactga agcgggaagg gactggctgc    3480
tattgggcga agtgccgggg caggatctcc tgtcatctca ccttgctcct gccgagaaag    3540
tatccatcat ggctgatgca atgcggcggc tgcatacgct tgatccggct acctgcccat    3600
tcgaccacca agcgaaacat cgcatcgagc gagcacgtac tcggatggaa gccggtcttg    3660
tcgatcagga tgatctggac gaagagcatc agggctcgc gccagccgaa ctgttcgcca     3720
ggctcaaggc gcgcatgccc gacggcgagg atctcgtcgt gacccatggc gatgcctgct    3780
tgccgaatat catggtggaa aatggccgct tttctggatt catcgactgt ggccggctgg    3840
gtgtggcgga ccgctatcag gacatagcgt tggctacccg tgatattgct gaagagcttg    3900
gcggcgaatg ggctgaccgc ttcctcgtgc tttacggtat cgccgctccc gattcgcagc    3960
gcatcgcctt ctatcgcctt cttgacgagt tcttctgagc gggactctgg ggttcgaaat    4020
```

```
gaccgaccaa gcgacgccca acctgccatc acgagatttc gattccaccg ccgccttcta    4080
tgaaaggttg ggcttcggaa tcgttttccg ggacgccggc tggatgatcc tccagcgcgg    4140
ggatctcatg ctggagttct cgcccacgc tagcggcgcg ccggccggcc cggtgtgaaa     4200
taccgcacag atgcgtaagg agaaaatacc gcatcaggcg ctcttccgct tcctcgctca    4260
ctgactcgct gcgctcggtc gttcggctgc ggcgagcggt atcagctcac tcaaaggcgg    4320
taatacggtt atccacagaa tcaggggata acgcaggaaa gaacatgtga gcaaaaggcc    4380
agcaaaaggc caggaaccgt aaaaaggccg cgttgctggc gtttttccat aggctccgcc    4440
cccctgacga gcatcacaaa aatcgacgct caagtcagag gtggcgaaac ccgacaggac    4500
tataaagata ccaggcgttt ccccctggaa gctccctcgt gcgctctcct gttccgaccc    4560
tgccgcttac cggatacctg tccgcctttc tcccttcggg aagcgtggcg ctttctcata    4620
gctcacgctg taggtatctc agttcggtgt aggtcgttcg ctccaagctg ggctgtgtgc    4680
acgaaccccc cgttcagccc gaccgctgcg ccttatccgg taactatcgt cttgagtcca    4740
acccggtaag acacgactta tcgccactgg cagcagccac tggtaacagg attagcagag    4800
cgaggtatgt aggcggtgct acagagttct tgaagtggtg gcctaactac ggctacacta    4860
gaaggacagt atttggtatc tgcgctctgc tgaagccagt taccttcgga aaaagagttg    4920
gtagctcttg atccggcaaa caaaccaccg ctggtagcgg tggtttttt gtttgcaagc     4980 agcagattac gcgcagaaaa aaaggatctc aagaagatcc tttgatcttt tctacggggt    5040
ctgacgctca gtggaacgaa aactcacgtt aagggatttt ggtcatgaga ttatcaaaaa    5100
ggatcttcac ctagatcctt ttaaaggccg gccgcggccg ccatcggcat tttcttttgc    5160 gttttattt gttaactgtt aattgtcctt gttcaaggat gctgtctttg acaacagatg     5220
ttttcttgcc tttgatgttc agcaggaagc tcggcgcaaa cgttgattgt ttgtctgcgt    5280
agaatcctct gtttgtcata tagcttgtaa tcacgacatt gttttccttc gcttgaggta    5340
cagcgaagtg tgagtaagta aaggttacat cgttaggatc aagatccatt tttaacacaa    5400
ggccagtttt gttcagcggc ttgtatgggc cagttaaaga attagaaaca taaccaagca    5460
tgtaaatatc gttagacgta atgccgtcaa tcgtcatttt tgatccgcgg gagtcagtga    5520
acaggtacca tttgccgttc attttaaaga cgttcgcgcg ttcaatttca tctgttactg    5580
tgttagatgc aatcagcggt ttcatcactt ttttcagtgt gtaatcatcg tttagctcaa    5640
tcataccgag agcgccgttt gctaactcag ccgtgcgttt tttatcgctt tgcagaagtt    5700
tttgactttc ttgacggaag aatgatgtgc ttttgccata gtatgctttg ttaaataaag    5760
attcttcgcc ttggtagcca tcttcagttc cagtgtttgc ttcaaatact aagtatttgt    5820
ggcctttatc ttctacgtag tgaggatctc tcagcgtatg gttgtcgcct gagctgtagt    5880
tgccttcatc gatgaactgc tgtacatttt gatacgtttt tccgtcaccg tcaaagattg    5940
atttataatc ctctacaccg ttgatgttca aagagctgtc tgatgctgat acgttaactt    6000
gtgcagttgt cagtgtttgt ttgccgtaat gtttaccgga gaaatcagtg tagaataaac    6060 ggattttttcc gtcagatgta aatgtggctg aacctgacca ttcttgtgtt tggtcttta    6120 ggatagaatc atttgcatcg aatttgtcgc tgtctttaaa gacgcggcca gcgttttcc    6180 agctgtcaat agaagtttcg ccgactttt gatagaacat gtaaatcgat gtgtcatccg    6240
catttttagg atctccggct aatgcaaaga cgatgtggta gccgtgatag tttgcgacag    6300
tgccgtcagc gttttgtaat ggccagctgt cccaaacgtc caggcctttt gcagaagaga    6360 tattttaat tgtggacgaa tcaaattcag aaacttgata tttttcattt tttgctgtt     6420
```

| | |
|---|---|
| cagggatttg cagcatatca tggcgtgtaa tatgggaaat gccgtatgtt tccttatatg | 6480 |
| gcttttggtt cgtttctttc gcaaacgctt gagttgcgcc tcctgccagc agtgcggtag | 6540 |
| taaaggttaa tactgttgct tgttttgcaa acttttttgat gttcatcgtt catgtctcct | 6600 |
| tttttatgta ctgtgttagc ggtctgcttc ttccagccct cctgtttgaa gatggcaagt | 6660 |
| tagttacgca caataaaaaa agacctaaaa tatgtaaggg gtgacgccaa agtatacact | 6720 |
| ttgccccttta cacattttag gtcttgcctg ctttatcagt aacaaacccg cgcgatttac | 6780 |
| ttttcgacct cattctatta gactctcgtt tggattgcaa ctggtctatt ttcctctttt | 6840 |
| gtttgataga aaatcataaa aggatttgca gactacgggc taaagaact aaaaaatcta | 6900 |
| tctgtttctt ttcattctct gtattttta tagtttctgt tgcatgggca taaagttgcc | 6960 |
| tttttaatca caattcagaa aatatcataa tatctcattt cactaaataa tagtgaacgg | 7020 |
| caggtatatg tgatgggtta aaaggatcg gcggccgctc gatttaaatc | 7070 |

<210> SEQ ID NO 5
<211> LENGTH: 6625
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 5

| | |
|---|---|
| tcgagaggcc tgacgtcggg cccggtaccg ttgctcgctg atctttcggc ttaacaactt | 60 |
| tgtattcaat cagtcgggca tagaaagaaa acgcaatgat ataggaacca actgccgcca | 120 |
| aaaccagcca cacagagttg attgtttcgc cacgggagaa agcgattgct ccccaaccca | 180 |
| ccgccgcgat aaccccaaag acaaggagac caacgcgggc ggtcggtgac atttaggg | 240 |
| acttcttcac gcctactgga aggtcagtag cgttgctgta caccaaatca tcgtcattga | 300 |
| tgttgtcagt ctgttttatg gtcacgatct ttactgttt ctcttcgggt cgtttcaaag | 360 |
| ccactatgcg tagaaacagc gggcagaaac agcgggcaga actgtgtgc agaaatgcat | 420 |
| gcagaaaaag gaaagttcgg ccagatgggt gtttctgtat gccgatgatc ggatctttga | 480 |
| cagctgggta tgcgacaaat caccgagagt tgttaattct taacaatgga aaagtaacat | 540 |
| tgagagatga tttataccat cctgcaccat ttagagtggg gctagtcata ccccataac | 600 |
| cctagctgta cgcaatcgat ttcaaatcag ttggaaaaag tcaagaaaat tacccgagac | 660 |
| atatgcggct taaagtttgg ctgccatgtg aattttagc accctcaaca gttgagtgct | 720 |
| ggcactctcg agggtagagt gccaaatagg ttgtttgaca cacagttgtt caccgcgac | 780 |
| gacggctgtg ctggaaaccc acaaccggca cacacaaat ttttctcatg gccgttaccc | 840 |
| tgcgaatgtc cacagggtag ctggtagttt gaaaatcaac gccgttgccc ttaggattca | 900 |
| gtaactggca cattttgtaa tgcgctagat ctgtgtgctc agtcttccag gctgcttatc | 960 |
| acagtgaaag caaaccaat tcgtggctgc gaaagtcgta gccaccacga agtccaggag | 1020 |
| gacatacaat gccaaagtac gacaattcca atgctgacca gtggggcttt gaaacccgct | 1080 |
| ccattcacgc aggccagtca gtagacgcac agaccagcgc acgaaacctt ccgatctacc | 1140 |
| aatccaccgc tttcgtgttc gactccgctg agcacgccaa gcagcgtttc gcacttgagg | 1200 |
| atctaggccc tgtttactcc cgcctcacca acccaaccgt tgaggctttg gaaaaccgca | 1260 |
| tcgcttccct cgaaggtggc gtccacgctg tagcgttctc ctccggacag gccgcaacca | 1320 |
| ccaacgccat tttgaacctg gcaggagcgg gcgaccacat cgtcacctcc ccacgcctct | 1380 |

```
acggtggcac cgagactcta ttccttatca ctcttaaccg cctgggtatc gatgtttcct    1440
tcgtggaaaa ccccgacgac cctgagtcct ggcaggcagc cgttcagcca aacaccaaag    1500
cattcttcgg cgagactttc gccaacccac aggcagacgt cctggatatt cctgcggtgg    1560
ctgaagttgc gcaccgcaac agcgttccac tgatcatcga caacaccatc gctaccgcag    1620
cgctcgtgcg cccgctcgag ctcggcgcag acgttgtcgt cgcttccctc accaagttct    1680
acaccggcaa cggctccgga ctgggcgcg tgcttatcga cggcggaaag ttcgattgga    1740
ctgtcgaaaa ggatggaaag ccagtattcc cctacttcgt cactccagat gctgcttacc    1800
acggattgaa gtacgcagac cttggtgcac cagccttcgg cctcaaggtt cgcgttggcc    1860
ttctacgcga caccggctcc accctctccg cattcaacgc atgggctgca gtccagggca    1920
tcgacaccct ttccctgcgc ctggagcgcc acaacgaaaa cgccatcaag gttgcagaat    1980
tcctcaacaa ccacgagaag gtggaaaagg ttaacttcgc aggcctgaag gattcccctt    2040
ggtacgcaac caaggaaaag cttggcctga agtacaccgg ctccgttctc accttcgaga    2100
tcaagggcgg caaggatgag gcttgggcat ttatcgacgc cctgaagcta cactccaacc    2160
ttgcaaacat cggcgatgtt cgctccctcg ttgttcaccc agcaaccacc acccattcac    2220
agtccgacga agctggcctg gcacgcgcgg gcgttaccca gtccaccgtc cgcctgtccg    2280
ttggcatcga gaccattgat gatatcatcg ctgacctcga aggcggcttt gctgcaatct    2340
agcactagtt cggacctagg gatatcgtcg acatcgatgc tcttctgcgt taattaacaa    2400
ttgggatcct ctagacccgg gatttaaatc gctagcgggc tgctaaagga agcggaacac    2460
gtagaaagcc agtccgcaga acggtgctga cccccggatg aatgtcagct actgggctat    2520
ctggacaagg gaaaacgcaa gcgcaaagag aaagcaggta gcttgcagtg gcttacatg    2580 gcgatagcta gactgggcgg ttttatggac agcaagcgaa ccggaattgc cagctggggc    2640
gccctctggt aaggttggga gccctgcaa agtaaactgg atggctttct tgccgccaag    2700
gatctgatgg cgcaggggat caagatctga tcaagagaca ggatgaggat cgtttcgcat    2760
gattgaacaa gatggattgc acgcaggttc tccggccgct tgggtggaga ggctattcgg    2820
ctatgactgg gcacaacaga caatcggctg ctctgatgcc gccgtgttcc ggctgtcagc    2880
gcaggggcgc ccggttcttt ttgtcaagac cgacctgtcc ggtgccctga atgaactgca    2940
ggacgaggca gcgcggctat cgtggctggc acgacgggc gttccttgcg cagctgtgct    3000
cgacgttgtc actgaagcgg gaagggactg gctgctattg ggcgaagtgc cggggcagga    3060
tctcctgtca tctcaccttg ctcctgccga gaaagtatcc atcatggctg atgcaatgcg    3120
gcggctgcat acgcttgatc cggctacctg cccattcgac caccaagcga acatcgcat    3180 cgagcgagca cgtactcgga tggaagccgg tcttgtcgat caggatgatc tggacgaaga    3240
gcatcagggg ctcgcgccag ccgaactgtt cgccaggctc aaggcgcgca tgcccgacgg    3300
cgaggatctc gtcgtgaccc atggcgatgc ctgcttgccg aatatcatgg tggaaaatgg    3360
ccgcttttct ggattcatcg actgtggccg gctgggtgtg gcggaccgct atcaggacat    3420
agcgttggct acccgtgata ttgctgaaga gcttggcggc gaatgggctg accgcttcct    3480
cgtgctttac ggtatcgccg ctcccgattc gcagcgcatc gccttctatc gccttcttga    3540
cgagttcttc tgagcgggac tctggggttc gaaatgaccg accaagcgac gcccaacctg    3600
ccatcacgag atttcgattc caccgccgcc ttctatgaaa ggttgggctt cggaatcgtt    3660
ttccgggacg ccggctggat gatcctccag cgcggggatc tcatgctgga gttcttcgcc    3720
cacgctagcg gcgcgccggc cggcccggtg tgaaataccg cacagatgcg taaggagaaa    3780
```

```
ataccgcatc aggcgctctt ccgcttcctc gctcactgac tcgctgcgct cggtcgttcg    3840
gctgcggcga gcggtatcag ctcactcaaa ggcggtaata cggttatcca cagaatcagg    3900
ggataacgca ggaaagaaca tgtgagcaaa aggccagcaa aaggccagga accgtaaaaa    3960
ggccgcgttg ctggcgtttt tccataggct ccgcccccct gacgagcatc acaaaaatcg    4020
acgctcaagt cagaggtggc gaaacccgac aggactataa agataccagg cgtttccccc    4080
tggaagctcc ctcgtgcgct ctcctgttcc gaccctgccg cttaccggat acctgtccgc    4140
cttctccct tcgggaagcg tggcgctttc tcatagctca cgctgtaggt atctcagttc    4200
ggtgtaggtc gttcgctcca agctgggctg tgtgcacgaa ccccccgttc agcccgaccg    4260
ctgcgcctta tccggtaact atcgtcttga gtccaacccg gtaagacacg acttatcgcc    4320
actggcagca gccactggta acaggattag cagagcgagg tatgtaggcg gtgctacaga    4380
gttcttgaag tggtggccta actacggcta cactagaagg acagtatttg gtatctgcgc    4440
tctgctgaag ccagttacct tcggaaaaag agttggtagc tcttgatccg gcaaacaaac    4500
caccgctggt agcggtggtt tttttgtttg caagcagcag attacgcgca gaaaaaaagg    4560
atctcaagaa gatcctttga tcttttctac ggggtctgac gctcagtgga acgaaaactc    4620
acgttaaggg attttggtca tgagattatc aaaaaggatc ttcacctaga tccttttaaa    4680
ggccggccgc ggccgccatc ggcatttttct tttgcgtttt tatttgttaa ctgttaattg    4740
tccttgttca aggatgctgt ctttgacaac agatgttttc ttgcctttga tgttcagcag    4800
gaagctcggc gcaaacgttg attgtttgtc tgcgtagaat cctctgtttg tcatatagct    4860
tgtaatcacg acattgtttc ctttcgcttg aggtacagcg aagtgtgagt aagtaaaggt    4920
tacatcgtta ggatcaagat ccatttttaa cacaaggcca gttttgttca gcggcttgta    4980
tgggccagtt aaagaattag aaacataacc aagcatgtaa atatcgttag acgtaatgcc    5040
gtcaatcgtc attttgatc cgcgggagtc agtgaacagg taccatttgc cgttcatttt    5100
aaagacgttc gcgcgttcaa tttcatctgt tactgtgtta gatgcaatca gcggtttcat    5160
cactttttc agtgtgtaat catcgtttag ctcaatcata ccgagagcgc cgtttgctaa    5220
ctcagccgtg cgttttttat cgctttgcag aagttttga cttcttgac ggaagaatga    5280
tgtgcttttg ccatagtatg ctttgttaaa taaagattct tcgccttggt agccatcttc    5340
agttccagtg tttgcttcaa atactaagta tttgtggcct ttatcttcta cgtagtgagg    5400
atctctcagc gtatggttgt cgcctgagct gtagttgcct tcatcgatga actgctgtac    5460
attttgatac gttttccgt caccgtcaaa gattgattta taatcctcta caccgttgat    5520
gttcaaagag ctgtctgatg ctgatacgtt aacttgtgca gttgtcagtg tttgtttgcc    5580
gtaatgttta ccgagaaat cagtgtagaa taaacggatt tttccgtcag atgtaaatgt    5640
ggctgaacct gaccattctt gtgtttggtc ttttaggata gaatcatttg catcgaattt    5700
gtcgctgtct ttaaagacgc ggccagcgtt tttccagctg tcaatagaag tttgccgac    5760
ttttgatag aacatgtaaa tcgatgtgtc atccgcattt ttaggatctc cggctaatgc    5820
aaagacgatg tggtagccgt gatagtttgc gacagtgccg tcagcgtttt gtaatggcca    5880
gctgtcccaa acgtccaggc ctttgcaga agagatattt ttaattgtgg acgaatcaaa    5940
ttcagaaact tgatattttt catttttttg ctgttcaggg atttgcagca tatcatggcg    6000
tgtaatatgg gaaatgccgt atgtttcctt atatggcttt tggttcgttt ctttcgcaaa    6060
cgcttgagtt gcgcctcctg ccagcagtgc ggtagtaaag gttaatactg ttgcttgttt    6120
tgcaaacttt ttgatgttca tcgttcatgt ctcctttttt atgtactgtg ttagcggtct    6180
```

| gcttcttcca gccctcctgt tgaagatgg caagttagtt acgcacaata aaaaagacc | 6240 |
| taaaatatgt aagggtgac gccaaagtat acactttgcc ctttacacat tttaggtctt | 6300 |
| gcctgcttta tcagtaacaa acccgcgcga tttactttc gacctcattc tattagactc | 6360 |
| tcgtttggat tgcaactggt ctattttcct cttttgtttg atagaaaatc ataaaaggat | 6420 |
| ttgcagacta cgggcctaaa gaactaaaaa atctatctgt ttcttttcat tctctgtatt | 6480 |
| ttttatagtt tctgttgcat gggcataaag ttgccttttt aatcacaatt cagaaaatat | 6540 |
| cataatatct catttcacta ataatagtg aacggcaggt atgtgatg ggttaaaaag | 6600 |
| gatcggcggc cgctcgattt aaatc | 6625 |

<210> SEQ ID NO 6
<211> LENGTH: 363
<212> TYPE: DNA
<213> ORGANISM: Artificial Sequence
<220> FEATURE:
<223> OTHER INFORMATION: Description of Artificial Sequence: Synthetic
     promoter

<400> SEQUENCE: 6

| cggcttaaag tttggctgcc atgtgaattt ttagcaccct caacagttga gtgctggcac | 60 |
| tctcgagggt agagtgccaa ataggttgtt tgacacacag ttgttcaccc gcgacgacgg | 120 |
| ctgtgctgga aacccacaac cggcacacac aaaattttc tcatggccgt taccctgcga | 180 |
| atgtccacag ggtagctggt agtttgaaaa tcaacgccgt tgcccttagg attcagtaac | 240 |
| tggcacattt tgtaatgcgc tagatctgtg tgctcagtct tccaggctgc ttatacagt | 300 |
| gaaagcaaaa ccaattcgtg gctgcgaaag tcgtagccac cacgaagtcc aggaggacat | 360 |
| aca | 363 |

<210> SEQ ID NO 7
<211> LENGTH: 6350
<212> TYPE: DNA
<213> ORGANISM: Artificial Sequence
<220> FEATURE:
<223> OTHER INFORMATION: Description of Artificial Sequence: Synthetic
     plasmid

<400> SEQUENCE: 7

| tcgagctcgg cgcagacgtt gtcgtcgctt ccctcaccaa gttctacacc ggcaacggct | 60 |
| ccggactggg cggcgtgctt atcgacggcg gaaagttcga ttggactgtc gaaaaggatg | 120 |
| gaaagccagt attcccctac ttcgtcactc cagatgctgc ttaccacgga ttgaagtacg | 180 |
| cagaccttgg tgcaccagcc ttcggcctca aggttcgcgt tggccttcta cgcgacaccg | 240 |
| gctccaccct ctccgcattc aacgcatggg ctgcagtcca gggcatcgac acccttcc | 300 |
| tgcgcctgga gcgccacaac gaaaacgcca tcaaggttgc agaattcctc aacaaccacg | 360 |
| agaaggtgga aaaggttaac ttcgcaggcc tgaaggattc cccttggtac gcaaccaagg | 420 |
| aaaagcttgg cctgaagtac accggctccg ttctcacctt cgagatcaag ggcggcaagg | 480 |
| atgaggcttg gcatttatc gacgccctga agctacactc caaccttgca acatcggcg | 540 |
| atgttcgctc cctcgttgtt cacccagcaa ccaccaccca ttcacagtcc gacgaagctg | 600 |
| gcctggcacg cgcgggcgtt acccagtcca ccgtccgcct gtccgttggc atcgagacca | 660 |
| ttgatgatat catcgctgac ctcgaaggcg gctttgctgc aatctagcac tagttcggac | 720 |
| ctagggatat cgtcgagagc tgccaattat tccgggcttg tgacccgcta cccgataaat | 780 |
| aggtcggctg aaaaatttcg ttgcaatatc aacaaaaagg cctatcattg ggaggtgtcg | 840 |

-continued

```
caccaagtac ttttgcgaag cgccatctga cggattttca aaagatgtat atgctcggtg      900
cggaaaccta cgaaaggatt ttttacccat gcccaccctc gcgccttcag gtcaacttga      960
aatccaagcg atcggtgatg tctccaccga agccggagca atcattacaa acgctgaaat     1020
cgcctatcac cgctggggtg aataccgcgt agataaagaa ggacgcagca atgtcgttct     1080
catcgaacac gccctcactg gagattccaa cgcagccgat tggtgggctg acttgctcgg     1140
tcccggcaaa gccatcaaca ctgatattta ctgcgtgatc tgtaccaacg tcatcggtgg     1200
ttgcaacggt tccaccggac ctggctccat gcatccagat ggaaatttct ggggtaatcg     1260
cttccccgcc acgtccattc gtgatcaggt aaacgccgaa aaacaattcc tcgacgcact     1320
cggcatcacc acggtcgccg cagtacttgg tggttccatg ggtggtgccc gcaccctaga     1380
gtgggccgca atgtacccag aaactgttgg cgcagctgct gttcttgcag tttctgcacg     1440
cgccagcgcc tggcaaatcg gcattcaatc cgcccaaatt aaggcgattg aaaacgacca     1500
ccactggcac gaaggcaact actacgaatc cggctgcaac ccagccaccg gactcggcgc     1560
cgcccgacgc atcgcccacc tcacctaccg tggcgaacta gaaatcgacg aacgcttcgg     1620
caccaaagcc caaagaacg aaaacccact cggtccctac cgcaagcccg accagcgctt     1680
cgccgtggaa tcctacttgg actaccaagc agacaagcta gtacagcgtt cgacgccgg     1740 ctcctacgtc ttgctcaccg acgccctcaa ccgccacgac attggtcgcg accgcggagg     1800
cctcaacaag gcactcgaat ccatcaaagt tccagtcctt gtcgcaggcg tagataccga     1860
tattttgtac ccctaccacc agcaagaaca cctctccaga aacctgggaa atctactggc     1920
aatggcaaaa atcgtatccc ctgtcggcca cgatgctttc ctcaccgaaa gccgccaaat     1980
ggatcgcatc gtgaggaact tcttcagcct catctcccca gacgaagaca cccttcgac     2040 ctacatcgag ttctacatct aacatatgac tagttcggac ctaggatat cgtcgacatc     2100 gatgctcttc tgcgttaatt aacaattggg atcctctaga cccgggattt aaatcgctag     2160
cgggctgcta aaggaagcgg aacacgtaga aagccagtcc gcagaaacgg tgctgacccc     2220
ggatgaatgt cagctactgg gctatctgga caagggaaaa cgcaagcgca aagagaaagc     2280
aggtagcttg cagtgggctt acatggcgat agctagactg ggcggtttta tggacagcaa     2340
gcgaaccgga attgccagct ggggcgccct ctggtaaggt tgggaagccc tgcaaagtaa     2400 actgatggc tttcttgccg ccaaggatct gatggcgcag gggatcaaga tctgatcaag     2460
agacaggatg aggatcgttt cgcatgattg aacaagatgg attgcacgca ggttctccgg     2520
ccgcttgggt ggagaggcta ttcggctatg actgggcaca acagacaatc ggctgctctg     2580
atgccgccgt gttccggctg tcagcgcagg ggcgcccggt tctttttgtc aagaccgacc     2640
tgtccggtgc cctgaatgaa ctgcaggacg aggcagcgcg gctatcgtgg ctggccacga     2700
cgggcgttcc ttgcgcagct gtgctcgacg ttgtcactga agcgggaagg gactggctgc     2760
tattgggcga agtgccgggg caggatctcc tgtcatctca ccttgctcct gccgagaaag     2820
tatccatcat ggctgatgca atgcggcggc tgcatacgct tgatccggct acctgcccat     2880
tcgaccacca agcgaaacat cgcatcgagc gagcacgtac tcggatggaa gccggtcttg     2940
tcgatcagga tgatctggac gaagagcatc aggggctcgc gccagccgaa ctgttcgcca     3000
ggctcaaggc gcgcatgccc gacggcgagg atctcgtcgt gacccatggc gatgcctgct     3060
tgccgaatat catggtggaa aatggccgct tttctggatt catcgactgt ggccggctgg     3120
gtgtggcgga ccgctatcag gacatagcgt tggctacccg tgatattgct gaagagcttg     3180
gcggcgaatg ggctgaccgc ttcctcgtgc tttacggtat cgccgctccc gattcgcagc     3240
```

```
gcatcgcctt ctatcgcctt cttgacgagt tcttctgagc gggactctgg ggttcgaaat   3300
gaccgaccaa gcgacgccca acctgccatc acgagatttc gattccaccg ccgccttcta   3360
tgaaaggttg ggcttcggaa tcgttttccg ggacgccggc tggatgatcc tccagcgcgg   3420
ggatctcatg ctggagttct tcgcccacgc tagcggcgcg ccggccggcc cggtgtgaaa   3480
taccgcacag atgcgtaagg agaaaatacc gcatcaggcg ctcttccgct tcctcgctca   3540
ctgactcgct gcgctcggtc gttcggctgc ggcgagcggt atcagctcac tcaaaggcgg   3600
taatacggtt atccacagaa tcaggggata acgcaggaaa gaacatgtga gcaaaaggcc   3660
agcaaaaggc caggaaccgt aaaaaggccg cgttgctggc gtttttccat aggctccgcc   3720
cccctgacga gcatcacaaa aatcgacgct caagtcagag gtggcgaaac ccgacaggac   3780
tataaagata ccaggcgttt ccccctggaa gctccctcgt gcgctctcct gttccgaccc   3840
tgccgcttac cggatacctg tccgcctttc tcccttcggg aagcgtggcg ctttctcata   3900
gctcacgctg taggtatctc agttcggtgt aggtcgttcg ctccaagctg ggctgtgtgc   3960
acgaaccccc cgttcagccc gaccgctgcg ccttatccgg taactatcgt cttgagtcca   4020
acccggtaag acacgactta tcgccactgg cagcagccac tggtaacagg attagcagag   4080
cgaggtatgt aggcggtgct acagagttct tgaagtggtg gcctaactac ggctacacta   4140
gaaggacagt atttggtatc tgcgctctgc tgaagccagt taccttcgga aaaagagttg   4200
gtagctcttg atccggcaaa caaaccaccg ctggtagcgg tggtttttttt gtttgcaagc   4260 agcagattac gcgcagaaaa aaaggatctc aagaagatcc tttgatcttt tctacggggt   4320
ctgacgctca gtggaacgaa aactcacgtt aagggatttt ggtcatgaga ttatcaaaaa   4380
ggatcttcac ctagatcctt ttaaaggccg gccgcggccg ccatcggcat tttcttttgc   4440 gttttttattt gttaactgtt aattgtcctt gttcaaggat gctgtctttg acaacagatg   4500
ttttcttgcc tttgatgttc agcaggaagc tcggcgcaaa cgttgattgt ttgtctgcgt   4560
agaatcctct gtttgtcata tagcttgtaa tcacgacatt gtttccttcc gcttgaggta   4620
cagcgaagtg tgagtaagta aaggttacat cgttaggatc aagatccatt tttaacacaa   4680
ggccagtttt gttcagcggc ttgtatgggc cagttaaaga attagaaaca taaccaagca   4740
tgtaaatatc gttagacgta atgccgtcaa tcgtcatttt tgatccgcgg gagtcagtga   4800
acaggtacca tttgccgttc attttaaaga cgttcgcgcg ttcaatttca tctgttactg   4860
tgttagatgc aatcagcggt ttcatcactt ttttcagtgt gtaatcatcg tttagctcaa   4920
tcataccgag agcgccgttt gctaactcag ccgtgcgttt tttatcgctt gcagaagtt    4980 tttgactttc ttgacggaag aatgatgtgc ttttgccata gtatgctttg ttaaataaag   5040
attcttcgcc ttggtagcca tcttcagttc cagtgtttgc ttcaaatact aagtatttgt   5100
ggcctttatc ttctacgtag tgaggatctc tcagcgtatg gttgtcgcct gagctgtagt   5160
tgccttcatc gatgaactgc tgtacatttt gatacgtttt tccgtcaccg tcaaagattg   5220
atttataatc ctctacaccg ttgatgttca aagagctgtc tgatgctgat acgttaactt   5280
gtgcagttgt cagtgtttgt ttgccgtaat gtttaccgga gaaatcagtg tagaataaac   5340
ggatttttcc gtcagatgta aatgtggctg aacctgacca ttcttgtgtt tggtctttta   5400
ggatagaatc atttgcatcg aatttgtcgc tgtctttaaa gacgcggcca gcgttttttcc   5460 agctgtcaat agaagtttcg ccgacttttt gatagaacat gtaaatcgat gtgtcatccg   5520
catttttagg atctccggct aatgcaaaga cgatgtggta gccgtgatag tttgcgacag   5580
tgccgtcagc gttttgtaat ggccagctgt cccaaacgtc caggcctttt gcagaagaga   5640
```

-continued

```
tattttttaat tgtggacgaa tcaaattcag aaacttgata tttttcattt ttttgctgtt    5700
cagggatttg cagcatatca tggcgtgtaa tatgggaaat gccgtatgtt tccttatatg    5760
gcttttggtt cgtttctttc gcaaacgctt gagttgcgcc tcctgccagc agtgcggtag    5820
taaaggttaa tactgttgct tgttttgcaa acttttgat gttcatcgtt catgtctcct     5880
tttttatgta ctgtgttagc ggtctgcttc ttccagccct cctgtttgaa gatggcaagt    5940
tagttacgca aataaaaaa agacctaaaa tatgtaaggg gtgacgccaa agtatacact     6000
ttgcccttta cacattttag gtcttgcctg ctttatcagt aacaaacccg cgcgatttac    6060
ttttcgacct cattctatta gactctcgtt tggattgcaa ctggtctatt ttcctctttt    6120
gtttgataga aaatcataaa aggatttgca gactacgggc taaagaact aaaaaatcta     6180 tctgtttctt ttcattctct gtattttta tagtttctgt tgcatgggca taaagttgcc     6240
tttttaatca caattcagaa aatatcataa tatctcattt cactaaataa tagtgaacgg    6300
caggtatatg tgatgggtta aaaaggatcg gcggccgctc gatttaaatc              6350
```

<210> SEQ ID NO 8
<211> LENGTH: 6440
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 8

```
tcgagaggcc tgacgtcggg cccgacgtcg catgctcccg gccgccatgg ccgcgggata      60
tcactagtgc ggccgcctgc aggtcgacca tatgggagag ccactagtag gagcacaaac    120
acatgtccct aacgaacatc ccagcctcat ctcaatgggc aattagcgac gttttgaagc    180
gtccttcacc cggccgagta ccttttttctg tcgagtttat gccaccccgc gacgatgcag    240
ctgaagagcg tctttaccgc gcagcagagg tcttccatga cctcggtgca tcgtttgtct    300
ccgtgactta tggtgctggc ggatcaaccc gtgagagaac ctcacgtatt gctcgacgat    360
tagcgaaaca accgttgacc actctggtgc acctgaccct ggttctgcgg ccgcacagcg    420
atcccagagg aaatatcctc tggggtcgct gtgtcgacct taaagtttgg ctgccatgtg    480 aattttagc accctcaaca gttgagtgct ggcactctcg ggggtagagt gccaaatagg    540
ttgtttgaca cacagttgtt cacccgcgac gacggctgtg ctggaaaccc acaaccggca    600
cacacaaaat ttttctagag gagggattca tcatgaatac atacgaacaa attaataaag    660
tgaaaaaaat acttcggaaa catttaaaaa ataaccttat tggtacttac atgtttggat    720
caggagttga gagtggacta aaaccaaata gtgatcttga ctttttagtc gtcgtatctg    780
aaccattgac agatcaaagt aaagaaatac ttatacaaaa aattagacct atttcaaaaa    840
aaataggaga taaagcaac ttacgatata ttgaattaac aattattatt cagcaagaaa     900
tggtaccgtg gaatcatcct cccaaacaag aatttattta tggagaatgg ttacaagagc    960
tttatgaaca aggatacatt cctcagaagg aattaaattc agatttaacc ataatgcttt   1020
accaagcaaa acgaaaaaat aaaagaatat acgaaatta tgacttagag gaattactac    1080
ctgatattcc attttctgat gtgagaagag ccattatgga ttcgtcagag gaattaatag   1140
ataattatca ggatgatgaa accaactcta tattaacttt atgccgtatg attttaacta   1200
tggacacggg taaatcata ccaaaagata ttgcgggaaa tgcagtggct gaatcttctc    1260
cattagaaca tagggagaga attttgttag cagttcgtag ttatcttgga gagaatattg   1320
aatggactaa tgaaaatgta aatttaacta taaactattt aataacaga ttaaaaaaat    1380
```

```
tataaaaaaa ttgaaaaaat ggtggaaaca cttttttcaa tttttttgtt ttattattta    1440
atatttggga aatattcatt ctaattggta atcagatttt agaaaacaat aaacccttgc    1500 ataggggat  cgatatccgt ttaggctggg cggatccgcc ctcccgcacg ctttgcggga    1560
gggcggtacc agctcatcga tcttattaag tccactcctg agttccggga attcgacctc    1620
ggtatcgcct ccttccccga agggcatttc cgggcgaaaa ctctagaaga agacaccaaa    1680
tacactctgg cgaagctgcg tggagggca  gagtactcca tcacgcagat gttctttgat    1740
gtggaagact acctgcgact tcgtgatcgc cttgtcgctg cagacccat  tcatggtgcg    1800 aagccaatca ttcctggcat catgcccatt acgagcctgc ggtctgtgcg tcgacaggtc    1860
gaactctctg gtgctcaatt gccgagccaa ctagaagaat cacttgttcg agctgcaaac    1920
ggcaatgaag aagcgaacaa agacgagatc cgcaaggtgg gcattgaata ttccaccaat    1980
atggcagagc gactcattgc cgaaggtgcg gaagatctgc acttcatgac gcttaacttc    2040
acccgtgcaa cccaagaagt gttgtacaac cttggcatgg cgcctgcttg gggagcagag    2100
cacggccaag acgcggtgcg ttaagggatc cttaggaagg ctcccaacgc gtcatatgac    2160
tagttcggac ctaggatat  cgtcgacatc gatgctcttc tgcgttaatt aacaattggg    2220
atcctctaga cccgggattt aaatcgctag cgggctgcta aaggaagcgg aacacgtaga    2280
aagccagtcc gcagaaacgg tgctgacccc ggatgaatgt cagctactgg gctatctgga    2340
caagggaaaa cgcaagcgca aagagaaagc aggtagcttg cagtgggctt acatggcgat    2400
agctagactg ggcggtttta tggacagcaa gcgaaccgga attgccagct ggggcgccct    2460
ctggtaaggt tgggaagccc tgcaaagtaa actggatggc tttcttgccg ccaaggatct    2520
gatggcgcag gggatcaaga tctgatcaag agacaggatg aggatcgttt cgcatgattg    2580
aacaagatgg attgcacgca ggttctccgg ccgcttgggt ggagaggcta ttcggctatg    2640
actgggcaca acagacaatc ggctgctctg atgccgccgt gttccggctg tcagcgcagg    2700
ggcgcccggt tctttttgtc aagaccgacc tgtccggtgc cctgaatgaa ctgcaggacg    2760
aggcagcgcg gctatcgtgg ctggccacga cgggcgttcc ttgcgcagct gtgctcgacg    2820
ttgtcactga agcgggaagg gactggctgc tattgggcga agtgccgggg caggatctcc    2880
tgtcatctca ccttgctcct gccgagaaag tatccatcat ggctgatgca atgcggcggc    2940
tgcatacgct tgatccggct acctgcccat tcgaccacca agcgaaacat cgcatcgagc    3000
gagcacgtac tcggatggaa gccggtcttg tcgatcagga tgatctggac gaagagcatc    3060
aggggctcgc gccagccgaa ctgttcgcca ggctcaaggc gcgcatgccc gacggcgagg    3120
atctcgtcgt gacccatggc gatgcctgct tgccgaatat catggtggaa aatggccgct    3180
tttctggatt catcgactgt ggccggctgg gtgtggcgga ccgctatcag gacatagcgt    3240
tggctacccg tgatattgct gaagagcttg gcggcgaatg ggctgaccgc ttcctcgtgc    3300
tttacggtat cgccgctccc gattcgcagc gcatcgcctt ctatcgcctt cttgacgagt    3360
tcttctgagc gggactctgg ggttcgaaat gaccgaccaa gcgacgccca acctgccatc    3420
acgagatttc gattccaccg ccgccttcta tgaaaggttg gcttcggaa  tcgttttccg    3480 ggacgccggc tggatgatcc tccagcgcgg ggatctcatg ctggagttct cgcccacgc    3540 tagcggcgcg ccgccggcc  cggtgtgaaa taccgcacag atgcgtaagg agaaaatacc    3600
gcatcaggcg ctcttccgct tcctcgctca ctgactcgct gcgctcggtc gttcggctgc    3660
ggcgagcggt atcagctcac tcaaaggcgg taatacggtt atccacagaa tcaggggata    3720
acgcaggaaa gaacatgtga gcaaaaggcc agcaaaaggc caggaaccgt aaaaaggccg    3780
```

```
cgttgctggc gttttttccat aggctccgcc ccctgacga gcatcacaaa aatcgacgct    3840
caagtcagag gtggcgaaac ccgacaggac tataaagata ccaggcgttt cccctggaa      3900 gctccctcgt gcgctctcct gttccgaccc tgccgcttac cggataccctg tccgcctttc    3960 tcccttcggg aagcgtggcg ctttctcata gctcacgctg taggtatctc agttcggtgt    4020
aggtcgttcg ctccaagctg gctgtgtgc acgaaccccc cgttcagccc gaccgctgcg      4080
ccttatccgg taactatcgt cttgagtcca acccggtaag acacgactta tcgccactgg    4140
cagcagccac tggtaacagg attagcagag cgaggtatgt aggcggtgct acagagttct    4200
tgaagtggtg gcctaactac ggctacacta aaggacagt atttggtatc tgcgctctgc     4260
tgaagccagt taccttcgga aaagagttg gtagctcttg atccggcaaa caaaccaccg     4320
ctggtagcgg tggttttttt gtttgcaagc agcagattac gcgcagaaaa aaaggatctc    4380
aagaagatcc tttgatcttt tctacggggt ctgacgctca gtggaacgaa aactcacgtt    4440
aagggatttt ggtcatgaga ttatcaaaaa ggatcttcac ctagatcctt ttaaaggccg    4500
gccgcggccg ccatcggcat tttcttttgc gttttttattt gttaactgtt aattgtccctt   4560 gttcaaggat gctgtctttg acaacagatg ttttcttgcc tttgatgttc agcaggaagc    4620
tcggcgcaaa cgttgattgt ttgtctgcgt agaatcctct gtttgtcata tagcttgtaa    4680
tcacgacatt gtttccttttc gcttgaggta cagcgaagtg tgagtaagta aaggttacat    4740
cgttaggatc aagatccatt tttaacacaa ggccagtttt gttcagcggc ttgtatgggc    4800
cagttaaaga attagaaaca taaccaagca tgtaaatatc gttagacgta atgccgtcaa    4860
tcgtcatttt tgatccgcgg gagtcagtga acaggtacca tttgccgttc atttttaaaga  4920 cgttcgcgcg ttcaatttca tctgttactg tgttagatgc aatcagcggt ttcatcactt    4980
ttttcagtgt gtaatcatcg tttagctcaa tcataccgag agcgccgttt gctaactcag    5040
ccgtgcgttt tttatcgctt tgcagaaagtt tttgactttc ttgacggaag aatgatgtgc   5100
ttttgccata gtatgctttg ttaaataaag attcttcgcc ttggtagcca tcttcagttc    5160
cagtgtttgc ttcaaatact aagtatttgt ggcctttatc ttctacgtag tgaggatctc    5220
tcagcgtatg gttgtcgcct gagctgtagt tgccttcatc gatgaactgc tgtacatttt   5280
gatacgtttt tccgtcaccg tcaaagattg atttataatc ctctacaccg ttgatgttca   5340
aagagctgtc tgatgctgat acgttaactt gtgcagttgt cagtgtttgt ttgccgtaat    5400
gtttaccgga gaaatcagtg tagaataaac ggatttttcc gtcagatgta aatgtggctg    5460
aacctgacca ttcttgtgtt tggtctttta ggatagaatc atttgcatcg aatttgtcgc    5520
tgtctttaaa gacgcggcca gcgttttttcc agctgtcaat agaagtttcg ccgactttt    5580 gatagaacat gtaaatcgat gtgtcatccg catttttagg atctccggct aatgcaaaga    5640
cgatgtggta gccgtgatag tttgcgacag tgccgtcagc gttttgtaat ggccagctgt    5700
cccaaacgtc caggcctttt gcagaagaga tattttttaat tgtggacgaa tcaaattcag   5760
aaacttgata tttttcattt ttttgctgtt cagggatttg cagcatatca tggcgtgtaa    5820
tatgggaaat gccgtatgtt tccttatatg gcttttggtt cgtttctttc gcaaacgctt    5880
gagttgcgcc tcctgccagc agtgcggtag taaaggttaa tactgttgct tgttttgcaa    5940 acttttgat gttcatcgtt catgtctcct ttttatgta ctgtgttagc ggtctgcttc      6000
ttccagccct cctgtttgaa gatggcaagt tagttacgca caataaaaaa agacctaaaa    6060
tatgtaaggg gtgacgccaa agtatacact ttgcccttta cacattttag gtcttgcctg    6120
ctttatcagt aacaaacccg cgcgatttac ttttcgacct cattctatta gactctcgtt    6180
```

| | |
|---|---|
| tggattgcaa ctggtctatt ttcctctttt gtttgataga aaatcataaa aggatttgca | 6240 |
| gactacgggc ctaaagaact aaaaaatcta tctgtttctt ttcattctct gtattttta | 6300 |
| tagtttctgt tgcatgggca taaagttgcc ttttaatca caattcagaa aatatcataa | 6360 |
| tatctcattt cactaaataa tagtgaacgg caggtatatg tgatgggtta aaaaggatcg | 6420 |
| gcggccgctc gatttaaatc | 6440 |

<210> SEQ ID NO 9
<211> LENGTH: 5106
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 9

| | |
|---|---|
| tcgaggtcga cggtatcgat ggtttgatgt tggttccgat gggcatcatc tctgtggtga | 60 |
| tgtcaccagt aattggacga ttggtggatc gcctggcacc aggaatgatc tccaagatcg | 120 |
| gattcggcgc gctgattttc tcgatggcgt tgatggctgt ctttatgatc gccaacctat | 180 |
| cgccgtggtg gctactcatc ccgattattt tgttcggtag ctccaacgcg atgagttttg | 240 |
| caccgaactc tgtgattgct ctgcgtgatg ttccgcagga tttagtgggc tctgcttctg | 300 |
| gtttttacaa cacctcacgc caggtgggcg ctgttttggg cgccgctacc ttgggcgctg | 360 |
| tgatgcaaat aggagtgggc acggtgtcct tcggtgttgc catgggtgcg gcaatcctgg | 420 |
| tgacactcgt gcccttaatc tttgggttcc tagcggtaac ccaatgctag ctcttctgac | 480 |
| gatgtttcaa ggttcgcgaa atcaccgggt ggcagaaagc tgccccgggg gtttcctcgc | 540 |
| ctttttgtaa tcgaggtcgt cccacttaac gcttaaaatt tccattcaga aagctttggc | 600 |
| gttcctcatc atccggggct ccagggagag gattaaaagt gaaccgattg cgttttcaac | 660 |
| caaaccctag actgctcggt ctgtcaagaa gttccgggga tttaaattca tggtgccgtt | 720 |
| ttgggctcct gttgtctgcg tcgggtgggg aagtggcgta aaggtgtgca acctcatagt | 780 |
| caagttgacg gaaaagggga gatcgcattt taccccccgca gattttgggg aacctgtttt | 840 |
| gaactggggt tttgcaaaat gcaacgcggt gacgtgtggt tacaactagt tctagacccg | 900 |
| ggatttaaat cgctagcggg ctgctaaagg aagcggaaca cgtagaaagc cagtccgcag | 960 |
| aaacggtgct gaccccggat gaatgtcagc tactgggcta tctggacaag ggaaaacgca | 1020 |
| agcgcaaaga gaaagcaggt agcttgcagt gggcttacat ggcgatagct agactgggcg | 1080 |
| gttttatgga cagcaagcga accggaattg ccagctgggg cgccctctgg taaggttggg | 1140 |
| aagccctgca aagtaaactg gatggctttc ttgccgccaa ggatctgatg cgcaggggga | 1200 |
| tcaagatctg atcaagagac aggatgagga tcgtttcgca tgattgaaca agatggattg | 1260 |
| cacgcaggtt ctccggccgc ttgggtggag aggctattcg gctatgactg ggcacaacag | 1320 |
| acaatcggct gctctgatgc cgccgtgttc cggctgtcag cgcaggggcg cccggttctt | 1380 |
| tttgtcaaga ccgacctgtc cggtgccctg aatgaactgc aggacgaggc agcgcggcta | 1440 |
| tcgtggctgg ccacgacggg cgttccttgc gcagctgtgc tcgacgttgt cactgaagcg | 1500 |
| ggaagggact ggctgctatt gggcgaagtg ccggggcagg atctcctgtc atctcacctt | 1560 |
| gctcctgccg agaaagtatc catcatggct gatgcaatgc ggcggctgca tacgcttgat | 1620 |
| ccggctacct gcccattcga ccaccaagcg aaacatcgca tcgagcgagc acgtactcgg | 1680 |
| atggaagccg gtcttgtcga tcaggatgat ctggacgaag agcatcaggg gctcgcgcca | 1740 |

-continued

```
gccgaactgt tcgccaggct caaggcgcgc atgcccgacg gcgaggatct cgtcgtgacc      1800
catggcgatg cctgcttgcc gaatatcatg gtggaaaatg gccgcttttc tggattcatc      1860
gactgtggcc ggctgggtgt ggcggaccgc tatcaggaca tagcgttggc tacccgtgat      1920
attgctgaag agcttggcgg cgaatgggct gaccgcttcc tcgtgcttta cggtatcgcc      1980
gctcccgatt cgcagcgcat cgccttctat cgccttcttg acgagttctt ctgagcggga      2040
ctctggggtt cgaaatgacc gaccaagcga cgcccaacct gccatcacga gatttcgatt      2100
ccaccgccgc cttctatgaa aggttgggct tcggaatcgt tttccgggac gccggctgga      2160
tgatcctcca gcgcgggat ctcatgctgg agttcttcgc ccacgctagc ggcgcgccgg       2220
ccggcccggt gtgaaatacc gcacagatgc gtaaggagaa ataccgcat caggcgctct       2280 tccgcttcct cgctcactga ctcgctgcgc tcggtcgttc ggctgcggcg agcggtatca      2340
gctcactcaa aggcggtaat acggttatcc acagaatcag gggataacgc aggaaagaac      2400
atgtgagcaa aaggccagca aaaggccagg aaccgtaaaa aggccgcgtt gctggcgttt      2460
ttccataggc tccgccccc tgacgagcat cacaaaaatc gacgctcaag tcagaggtgg       2520
cgaaacccga caggactata aagataccag gcgtttcccc ctggaagctc cctcgtgcgc      2580
tctcctgttc cgaccctgcc gcttaccgga tacctgtccg cctttctccc ttcgggaagc     2640
gtggcgcttt ctcatagctc acgctgtagg tatctcagtt cggtgtaggt cgttcgctcc      2700
aagctgggct gtgtgcacga accccccgtt cagcccgacc gctgcgcctt atccggtaac     2760
tatcgtcttg agtccaaccc ggtaagacac gacttatcgc cactggcagc agccactggt     2820
aacaggatta gcagagcgag gtatgtaggc ggtgctacag agttcttgaa gtggtggcct     2880
aactacggct acactagaag gacagtattt ggtatctgcg ctctgctgaa gccagttacc     2940
ttcggaaaaa gagttggtag ctcttgatcc ggcaaacaaa ccaccgctgg tagcggtggt     3000 tttttgttt gcaagcagca gattacgcgc agaaaaaaag gatctcaaga agatcctttg     3060 atctttcta cggggtctga cgctcagtgg aacgaaaact cacgttaagg attttggtc      3120 atgagattat caaaaaggat cttcacctag atccttttaa aggccggccg cggccgccat      3180
cggcattttc ttttgcgttt ttatttgtta actgttaatt gtccttgttc aaggatgctg      3240 tcttttgacaa cagatgtttt cttgcctttg atgttcagca ggaagctcgg cgcaaacgtt      3300
gattgtttgt ctgcgtagaa tcctctgttt gtcatatagc ttgtaatcac gacattgttt      3360
cctttcgctt gaggtacagc gaagtgtgag taagtaaagg ttacatcgtt aggatcaaga      3420 tccatttta acacaaggcc agtttgttc agcggcttgt atgggccagt taagaatta      3480 gaaacataac caagcatgta aatatcgtta gacgtaatgc cgtcaatcgt cattttgat      3540 ccgcgggagt cagtgaacag gtaccatttg ccgttcattt taaagacgtt cgcgcgttca     3600
atttcatctg ttactgtgtt agatgcaatc agcggtttca tcactttttt cagtgtgtaa     3660
tcatcgttta gctcaatcat accgagagcg ccgtttgcta actcagccgt gcgttttta    3720 tcgctttgca gaagttttg actttcttga cggaagaatg atgtgctttt gccatagtat     3780
gctttgttaa ataaagattc ttcgccttgg tagccatctt cagttccagt gtttgcttca     3840
aatactaagt atttgtggcc tttatcttct acgtagtgag gatctctcag cgtatggttg     3900
tcgcctgagc tgtagttgcc ttcatcgatg aactgctgta catttgata cgttttccg      3960 tcaccgtcaa agattgattt ataatcctct acaccgttga tgttcaaaga gctgtctgat     4020
gctgatacgt taacttgtgc agttgtcagt gtttgtttgc cgtaatgttt accggagaaa     4080
tcagtgtaga ataaacggat ttttccgtca gatgtaaatg tggctgaacc tgaccattct     4140
```

| | |
|---|---|
| tgtgtttggt cttttaggat agaatcattt gcatcgaatt tgtcgctgtc tttaaagacg | 4200 |
| cggccagcgt ttttccagct gtcaatagaa gtttcgccga cttttttgata gaacatgtaa | 4260 |
| atcgatgtgt catccgcatt tttaggatct ccggctaatg caaagacgat gtggtagccg | 4320 |
| tgatagtttg cgacagtgcc gtcagcgttt tgtaatggcc agctgtccca aacgtccagg | 4380 |
| cctttttgcag aagagatatt tttaattgtg gacgaatcaa attcagaaac ttgatatttt | 4440 |
| tcatttttt gctgttcagg gatttgcagc atatcatggc gtgtaatatg ggaaatgccg | 4500 |
| tatgttttcct tatatggctt ttggttcgtt tctttcgcaa acgcttgagt tgcgcctcct | 4560 |
| gccagcagtg cggtagtaaa ggttaatact gttgcttgtt ttgcaaactt tttgatgttc | 4620 |
| atcgttcatg tctcctttt tatgtactgt gttagcggtc tgcttcttcc agccctcctg | 4680 |
| tttgaagatg gcaagttagt tacgcacaat aaaaaaagac ctaaaatatg taaggggtga | 4740 |
| cgccaaagta tacactttgc cctttacaca ttttaggtct tgcctgcttt atcagtaaca | 4800 |
| aacccgcgcg atttactttt cgacctcatt ctattagact ctcgtttgga ttgcaactgg | 4860 |
| tctatttcc tcttttgttt gatagaaaat cataaaagga tttgcagact acgggcctaa | 4920 |
| agaactaaaa aatctatctg tttctttcca ttctctgtat tttttatagt ttctgttgca | 4980 |
| tgggcataaa gttgccttttt taatcacaat tcagaaaata tcataatatc tcatttcact | 5040 |
| aaataatagt gaacggcagg tatatgtgat gggttaaaaa ggatcggcgg ccgctcgatt | 5100 |
| taaatc | 5106 |

<210> SEQ ID NO 10
<211> LENGTH: 5512
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 10

| | |
|---|---|
| tcgagaggcc tgacgtcggg cccggtacca cgcgtcatat gactagttcg gacctaggga | 60 |
| tatcgtcgac atcgatgctc ttctgcgtta attaacaatt gggatctctc aactaatgca | 120 |
| gcgatgcgtt ctttccagaa tgctttcatg acagggatgc tgtcttgatc aggcaggcgt | 180 |
| ctgtgctgga tgccgaagct ggattattg tcgccttttgg aggtgaagtt gacgctcact | 240 |
| cgagaatcat cggccaacca tttggcattg aatgttctag gttcggaggc ggaggttttc | 300 |
| tcaattagtg cgggatcgag ccactgcgcc gcaggtcat cgtctccgaa gagcttccac | 360 |
| acttttcga ccggcaggtt aagggttttg gaggcattgg ccgcgaaccc atcgctggtc | 420 |
| atcccgggtt tgcgcatgcc acgttcgtat tcataaccaa tcgcgatgcc ttgagcccac | 480 |
| cagccactga catcaaagtt gtccacgatg tgctttgcga tgtgggtgtg agtccaagag | 540 |
| gtggcttta cgtcgtcaag caattttagc cactcttccc acggctttcc ggtgccgttg | 600 |
| aggatagctt caggggacat gcctggtgtt gagccttgcg gagtggagtc agtcatgcga | 660 |
| ccgagactag tggcgctttg gtaccttggt tgtatggcta cttcccagcg gtcgcggaag | 720 |
| gcgatgacgt ggtgatcttg gaatccccgg atccacacgc agccgaacgc atgcgcttta | 780 |
| gcttcccacg ccagcagcgc ggcaggttct tgtgcatcgc ggatttcatt cgcccacgcg | 840 |
| agcaagctgt caaggacggc caagtggacg tcatgccatt ccagctggtc accatgggta | 900 |
| atcctattgc tgatttcgcc aacgagttgt tcgcagccaa tgaataccgc gagtacttgg | 960 |
| aagttcacgg catcggcgtg cagctcaccg aagcattggc cgagtactgg cactcccgag | 1020 |
| tgcgcagcga actcaagctg aacgacggtg gatctgtcgc tgattttgat ccagaagaca | 1080 |

```
agaccaagtt cttcgacctg gattaccgcg gcgcccgctt ctcctttggt tacggttctt    1140
gccctgatct ggaagaccgc gcaaagctgg tggaattgct cgagccaggc cgtatcggcg    1200
tggagttgtc cgaggaactc cagctgcacc cagagcagtc cacagacgcg tttgtgctct    1260
accacccaga ggcaaagtac tttaacgtct aatctagacc cgggatttaa atgatccgct    1320
agcgggctgc taaaggaagc ggaacacgta gaaagccagt ccgcagaaac ggtgctgacc    1380
ccggatgaat gtcagctact gggctatctg gacaagggaa aacgcaagcg caaagagaaa    1440
gcaggtagct tgcagtgggc ttacatggcg atagctagac tgggcggttt tatgacagc     1500 aagcgaaccg gaattgccag ctggggcgcc ctctggtaag gttgggaagc cctgcaaagt    1560
aaactgatgg gctttcttgc cgccaaggat ctgatggcgc aggggatcaa gatctgatca    1620
agagacagga tgaggatcgt ttcgcatgat tgaacaagat ggattgcacg caggttctcc    1680
ggccgcttgg gtggagaggc tattcggcta tgactgggca caacagacaa tcggctgctc    1740
tgatgccgcc gtgttccggc tgtcagcgca ggggcgcccg gttcttttg tcaagaccga    1800 cctgtccggt gccctgaatg aactgcagga cgaggcagcg cggctatcgt ggctggccac    1860
gacgggcgtt ccttgcgcag ctgtgctcga cgttgtcact gaagcgggaa gggactggct    1920
gctattgggc gaagtgccgg ggcaggatct cctgtcatct caccttgctc ctgccgagaa    1980
agtatccatc atggctgatg caatgcgcg gctgcatacg cttgatccgg ctacctgccc    2040
attcgaccac caagcgaaac atcgcatcga gcgagcacgt actcggatgg aagccggtct    2100
tgtcgatcag gatgatctgg acgaagagca tcagggctc cgccagccg aactgttcgc     2160 caggctcaag gcgcgcatgc ccgacggcga ggatctcgtc gtgacccatg gcgatgcctg    2220
cttgccgaat atcatggtgg aaaatggccg cttttctgga ttcatcgact gtggccggct    2280
gggtgtggcg gaccgctatc aggacatagc gttggctacc cgtgatattg ctgaagagct    2340
tggcggcgaa tgggctgacc gcttcctcgt gctttacggt atcgccgctc ccgattcgca    2400
gcgcatcgcc ttctatcgcc ttcttgacga gttcttctga gcgggactct ggggttcgaa    2460
atgaccgacc aagcgacgcc caacctgcca tcacgagatt tcgattccac cgccgccttc    2520
tatgaaaggt tgggcttcgg aatcgttttc cgggacgccg gctggatgat cctccagcgc    2580
ggggatctca tgctggagtt cttcgcccac gctagcggcg cgccggccgg cccggtgtga   2640
aataccgcac agatgcgtaa ggagaaaata ccgcatcagg cgctcttccg cttcctcgct    2700
cactgactcg ctgcgctcgg tcgttcggct gcggcgagcg gtatcagctc actcaaaggc    2760
ggtaatacgg ttatccacag aatcagggga taacgcagga agaacatgt gagcaaaagg     2820 ccagcaaaag gccaggaacc gtaaaaaggc cgcgttgctg gcgttttcc ataggctccg     2880 cccccctgac gagcatcaca aaaatcgacg ctcaagtcag aggtggcgaa acccgacagg    2940
actataaaga taccaggcgt ttccccctgg aagctccctc gtgcgctctc ctgttccgac    3000
cctgccgctt accggatacc tgtccgcctt tctcccttcg ggaagcgtgg cgctttctca    3060
tagctcacgc tgtaggtatc tcagttcggt gtaggtcgtt cgctccaagc tgggctgtgt    3120
gcacgaaccc cccgttcagc ccgaccgctg cgccttatcc ggtaactatc gtcttgagtc    3180
caacccggta agacacgact tatcgccact ggcagcagcc actggtaaca ggattagcag    3240
agcgaggtat gtaggcggtg ctacagagtt cttgaagtgg tggcctaact acggctacac    3300
tagaaggaca gtatttggta tctgcgctct gctgaagcca gttaccttcg gaaaaagagt    3360
tggtagctct tgatccggca aacaaaccac cgctggtagc ggtggttttt ttgtttgcaa    3420
gcagcagatt acgcgcagaa aaaaaggatc tcaagaagat cctttgatct tttctacggg    3480
```

```
gtctgacgct cagtggaacg aaaactcacg ttaagggatt ttggtcatga gattatcaaa    3540
aaggatcttc acctagatcc tttaaaggc cggccgcggc cgccatcggc attttctttt    3600
gcgtttttat ttgttaactg ttaattgtcc ttgttcaagg atgctgtctt tgacaacaga    3660
tgttttcttg cctttgatgt tcagcaggaa gctcggcgca aacgttgatt gtttgtctgc    3720
gtagaatcct ctgtttgtca tatagcttgt aatcacgaca ttgtttcctt tcgcttgagg    3780
tacagcgaag tgtgagtaag taaaggttac atcgttagga tcaagatcca tttttaacac    3840
aaggccagtt ttgttcagcg gcttgtatgg gccagttaaa gaattagaaa cataaccaag    3900
catgtaaata tcgttagacg taatgccgtc aatcgtcatt tttgatccgc gggagtcagt    3960
gaacaggtac catttgccgt tcattttaaa gacgttcgcg cgttcaattt catctgttac    4020
tgtgttagat gcaatcagcg gtttcatcac ttttttcagt gtgtaatcat cgtttagctc    4080
aatcataccg agagcgccgt ttgctaactc agccgtgcgt tttttatcgc tttgcagaag    4140
tttttgactt tcttgacgga agaatgatgt gcttttgcca tagtatgctt tgttaaataa    4200
agattcttcg ccttggtagc catcttcagt tccagtgttt gcttcaaata ctaagtattt    4260
gtggccttta tcttctacgt agtgaggatc tctcagcgta tggttgtcgc ctgagctgta    4320
gttgccttca tcgatgaact gctgtacatt ttgatacgtt tttccgtcac cgtcaaagat    4380
tgatttataa tcctctacac cgttgatgtt caaagagctg tctgatgctg atacgttaac    4440
ttgtgcagtt gtcagtgttt gtttgccgta atgtttaccg gagaaatcag tgtagaataa    4500
acggattttt ccgtcagatg taaatgtggc tgaacctgac cattcttgtg tttggtcttt    4560
taggatagaa tcatttgcat cgaatttgtc gctgtcttta aagacgcggc cagcgttttt    4620
ccagctgtca atagaagttt cgccgacttt ttgatagaac atgtaaatcg atgtgtcatc    4680 cgcatttta ggatctccgg ctaatgcaaa gacgatgtgg tagccgtgat agtttgcgac    4740
agtgccgtca gcgttttgta atggccagct gtcccaaacg tccaggcctt ttgcagaaga    4800
gatattttta attgtggacg aatcaaattc agaaacttga tattttcat ttttttgctg    4860 ttcagggatt tgcagcatat catggcgtgt aatatgggaa atgccgtatg tttccttata    4920
tggcttttgg ttcgtttctt tcgcaaacgc ttgagttgcg cctcctgcca gcagtgcggt    4980
agtaaaggtt aatactgttg cttgttttgc aaacttttg atgttcatcg ttcatgtctc    5040
cttttttatg tactgtgtta gcggtctgct tcttccagcc ctcctgtttg aagatggcaa    5100
gttagttacg cacaataaaa aaagacctaa aatatgtaag gggtgacgcc aaagtataca    5160
ctttgccctt tacacatttt aggtcttgcc tgctttatca gtaacaaacc cgcgcgattt    5220
acttttcgac ctcattctat tagactctcg tttggattgc aactggtcta ttttcctctt    5280
ttgtttgata gaaaatcata aaaggatttg cagactacgg gcctaaagaa ctaaaaaatc    5340
tatctgtttc ttttcattct ctgtattttt tatagtttct gttgcatggg cataaagttg    5400 ccttttaat cacaattcag aaaatatcat aatatctcat ttcactaaat aatagtgaac    5460
ggcaggtata tgtgatgggt taaaaggat cggcggccgc tcgatttaaa tc              5512
```

<210> SEQ ID NO 11
<211> LENGTH: 914
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 11

-continued

```
atgccaaagt acgacaattc caatgctgac cagtggggct ttgaaacccg ctccattcac    60
gcaggccagt cagtagacgc acagaccagc gcacgaaacc ttccgatcta ccaatccacc   120
gctttcgtgt tcgactccgc tgagcacgcc aagcagcgtt tcgcacttga ggatctaggc   180
cctgtttact cccgcctcac caacccaacc gttgaggctt ggaaaaccg catcgcttcc    240 ctcgaaggtg gcgtccacgc tgtagcgttc tcctccggac aggccgcaac caccaacgcc   300
attttgaacc tggcaggagc gggcgaccac atcgtcacct ccccacgcct ctacggtggc   360
accgagactc tattccttat cactcttaac cgcctgggta tcgatgtttc cttcgtggaa   420
aaccccgacg accctgagtc ctggcaggca gccgttcagc caaacaccaa agcattcttc   480
ggcgagactt tcgccaaccc acaggcagac gtcctggata ttcctgcggt ggctgaagtt   540
gcgcaccgca acagcgttcc actgatcatc gacaacacca tcgctaccgc agcgctcgtg   600
cgcccgctct ccctcgttgt tcacccagca accaccaccc attcacagtc cgacgaagct   660
ggcctggcac gcgcgggcgt tacccagtcc accgtccgcc tgtccgttgg catcgagacc   720
attgatgata tcatcgctga cctcgaaggc ggctttgctg caatctagct ttaaatagac   780 tcacccccagt gcttaaagcg ctgggttttt ctttttcaga ctcgtgagaa tgcaaactag   840
actagacaga gctgtccata tacactggac gaagttttag tcttgtccac ccagaacagg   900
cggttatttt catg                                                     914

<210> SEQ ID NO 12
<211> LENGTH: 184
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 12
ggtcgagcgg cttaaagttt ggctgccatg tgaattttta gcaccctcaa cagttgagtg    60
ctggcactct cggggtaga gtgccaaata ggttgtttga cacacagttg ttcacccgcg   120
acgacggctg tgctggaaac ccacaaccgg cacacacaaa attttctca tggagggatt   180 catc                                                                184

<210> SEQ ID NO 13
<211> LENGTH: 8554
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 13
tcgagaggcc tgacgtcggg cccggtaccg ttgctcgctg atctttcggc ttaacaactt    60
tgtattcaat cagtcgggca tagaaagaaa acgcaatgat ataggaacca actgccgcca   120
aaaccagcca cacagagttg attgtttcgc cacgggagaa agcgattgct ccccaaccca   180
ccgccgcgat aaccccaaag acaaggagac caacgcgggc ggtcggtgac attttagggg   240
acttcttcac gcctactgga aggtcagtag cgttgctgta caccaaatca tcgtcattga   300
tgttgtcagt ctgttttatg gtcacgatct ttactgtttt ctcttcgggt cgtttcaaag   360
ccactatgcg tagaaacagc gggcagaaac tgtgtgcaga aatgcatgca gaaaaggaa    420 agttcggcca gatgggtgtt tctgtatgcc gatgatcgga tctttgacag ctgggtatgc   480
gacaaatcac cgagagttgt taattcttaa caatggaaaa gtaacattga gagatgattt   540
```

```
ataccatcct gcaccattta gagtggggct agtcataccc ccataaccct agctgtacgc    600
aatcgatttc aaatcagttg gaaaaagtca agaaaattac ccgagacata tgcggcttaa    660
agtttggctg ccatgtgaat ttttagcacc ctcaacagtt gagtgctggc actctcgagg    720
gtagagtgcc aaataggttg tttgacacac agttgttcac ccgcgacgac ggctgtgctg    780
gaaacccaca accggcacac acaaaatttt tctcatggag ggattcatca tgccaaagta    840
cgacaattcc aatgctgacc agtggggctt tgaaacccgc tccattcacg caggccagtc    900
agtagacgca cagaccagcg cacgaaacct tccgatctac caatccaccg ctttcgtgtt    960
cgactccgct gagcacgcca agcagcgttt cgcacttgag gatctaggcc ctgtttactc   1020
ccgcctcacc aacccaaccg ttgaggcttt ggaaaaccgc atcgcttccc tcgaaggtgg   1080
cgtccacgct gtagcgttct cctccggaca ggccgcaacc accaacgcca ttttgaacct   1140
ggcaggagcg ggcgaccaca tcgtcacctc cccacgcctc tacggtggca ccgagactct   1200
attccttatc actcttaacc gcctgggtat cgatgtttcc ttcgtggaaa accccgacga   1260
ccctgagtcc tggcaggcag ccgttcagcc aaacaccaaa gcattcttcg gcgagacttt   1320
cgccaaccca caggcagacg tcctggatat tcctgcggtg gctgaagttg cgcaccgcaa   1380
cagcgttcca ctgatcatcg acaacaccat cgctaccgca gcgctcgtgc gcccgctcga   1440
gctcggcgca gacgttgtcg tcgcttccct caccaagttc tacaccggca acggctccgg   1500
actgggcggc gtgcttatcg acggcggaaa gttcgattgg actgtcgaaa aggatggaaa   1560
gccagtattc ccctacttcg tcactccaga tgctgcttac cacggattga agtacgcaga   1620
ccttggtgca ccagccttcg gcctcaaggt tcgcgttggc cttctacgcg acaccggctc   1680
caccctctcc gcattcaacg catgggctgc agtccagggc atcgacaccc tttccctgcg   1740
cctggagcgc acaacgaaaa acgccatcaa ggttgcagaa ttcctcaaca accacgagaa   1800
ggtgaaaaag gttaacttcg caggcctgaa ggattcccct tggtacgcaa ccaaggaaaa   1860
gcttggcctg aagtacaccg gctccgttct caccttcgag atcaagggcg gcaaggatga   1920
ggcttgggca tttatcgacg ccctgaagct acactccaac cttgcaaaca tcggcgatgt   1980
tcgctccctc gttgttcacc cagcaaccac cacccattca cagtccgacg aagctggcct   2040
ggcacgcgcg ggcgttaccc agtccaccgt ccgcctgtcc gttggcatcg agaccattga   2100
tgatatcatc gctgacctcg aaggcggctt tgctgcaatc tagcactagt tcggacctag   2160
ggatatcgtc gagagctgcc aattattccg ggcttgtgac ccgctacccg ataaataggt   2220
cggctgaaaa atttcgttgc aatatcaaca aaaaggccta tcattgggag gtgtcgcacc   2280
aagtactttt gcgaagcgcc atctgacgga ttttcaaaag atgtatatgc tcggtgcgga   2340
aacctacgaa aggatttttt acccatgccc accctcgcgc cttcaggtca acttgaaatc   2400
caagcgatcg gtgatgtctc caccgaagcc ggagcaatca ttacaaacgc tgaaatcgcc   2460
tatcaccgct ggggtgaata ccgcgtagat aaagaaggac gcagcaatgt cgttctcatc   2520
gaacacgccc tcactggaga ttccaacgca gccgattggt gggctgactt gctcggtccc   2580
ggcaaagcca tcaacactga tatttactgc gtgatctgta ccaacgtcat cggtggttgc   2640
aacggttcca ccggacctgg ctccatgcat ccagatggaa atttctgggg taatcgcttc   2700
cccgccacgt ccattcgtga tcaggtaaac gccgaaaaac aattcctcga cgcactcggc   2760
atcaccacgg tcgccgcagt acttggtggt tccatgggtg gtgcccgcac cctagagtgg   2820
gccgcaatgt acccagaaac tgttggcgca gctgctgttc ttgcagtttc tgcacgcgcc   2880
agcgcctggc aaatcggcat tcaatccgcc caaattaagg cgattgaaaa cgaccaccac   2940
```

```
tggcacgaag gcaactacta cgaatccggc tgcaacccag ccaccggact cggcgccgcc    3000
cgacgcatcg cccacctcac ctaccgtggc gaactagaaa tcgacgaacg cttcggcacc    3060
aaagcccaaa agaacgaaaa cccactcggt ccctaccgca agcccgacca gcgcttcgcc    3120
gtggaatcct acttggacta ccaagcagac aagctagtac agcgtttcga cgccggctcc    3180
tacgtcttgc tcaccgacgc cctcaaccgc cacgacattg gtcgcgaccg cggaggcctc    3240
aacaaggcac tcgaatccat caaagttcca gtccttgtcg caggcgtaga taccgatatt    3300
ttgtacccct accaccagca agaacacctc tccagaaacc tgggaaatct actggcaatg    3360
gcaaaaatcg tatccctgt cggccacgat gctttcctca ccgaaagccg ccaaatggat     3420
cgcatcgtga ggaacttctt cagcctcatc tccccagacg aagacaaccc ttcgacctac    3480
atcgagttct acatctaaca tatgactagt tcggacctag ggatatcgtc gacatcgatg    3540
ctcttctgcg ttaattaaca attgggatcc tctagacccg ggatttaaat cgctagcggg    3600
ctgctaaagg aagcggaaca cgtagaaagc cagtccgcag aaacggtgct gaccccggat    3660
gaatgtcagc tactgggcta tctggacaag ggaaaacgca agcgcaaaga gaaagcaggt    3720
agcttgcagt gggcttacat ggcgatagct agactgggcg gttttatgga cagcaagcga    3780
accggaattg ccagctgggg cgccctctgg taaggttggg aagccctgca agtaaactg     3840
gatggctttc ttgccgccaa ggatctgatg gcgcagggga tcaagatctg atcaagagac    3900
aggatgagga tcgtttcgca tgattgaaca agatggattg cacgcaggtt ctccggccgc    3960
ttgggtggag aggctattcg gctatgactg ggcacaacag acaatcggct gctctgatgc    4020
cgccgtgttc cggctgtcag cgcaggggcg cccggttctt tttgtcaaga ccgacctgtc    4080
cggtgccctg aatgaactgc aggacgagge agcgcggcta tcgtggctgg ccacgacggg    4140
cgttccttgc gcagctgtgc tcgacgttgt cactgaagcg ggaagggact ggctgctatt    4200
gggcgaagtg ccggggcagg atctcctgtc atctcacctt gctcctgccg agaaagtatc    4260
catcatggct gatgcaatgc ggcggctgca tacgcttgat ccggctacct gcccattcga    4320
ccaccaagcg aaacatcgca tcgagcgagc acgtactcgg atggaagccg gtcttgtcga    4380
tcaggatgat ctggacgaag agcatcaggg gctcgcgcca gccgaactgt tcgccaggct    4440
caaggcgcgc atgcccgacg gcgaggatct cgtcgtgacc catggcgatg cctgcttgcc    4500
gaatatcatg gtgaaaatg gccgcttttc tggattcatc gactgtggcc ggctgggtgt      4560
ggcggaccgc tatcaggaca tagcgttggc tacccgtgat attgctgaag agcttggcgg    4620
cgaatgggct gaccgcttcc tcgtgcttta cggtatcgcc gctcccgatt cgcagcgcat    4680
cgccttctat cgccttcttg acgagttctt ctgagcggga ctctggggtt cgaaatgacc    4740
gaccaagcga cgcccaacct gccatcacga gatttcgatt ccaccgccgc cttctatgaa    4800
aggttgggct tcggaatcgt tttccgggac gccggctgga tgatcctcca gcgcgggat    4860
ctcatgctgg agttcttcgc ccacgctagc ggcgcgccgg ccggcccggt gtgaaatacc    4920
gcacagatgc gtaaggagaa ataccgcat caggcgctct ccgcttcct cgctcactga      4980
ctcgctgcgc tcggtcgttc ggctgcgcg agcggtatca gctcactcaa aggcggtaat    5040
acggttatcc acagaatcag gggataacgc aggaaagaac atgtgagcaa aaggccagca    5100
aaaggccagg aaccgtaaaa aggccgcgtt gctggcgttt ttccataggc tccgcccccc    5160
tgacgagcat cacaaaaatc gacgctcaag tcagaggtgg cgaaacccga caggactata    5220
aagataccag gcgtttcccc ctggaagctc cctcgtgcgc tctcctgttc cgaccctgcc    5280
gcttaccgga tacctgtccg cctttctccc ttcgggaagc gtggcgcttt ctcatagctc    5340
```

```
acgctgtagg tatctcagtt cggtgtaggt cgttcgctcc aagctgggct gtgtgcacga    5400
acccccgtt cagcccgacc gctgcgcctt atccggtaac tatcgtcttg agtccaaccc    5460
ggtaagacac gacttatcgc cactggcagc agccactggt aacaggatta gcagagcgag    5520
gtatgtaggc ggtgctacag agttcttgaa gtggtggcct aactacggct acactagaag    5580
gacagtattt ggtatctgcg ctctgctgaa gccagttacc ttcggaaaaa gagttggtag    5640
ctcttgatcc ggcaaacaaa ccaccgctgg tagcggtggt ttttttgttt gcaagcagca    5700
gattacgcgc agaaaaaaag gatctcaaga agatcctttg atcttttcta cggggtctga    5760
cgctcagtgg aacgaaaact cacgttaagg gattttggtc atgagattat caaaaaggat    5820
cttcacctag atccttttaa aggccggccg cggccgcgca aagtcccgct tcgtgaaaat    5880
tttcgtgccg cgtgattttc cgccaaaaac tttaacgaac gttcgttata atggtgtcat    5940
gaccttcacg acgaagtact aaaattggcc cgaatcatca gctatggatc tctctgatgt    6000
cgcgctggag tccgacgcgc tcgatgctgc cgtcgattta aaaacggtga tcggattttt    6060
ccgagctctc gatacgacgg acgcgccagc atcacgagac tgggccagtg ccgcgagcga    6120
cctagaaact ctcgtggcgg atcttgagga gctggctgac gagctgcgtg ctcggccagc    6180
gccaggagga cgcacagtag tggaggatgc aatcagttgc gcctactgcg gtggcctgat    6240
tcctccccgg cctgacccgc gaggacggcg cgcaaaatat tgctcagatg cgtgtcgtgc    6300
cgcagccagc cgcgagcgcg ccaacaaacg ccacgccgag gagctggagg cggctaggtc    6360
gcaaatggcg ctggaagtgc gtcccccgag cgaaattttg gccatggtcg tcacagagct    6420
ggaagcggca gcgagaatta tcgcgatcgt ggcggtgccc gcaggcatga caaacatcgt    6480
aaatgccgcg tttcgtgtgc cgtggccgcc caggacgtgt cagcgccgcc accacctgca    6540
ccgaatcggc agcagcgtcg cgcgtcgaaa aagcgcacag gcggcaagaa gcgataagct    6600
gcacgaatac ctgaaaaatg ttgaacgccc cgtgagcggt aactcacagg gcgtcggcta    6660
acccccagtc caaacctggg agaaagcgct caaaaatgac tctagcggat tcacgagaca    6720
ttgacacacc ggcctggaaa ttttccgctg atctgttcga cacccatccc gagctcgcgc    6780
tgcgatcacg tggctggacg agcgaagacc gccgcgaatt cctcgctcac ctgggcagag    6840
aaaatttcca gggcagcaag acccgcgact tcgccagcgc ttggatcaaa gacccggaca    6900
cggagaaaca cagccgaagt tataccgagt tggttcaaaa tcgcttgccc ggtgccagta    6960
tgttgctctg acgcacgcgc agcacgcagc cgtgcttgtc ctggacattg atgtgccgag    7020
ccaccaggcc ggcgggaaaa tcgagcacgt aaaccccgag gtctacgcga ttttggagcg    7080
ctgggcacgc ctggaaaaag cgccagcttg gatcggcgtg aatccactga gcgggaaatg    7140
ccagctcatc tggctcattg atccggtgta tgccgcagca ggcatgagca gcccgaatat    7200
gcgcctgctg gctgcaacga ccgaggaaat gacccgcgtt ttcggcgctg accaggcttt    7260
ttcacatagg ctgagccgtg gccactgcac tctccgacga tcccagccgt accgctggca    7320
tgcccagcac aatcgcgtgg atcgcctagc tgatcttatg gaggttgctc gcatgatctc    7380
aggcacagaa aaacctaaaa aacgctatga gcaggagttt tctagcggac gggcacgtat    7440
cgaagcggca agaaaagcca ctgcggaagc aaaagcactt gccacgcttg aagcaagcct    7500
gccgagcgcc gctgaagcgt ctggagagct gatcgacggc gtccgtgtcc tctgactgc    7560
tccagggcgt gccgcccgtg atgagacggc ttttcgccac gctttgactg tgggatacca    7620
gttaaaagcg gctggtgagc gcctaaaaga caccaagggt catcgagcct acgagcgtgc    7680
ctacaccgtc gctcaggcgg tcggaggagg ccgtgagcct gatctgccgc cggactgtga    7740
```

```
ccgccagacg gattggccgc gacgtgtgcg cggctacgtc gctaaaggcc agccagtcgt    7800
ccctgctcgt cagacagaga cgcagagcca gccgaggcga aaagctctgg ccactatggg    7860
aagacgtggc ggtaaaaagg ccgcagaacg ctggaaagac ccaaacagtg agtacgcccg    7920
agcacagcga gaaaaactag ctaagtccag tcaacgacaa gctaggaaag ctaaaggaaa    7980
tcgcttgacc attgcaggtt ggtttatgac tgttgaggga gagactggct cgtggccgac    8040
aatcaatgaa gctatgtctg aatttagcgt gtcacgtcag accgtgaata gagcacttaa    8100
ggtctgcggg cattgaactt ccacgaggac gccgaaagct tcccagtaaa tgtgccatct    8160
cgtaggcaga aaacggttcc cccgtagggt ctctctcttg gcctcctttc taggtcgggc    8220
tgattgctct tgaagctctc taggggggct cacaccatag gcagataacg ttccccaccg    8280
gctcgcctcg taagcgcaca aggactgctc ccaaagatct tcaaagccac tgccgcgact    8340
gccttcgcga agccttgccc cgcggaaatt tcctccaccg agttcgtgca caccctatg     8400 ccaagcttct ttcaccctaa attcgagaga ttggattctt accgtggaaa ttcttcgcaa    8460
aaatcgtccc ctgatcgccc ttgcgacgtt ggcgtcggtg ccgctggttg cgcttggctt    8520
gaccgacttg atcagcggcc gctcgattta aatc                                8554

<210> SEQ ID NO 14
<211> LENGTH: 6583
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 14
gtaccacgcg tcatatgcgg cttaaagttt ggctgccatg tgaattttta gcaccctcaa      60
cagttgagtg ctggcactct cgggggtaga gtgccaaata ggttgtttga cacacagttg     120
ttcacccgcg acgacggctg tgctggaaac ccacaaccgg cacacacaaa attttctca      180 tggagggatt catcatgcca aagtacgaca attccaatgc tgaccagtgg ggctttgaaa     240
cccgctccat tcacgcaggc cagtcagtag acgcacagac cagcgcacga aaccttccga     300
tctaccaatc caccgctttc gtgttcgact ccgctgagca cgccaagcag cgtttcgcac     360
ttgaggatct aggccctgtt tactcccgcc tcaccaaccc aaccgttgag gctttggaaa     420
accgcatcgc ttccctcgaa ggtggcgtcc acgctgtagc gttctcctcc ggacaggccg     480
caaccaccaa cgccattttg aacctggcag gagcgggcga ccacatcgtc acctccccac     540
gcctctacgg tggcaccgag actctattcc ttatcactct taaccgcctg ggtatcgatg     600
tttccttcgt ggaaaacccc gacgaccctg agtcctggca ggcagccgtt cagccaaaca     660
ccaaagcatt cttcggcgag actttcgcca acccacaggc agacgtcctg gatattcctg     720
cggtggctga agttgcgcac cgcaacagcg ttccactgat catcgacaac accatcgcta     780
ccgcagcgct cgtgcgcccg ctcgagctcg gcgcagacgt tgtcgtcgct tccctcacca     840
agttctacac cggcaacggc tccggactgg gcggcgtgct tatcgacggc ggaaagttcg     900
attggactgt cgaaaaggat ggaaagccag tattcccccta cttcgtcact ccagatgctg     960
cttaccacgg attgaagtac gcagaccttg gtgcaccagc cttcggcctc aaggttcgcg    1020
ttggccttct acgcgacacc ggctccaccc tctccgcatt caacgcatgg gctgcagtcc    1080
agggcatcga caccctttcc ctgcgcctgg agcgccacaa cgaaaacgcc atcaaggttg    1140
cagaattcct caacaaccac gagaaggtgg aaaaggttaa cttcgcaggc ctgaaggatt    1200 cccccttggta cgcaaccaag gaaaagcttg gcctgaagta caccggctcc gttctcacct    1260
```

```
tcgagatcaa gggcggcaag gatgaggctt gggcatttat cgacgccctg aagctacact   1320
ccaaccttgc aaacatcggc gatgttcgct ccctcgttgt tcacccagca accaccaccc   1380
attcacagtc cgacgaagct ggcctggcac gcgcgggcgt tacccagtcc accgtccgcc   1440
tgtccgttgg catcgagacc attgatgata tcatcgctga cctcgaaggc ggctttgctg   1500
caatctagca ctagttcgga cctaggata tcgtcgacat cgatgctctt ctgcgttaat    1560
taacaattgg gatcctctag acccgggatt taaatcgcta gcgggctgct aaaggaagcg   1620
gaacacgtag aaagccagtc cgcagaaacg gtgctgaccc cggatgaatg tcagctactg   1680
ggctatctgg acaagggaaa acgcaagcgc aaagagaaag caggtagctt gcagtgggct   1740
tacatggcga tagctagact gggcggtttt atggacagca agcgaaccgg aattgccagc   1800
tggggcgccc tctggtaagg ttgggaagcc ctgcaaagta aactggatgg ctttcttgcc   1860
gccaaggatc tgatggcgca ggggatcaag atctgatcaa gagacaggat gaggatcgtt   1920
tcgcatgatt gaacaagatg gattgcacgc aggttctccg gccgcttggg tggagaggct   1980
attcggctat gactgggcac aacagacaat cggctgctct gatgccgccg tgttccggct   2040
gtcagcgcag gggcgcccgg ttcttttttgt caagaccgac ctgtccggtg ccctgaatga   2100
actgcaggac gaggcagcgc ggctatcgtg gctggccacg acgggcgttc cttgcgcagc   2160
tgtgctcgac gttgtcactg aagcgggaag ggactggctg ctattgggcg aagtgccggg   2220
gcaggatctc ctgtcatctc accttgctcc tgccgagaaa gtatccatca tggctgatgc   2280
aatgcggcgg ctgcatacgc ttgatccggc tacctgccca ttcgaccacc aagcgaaaca   2340
tcgcatcgag cgagcacgta ctcggatgga agccggtctt gtcgatcagg atgatctgga   2400
cgaagagcat caggggctcg cgccagccga actgttcgcc aggctcaagg cgcgcatgcc   2460
cgacggcgag gatctcgtcg tgacccatgg cgatgcctgc ttgccgaata tcatggtgga   2520
aaatggccgc ttttctggat tcatcgactg tggccggctg ggtgtggcgg accgctatca   2580
ggacatagcg ttggctaccc gtgatattgc tgaagagctt ggcggcgaat gggctgaccg   2640
cttcctcgtg ctttacggta tcgccgctcc cgattcgcag cgcatcgcct tctatcgcct   2700
tcttgacgag ttcttctgag cgggactctg gggttcgaaa tgaccgacca agcgacgccc   2760
aacctgccat cacgagattt cgattccacc gccgccttct atgaaaggtt gggcttcgga   2820
atcgttttcc gggacgccgg ctggatgatc ctccagcgcg gggatctcat gctggagttc   2880
ttcgcccacg ctagcggcgc gccggccggc ccggtgtgaa ataccgcaca gatgcgtaag   2940
gagaaaatac cgcatcaggc gctcttccgc ttcctcgctc actgactcgc tgcgctcggt   3000
cgttcggctg cggcgagcgg tatcagctca ctcaaaggcg gtaatacggt tatccacaga   3060
atcaggggat aacgcaggaa agaacatgtg agcaaaaggc cagcaaaagg ccaggaaccg   3120
taaaaaggcc gcgttgctgg cgttttttcca taggctccgc ccccctgacg agcatcacaa   3180
aaatcgacgc tcaagtcaga ggtggcgaaa cccgacagga ctataaagat accaggcgtt   3240
tccccctgga agctccctcg tgcgctctcc tgttccgacc ctgccgctta ccggatacct   3300
gtccgccttt ctcccttcgg gaagcgtggc gctttctcat agctcacgct gtaggtatct   3360
cagttcggtg taggtcgttc gctccaagct gggctgtgtg cacgaacccc ccgttcagcc   3420
cgaccgctgc gccttatccg gtaactatcg tcttgagtcc aacccggtaa gacacgactt   3480
atcgccactg gcagcagcca ctggtaacag gattagcaga gcgaggtatg taggcggtgc   3540
tacagagttc ttgaagtggt ggcctaacta cggctacact agaaggacag tatttggtat   3600
ctgcgctctg ctgaagccag ttaccttcgg aaaaagagtt ggtagctctt gatccggcaa   3660
```

```
acaaaccacc gctggtagcg gtggttttt tgtttgcaag cagcagatta cgcgcagaaa    3720
aaaaggatct caagaagatc ctttgatctt ttctacgggg tctgacgctc agtggaacga    3780
aaactcacgt taagggattt tggtcatgag attatcaaaa aggatcttca cctagatcct    3840
tttaaaggcc ggccgcggcc gcgcaaagtc ccgcttcgtg aaaattttcg tgccgcgtga    3900
ttttccgcca aaactttaa cgaacgttcg ttataatggt gtcatgacct tcacgacgaa    3960
gtactaaaat tggcccgaat catcagctat ggatctctct gatgtcgcgc tggagtccga    4020
cgcgctcgat gctgccgtcg atttaaaaac ggtgatcgga ttttccgag ctctcgatac     4080
gacggacgcg ccagcatcac gagactgggc cagtgccgcg agcgacctag aaactctcgt    4140
ggcggatctt gaggagctgg ctgacgagct gcgtgctcgg ccagcgccag gaggacgcac    4200
agtagtggag gatgcaatca gttgcgccta ctgcggtggc ctgattcctc cccggcctga    4260
cccgcgagga cggcgcgcaa aatattgctc agatgcgtgt cgtgccgcag ccagccgcga    4320
gcgcgccaac aaacgccacg ccgaggagct ggaggcggct aggtcgcaaa tggcgctgga    4380
agtgcgtccc ccgagcgaaa ttttggccat ggtcgtcaca gagctggaag cggcagcgag    4440
aattatcgcg atcgtggcgg tgcccgcagg catgacaaac atcgtaaatg ccgcgtttcg    4500
tgtgccgtgg ccgcccagga cgtgtcagcg ccgccaccac ctgcaccgaa tcggcagcag    4560
cgtcgcgcgt cgaaaaagcg cacaggcggc aagaagcgat aagctgcacg aatacctgaa    4620
aaatgttgaa cgccccgtga gcggtaactc acagggcgtc ggctaacccc cagtccaaac    4680
ctgggagaaa gcgctcaaaa atgactctag cggattcacg agacattgac acaccggcct    4740
ggaaattttc cgctgatctg ttcgacaccc atcccgagct cgcgctgcga tcacgtggct    4800
ggacgagcga agaccgccgc gaattcctcg ctcacctggg cagagaaaat ttccagggca    4860
gcaagacccg cgacttcgcc agcgcttgga tcaaagaccc ggacacggag aaacacagcc    4920
gaagttatac cgagttggtt caaaatcgct tgcccggtgc cagtatgttg ctctgacgca    4980
cgcgcagcac gcagccgtgc ttgtcctgga cattgatgtg ccgagccacc aggccggcgg    5040
gaaaatcgag cacgtaaacc ccgaggtcta cgcgattttg gagcgctggg cacgcctgga    5100
aaaagcgcca gcttggatcg gcgtgaatcc actgagcggg aaatgccagc tcatctggct    5160
cattgatccg gtgtatgccg cagcaggcat gagcagcccg aatatgcgcc tgctggctgc    5220
aacgaccgag gaaatgaccc gcgttttcgg cgctgaccag gcttttttcac ataggctgag    5280
ccgtggccac tgcactctcc gacgatccca gccgtaccgc tggcatgccc agcacaatcg    5340
cgtggatcgc ctagctgatc ttatggaggt tgctcgcatg atctcaggca cagaaaaacc    5400
taaaaacgc tatgagcagg agttttctag cggacgggca cgtatcgaag cggcaagaaa      5460
agccactgcg gaagcaaaag cacttgccac gcttgaagca agcctgccga gcgccgctga    5520
agcgtctgga gagctgatcg acggcgtccg tgtcctctgg actgctccag ggcgtgccgc    5580
ccgtgatgag acggcttttc gccacgcttt gactgtggga taccagttaa aagcggctgg    5640
tgagcgccta aaagacacca agggtcatcg agcctacgag cgtgcctaca ccgtcgctca    5700
ggcggtcgga ggaggccgtg agcctgatct gccgccggac tgtgaccgcc agacggattg    5760
gccgcgacgt gtgcgcggct acgtcgctaa aggccagcca gtcgtccctg ctcgtcagac    5820
agagacgcag agccagccga ggcgaaaagc tctggccact atgggaagac gtggcggtaa    5880
aaaggccgca gaacgctgga aagacccaaa cagtgagtac gcccgagcac agcgagaaaa    5940
actagctaag tccagtcaac gacaagctag gaaagctaaa ggaaatcgct tgaccattgc    6000
aggttggttt atgactgttg agggagagac tggctcgtgg ccgacaatca atgaagctat    6060
```

```
gtctgaattt agcgtgtcac gtcagaccgt gaatagagca cttaaggtct gcgggcattg    6120
aacttccacg aggacgccga aagcttccca gtaaatgtgc catctcgtag gcagaaaacg    6180
gttcccccgt agggtctctc tcttggcctc ctttctaggt cgggctgatt gctcttgaag    6240
ctctctaggg gggctcacac cataggcaga taacgttccc caccggctcg cctcgtaagc    6300
gcacaaggac tgctcccaaa gatcttcaaa gccactgccg cgactgcctt cgcgaagcct    6360
tgccccgcgg aaatttcctc caccgagttc gtgcacaccc ctatgccaag cttcttttcac   6420 cctaaattcg agagattgga ttcttaccgt ggaaattctt cgcaaaaatc gtccctgat     6480 cgcccttgcg acgttggcgt cggtgccgct ggttgcgctt ggcttgaccg acttgatcag    6540
cggccgctcg atttaaatct cgagaggcct gacgtcgggc ccg                      6583

<210> SEQ ID NO 15
<211> LENGTH: 5091
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 15
tcgatttaaa tctcgagagg cctgacgtcg ggcccggtac cacgcgtcat atgactagtt     60
cggacctagg gatatcgtcg acatcgatgc tcttctgcgt taattaacaa ttgggatcct    120
ctagacccgg gatttaaatc gctagcgggc tgctaaagga agcggaacac gtagaaagcc    180
agtccgcaga aacggtgctg accccggatg aatgtcagct actgggctat ctggacaagg    240
gaaaacgcaa gcgcaaagag aaagcaggta gcttgcagtg gcttacatg gcgatagcta    300 gactgggcgg ttttatggac agcaagcgaa ccggaattgc cagctggggc gccctctggt    360
aaggttggga agccctgcaa agtaaactgg atggctttct gccgccaag atctgatgg    420 cgcaggggat caagatctga tcaagagaca ggatgaggat cgtttcgcat gattgaacaa    480
gatggattgc acgcaggttc tccggccgct tgggtggaga ggctattcgg ctatgactgg    540
gcacaacaga caatcggctg ctctgatgcc gccgtgttcc ggctgtcagc gcaggggcgc    600
ccggttcttt ttgtcaagac cgacctgtcc ggtgccctga tgaactgca ggacgaggca    660 gcgcggctat cgtggctggc cacgacgggc gttccttgcg cagctgtgct cgacgttgtc    720
actgaagcgg gaagggactg gctgctattg ggcgaagtgc cggggcagga tctcctgtca    780
tctcaccttg ctcctgccga gaaagtatcc atcatggctg atgcaatgcg gcggctgcat    840
acgcttgatc cggctacctg cccattcgac caccaagcga acatcgcat cgagcgagca    900 cgtactcgga tggaagccgg tcttgtcgat caggatgatc tggacgaaga gcatcagggg    960
ctcgcgccag ccgaactgtt cgccaggctc aaggcgcgca tgcccgacgg cgaggatctc    1020
gtcgtgaccc atggcgatgc ctgcttgccg aatatcatgg tggaaaatgg ccgcttttct    1080
ggattcatcg actgtggccg gctgggtgtg gcggaccgct atcaggacat agcgttggct    1140
acccgtgata ttgctgaaga gcttggcggc gaatgggctg accgcttcct cgtgctttac    1200
ggtatcgccg ctcccgattc gcagcgcatc gccttctatc gccttcttga cgagttcttc    1260
tgagcgggac tctggggttc gaaatgaccg accaagcgac gcccaacctg ccatcacgag    1320
atttcgattc caccgccgcc ttctatgaaa ggttgggctt cggaatcgtt ttccgggacg    1380
ccggctggat gatcctccag cgcggggatc tcatgctgga gttcttcgcc cacgctagcg    1440
gcgcgccggc cggcccggtg tgaaataccg cacagatgcg taaggagaaa ataccgcatc    1500
```

-continued

```
aggcgctctt ccgcttcctc gctcactgac tcgctgcgct cggtcgttcg gctgcggcga   1560
gcggtatcag ctcactcaaa ggcggtaata cggttatcca cagaatcagg ggataacgca   1620
ggaaagaaca tgtgagcaaa aggccagcaa aaggccagga accgtaaaaa ggccgcgttg   1680
ctggcgtttt tccataggct ccgcccccct gacgagcatc acaaaaatcg acgctcaagt   1740
cagaggtggc gaaacccgac aggactataa agataccagg cgtttccccc tggaagctcc   1800
ctcgtgcgct ctcctgttcc gaccctgccg cttaccggat acctgtccgc ctttctccct   1860
tcgggaagcg tggcgctttc tcatagctca cgctgtaggt atctcagttc ggtgtaggtc   1920
gttcgctcca agctgggctg tgtgcacgaa ccccccgttc agcccgaccg ctgcgcctta   1980
tccggtaact atcgtcttga gtccaacccg gtaagacacg acttatcgcc actggcagca   2040
gccactggta acaggattag cagagcgagg tatgtaggcg gtgctacaga gttcttgaag   2100
tggtggccta actacggcta cactagaagg acagtatttg gtatctgcgc tctgctgaag   2160
ccagttacct tcggaaaaag agttggtagc tcttgatccg gcaaacaaac caccgctggt   2220
agcggtggtt tttttgtttg caagcagcag attacgcgca gaaaaaaagg atctcaagaa   2280
gatcctttga tcttttctac ggggtctgac gctcagtgga acgaaaactc acgttaaggg   2340
attttggtca tgagattatc aaaaaggatc ttcacctaga tccttttaaa ggccggccgc   2400
ggccgcgcaa agtcccgctt cgtgaaaatt ttcgtgccgc gtgattttcc gccaaaaact   2460
ttaacgaacg ttcgttataa tggtgtcatg accttcacga cgaagtacta aaattggccc   2520
gaatcatcag ctatggatct ctctgatgtc gcgctggagt ccgacgcgct cgatgctgcc   2580
gtcgatttaa aaacggtgat cggattttc cgagctctcg atacgacgga cgcgccagca   2640
tcacgagact gggccagtgc cgcgagcgac ctagaaactc tcgtggcgga tcttgaggag   2700
ctggctgacg agctgcgtgc tcggccagcg ccaggaggac gcacagtagt ggaggatgca   2760
atcagttgcg cctactgcgg tggcctgatt cctccccggc ctgacccgcg aggacgcgc   2820
gcaaaatatt gctcagatgc gtgtcgtgcc gcagccagcc gcgagcgcgc caacaaacgc   2880
cacgccgagg agctggaggc ggctaggtcg caaatggcgc tggaagtgcg tcccccgagc   2940
gaaattttgg ccatggtcgt cacagagctg gaagcggcag cgagaattat cgcgatcgtg   3000
gcggtgcccg caggcatgac aaacatcgta atgccgcgt tcgtgtgcc gtggccgccc   3060
aggacgtgtc agcgccgcca ccacctgcac cgaatcggca gcagcgtcgc gcgtcgaaaa   3120
agcgcacagg cggcaagaag cgataagctg cacgaatacc tgaaaaatgt tgaacgcccc   3180
gtgagcggta actcacaggg cgtcggctaa ccccccagtcc aaacctggga gaaagcgctc   3240
aaaaatgact ctagcggatt cacgagacat tgacacaccg gcctggaaat tttccgctga   3300
tctgttcgac acccatcccg agctcgcgct gcgatcacgt ggctgacga gcgaagaccg   3360
ccgcgaattc ctcgctcacc tgggcagaga aaatttccag ggcagcaaga cccgcgactt   3420
cgccagcgct tggatcaaag acccggacac ggagaaacac agccgaagtt ataccgagtt   3480
ggttcaaaat cgcttgcccg gtgccagtat gttgctctga cgcacgcgca gcacgcagcc   3540
gtgcttgtcc tggacattga tgtgccgagc caccaggccg gcgggaaaat cgagcacgta   3600
aaccccgagg tctacgcgat tttggagcgc tgggcacgcc tggaaaaagc gccagcttgg   3660
atcgcgtga atccactgag cgggaaatgc cagctcatct ggctcattga tccggtgtat   3720
gccgcagcag gcatgagcag cccgaatatg cgcctgctgg ctgcaacgac cgaggaaatg   3780
acccgcgttt tcgcgctga ccaggctttt tcacataggc tgagccgtgg ccactgcact   3840
ctccgacgat cccagccgta ccgctggcat gcccagcaca atcgcgtgga tcgcctagct   3900
```

```
gatcttatgg aggttgctcg catgatctca ggcacagaaa aacctaaaaa acgctatgag    3960
caggagtttt ctagcggacg ggcacgtatc gaagcggcaa gaaaagccac tgcggaagca    4020
aaagcacttg ccacgcttga agcaagcctg ccgagcgccg ctgaagcgtc tggagagctg    4080
atcgacggcg tccgtgtcct ctggactgct ccagggcgtg ccgcccgtga tgagacggct    4140
tttcgccacg ctttgactgt gggataccag ttaaaagcgg ctggtgagcg cctaaaagac    4200
accaagggtc atcgagccta cgagcgtgcc tacaccgtcg ctcaggcggt cggaggaggc    4260
cgtgagcctg atctgccgcc ggactgtgac cgccagacgg attggccgcg acgtgtgcgc    4320
ggctacgtcg ctaaaggcca gccagtcgtc cctgctcgtc agacagagac gcagagccag    4380
ccgaggcgaa aagctctggc cactatggga agacgtggcg gtaaaaaggc cgcagaacgc    4440
tggaaagacc caaacagtga gtacgcccga gcacagcgaa aaaaactagc taagtccagt    4500
caacgacaag ctaggaaagc taaaggaaat cgcttgacca ttgcaggttg gtttatgact    4560
gttgagggag agactggctc gtggccgaca atcaatgaag ctatgtctga atttagcgtg    4620
tcacgtcaga ccgtgaatag agcacttaag gtctgcgggc attgaacttc cacgaggacg    4680
ccgaaagctt cccagtaaat gtgccatctc gtaggcagaa aacggttccc ccgtagggtc    4740
tctctcttgg cctcctttct aggtcgggct gattgctctt gaagctctct aggggggctc    4800
acaccatagg cagataacgt tccccaccgg ctcgcctcgt aagcgcacaa ggactgctcc    4860
caaagatctt caaagccact gccgcgactg ccttcgcgaa gccttgcccc gcggaaattt    4920
cctccaccga gttcgtgcac accccctatgc caagcttctt tcaccctaaa ttcgagagat    4980
tggattctta ccgtggaaat tcttcgcaaa aatcgtcccc tgatcgccct tgcgacgttg    5040
gcgtcggtgc cgctggttgc gcttggcttg accgacttga tcagcggccg c            5091
```